(12) United States Patent
Tasaka et al.

(10) Patent No.: US 6,649,643 B1
(45) Date of Patent: *Nov. 18, 2003

(54) IMIDAZOL-4-YLMEHANOLS AND THEIR USE AS INHIBITORS OF STEROID C17-20 LYASE

(75) Inventors: Akihiro Tasaka, Suita (JP); Akio Ojida, Fukuoka (JP); Tomohiro Kaku, Nishinomiya (JP); Masami Kusaka, Kobe (JP); Masuo Yamaoka, Kobe (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/110,599

(22) PCT Filed: Oct. 19, 2000

(86) PCT No.: PCT/JP00/07283

§ 371 (c)(1), (2), (4) Date: Apr. 12, 2002

(87) PCT Pub. No.: WO01/30762

PCT Pub. Date: May 3, 2001

(30) Foreign Application Priority Data

Oct. 22, 1999 (JP) .......................................... 11-301556
Jun. 20, 2000 (JP) ....................................... 2000-189728

(51) Int. Cl.[7] ................ A61K 31/4164; A61K 31/4178; C07D 233/64; C07D 407/06
(52) U.S. Cl. ................ 514/400; 548/341.1; 548/338.1; 548/341.5; 548/110; 548/336.1; 548/342.1; 548/315.4; 548/315.1; 548/255; 548/250; 548/252; 548/312.4; 548/235; 548/311.4; 548/314.7; 548/195; 548/237; 548/311.7; 514/63; 514/365; 514/374; 514/381; 514/359; 514/397

(58) Field of Search ........................ 548/341.1; 514/400

(56) References Cited

FOREIGN PATENT DOCUMENTS

| EP | 0168965 | 1/1986 |
|---|---|---|
| EP | 0503785 | 9/1992 |
| EP | 0721943 | 7/1996 |
| EP | 1193258 | 4/2002 |
| WO | 0820989 | 1/1999 |
| WO | WO 99/54309 | 10/1999 |
| WO | WO 00/78727 | 12/2000 |
| WO | WO 01/30763 | 5/2001 |

OTHER PUBLICATIONS

Asinger, et al. "Joint Action of Elemental Sulfur and Gaseous Ammonia on Ketones. 89. Migration of Acyl Groups in N–acyl–2H–Imidazole–4(3H)—Thiones", CA 84:74182, 1976.

*Primary Examiner*—Laura L. Stockton
(74) *Attorney, Agent, or Firm*—Mark Chao; Elaine M. Ramesh

(57) ABSTRACT

Imidazol-4-ylmethanols and their uses for preventing and treating primary tumors, metastasis and recurrence of tumors, various symptoms accompanying tumors, prostatic hypertrophy, virilism, hirsutism, male pattern alopecia, precocious puberty, endometriosis, uterine myoma, mastopathy and polycystic ovary syndrome are disclosed.

17 Claims, 1 Drawing Sheet

IMIDAZOL-4-YLMEHANOLS AND THEIR USE AS INHIBITORS OF STEROID C17-20 LYASE

This application is the National Phase filing of International Patent Application No. PCT/JP00/07283, filed Oct. 19, 2000.

TECHNICAL FIELD

The present invention relates to a medicine, especially to novel naphthalene derivatives having a steroid $C_{17,20}$-lyase inhibitory activity, or its production and pharmaceutical compositions containing the same.

BACKGROUND ART

Androgen and estrogen, each of which is a sex hormone, are essential in a living body and have various physiological activities such as differentiation and proliferation of cell, etc. On the other hand, it has been found that each of androgen and estrogen works as a exacerbation factor in some diseases.

It is known that, in the biosynthesis of androgen in vivo, steroid $C_{17,20}$-lyase acts at the final stage. That is, steroid $C_{17,20}$-lyase converts 17-hydroxypregnenolone and 17-hydroxyprogesterone derived from cholesterol to dehydroepiandrosterone and androstenedione, respectively. Therefore, a medicine having a steroid $C_{17,20}$-lyase inhibitory activity suppresses the formation of androgen and estrogen which is produced from androgen, and is useful for preventing and treating diseases whose exacerbation factor is androgen or estrogen. As the disease whose exacerbation factor is androgen or estrogen, there may be mentioned, for example, prostate cancer, prostatic hypertrophy, virilism, hirsutism, male pattern alopecia, precocious puberty, breast cancer, uterine cancer, mastopathy, uterus myoma, endometriosis, adenomyosis of uterus, polycystic ovary syndrome, etc.

It has been already known that some steroid type compounds and some non-steroid type compounds inhibit steroid $C_{17,20}$-lyase. The steroid type compounds are disclosed in, for example, WO 92/15404, WO 93/20097, EP-A 288053, EP-A 413270, etc. As non-steroid type compounds, for example, (1H-imidazol-1-yl)methyl-substituted benzimidazole derivatives are shown in Japanese Published Unexamined Patent Application No. 85975/1989, carbazole derivatives are shown in WO94/27989 and WO96/14090, azole derivatives are shown in WO95/09157, 1H-benzimidazole derivatives are shown in U.S. Pat. No. 5,491,161, dihydronaphthalene derivatives are shown in WO99/18075.

Heretofore, steroid $C_{17,20}$-lyase inhibitors which can actually be used as medicine have not been known. Thus, it has been expected the early development of steroid $C_{17,20}$-lyase inhibitors which are useful as medicine.

DISCLOSURE OF INVENTION

The present invention provides:
(1) A compound of the formula:

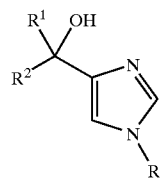

(I)

wherein R is a hydrogen atom or a protecting group, $R^1$ is a lower alkyl group or a cyclic alkyl group, $R^2$ is a group represented by the formula:

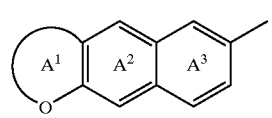

(1)

(wherein a ring $A^1$ is a 5- or 6-membered ring containing an oxygen atom optionally having substituents, and a ring $A^2$ and a ring $A^3$ may have substituents), a group represented by the formula:

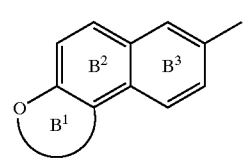

(2)

(wherein the ring $B^1$ is a 5- or 6-membered ring containing an oxygen atom optionally having substituents and a ring $B^2$ and a ring $B^3$ may have substituents) or a group of the formula:

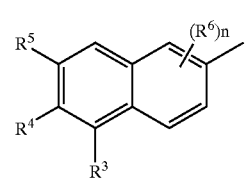

(3)

(wherein each of $R^3$, $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3.), or a salt thereof, (2) A compound as defined in (1), wherein R is (i) a hydrogen atom, (ii) a formyl group or (iii) a $C_{1-6}$ alkyl-carbonyl group, a phenyl-carbonyl group, a $C_{1-6}$ alkyl-oxycarbonyl group, an allyl-oxycarbonyl group, a phenyloxycarbonyl group, a $C_{7-10}$ aralkyl-oxy-carbonyl group, a trityl group, a N,N-dimethylaminosulfonyl group, a $C_{7-16}$ aralkyl-oxy-$C_{1-6}$ alkyl group each of which optionally has substituents selected from the group consisting of a halogen atom, a $C_{1-6}$ alkyl-carbonyl and nitro, $R^1$ is a straight chain or branched $C_{1-6}$ alkyl group or a $C_{3-6}$ cycloalkyl group, the ring $A^1$ is a 5- or 6-membered ring containing an oxygen atom together with carbon atoms as ring constituting atoms and the ring may further contain a nitrogen atom and a sulfur atom as the ring constituting atoms, optionally having 1 to 4 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group, the ring $A^2$ and the ring $A^3$ may have 1 to 3 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group at any substitutable position, the ring $B^1$ is a 5- or 6-membered ring containing an oxygen atom together with carbon atoms as ring constituting atoms and the ring may further contain a nitrogen atom and a sulfur atom as the ring constituting atoms, optionally having 1 to 4 substituents selected from the group consisting of (i) a $C_{1-4}$ alkyl group optionally having substituents optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group, the ring $B^2$ and the ring $B^3$ may have 1 to 3 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group at any substitutable position, $R^3$ and $R^5$ is independently
- (i) a hydrogen atom,
- (ii) a $C_{1-4}$ alkyl group optionally having substituents selected from the group consisting of $C_{1-4}$ alkanoyl, carboxyl and $C_{1-4}$ alkoxy-carbonyl,
- (iii) a group selected from the group consisting of a hydroxy group, a $C_{1-4}$ alkoxy group, a $C_{1-4}$ alkanoyloxy group, a carbamoyloxy group and a mono- or di-$C_{1-4}$ alkyl-carbamoyloxy group,
- (iv) a group selected from the group consisting of a thiol group, a $C_{1-4}$ alkylthio group and a $C_{1-4}$ alkanoylthio group,
- (v) a group selected from the group consisting of an amino group, a $C_{1-4}$ alkyl amino group, a di-$C_{1-4}$ alkylamino group and a $C_{1-4}$ alkanoylamino group,
- (vi) an acyl group selected from the group consisting of a formyl group, a $C_{1-6}$ alkanoyl group, a $C_{1-4}$ alkylsulfonyl group, a carbamoyl group, a mono- or di-$C_{1-10}$ alkyl carbamoyl group, a mono- or di-$C_{6-14}$ arylcarbamoyl group, a mono- or di-$C_{7-16}$ aralkyl carbamoyl group, a sulfamoyl group, a mono- or di-$C_{1-10}$ alkylsulfamoyl group, a mono- or di-$C_{6-14}$ arylsulfamoyl group and a mono- or di-$C_{7-16}$ aralkyl sulfamoyl group, or
- (vii) a halogen atom, $R^4$ is
- (I) a $C_{6-14}$ aryl group optionally having substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group,
- (II) a 3- to 13-membered heterocyclic group which contains 1 to 4 hetero atoms selected from the group consisting of a nitrogen atom, an oxygen atom and a sulfur atom other than carbon atoms, optionally having substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group,
- (III) a carbamoyl group,
- (IV) a mono- or di-$C_{1-10}$ alkyl-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl,
- (V) a mono- or di-$C_{3-7}$ cycloalkyl-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl,
- (VI) a mono- or di-$C_{6-14}$ aryl carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (VII) a mono- or di-$C_{7-16}$ aralkyl carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (VIII) a 3- to 7-membered cyclic amino-carbonyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (IX) a 5- or 6-membered heterocyclic-carbamoyl group which contains 1 to 4 hetero atoms selected from a nitrogen atom, an oxygen atom and a sulfur atom other than carbon atoms optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, or (X) a $C_{1-6}$ alkoxy-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, $R^6$ is an optionally halogenated $C_{1-6}$ alkyl group, and n is an integer of 0 to 3, (3) A compound as defined in (1), wherein R is a hydrogen atom or a protecting group, $R^1$ is a lower alkyl group or a cyclic alkyl group, $R^2$ is a group of the formula:

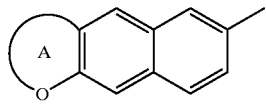

(1)

(wherein the ring A is a 5- or 6-membered ring containing an oxygen atom), a group of the formula:

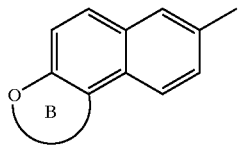

(2)

(wherein the ring B is a 5- or 6-membered ring containing an oxygen atom) or a group of the formula:

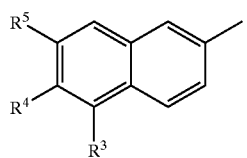

(3)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, and $R^4$ is an aromatic hydrocarbon group optionally having substituents, a heterocyclic group optionally having substituents or a carbamoyl group optionally having substituents), (4) A compound as defined in (1), wherein R is a hydrogen atom, $R^1$ is a straight chain or branched $C_{1-6}$ alkyl group, $R^2$ is a group represented by the formula: (3), and R4 is a carbamoyl group optionally having substituents, (5) A compound as defined in (1), wherein R is a hydrogen atom or a trityl group, $R^1$ is a straight chain or branched $C_{1-6}$ alkyl group or a $C_{3-6}$ cycloalkyl group, the ring A is

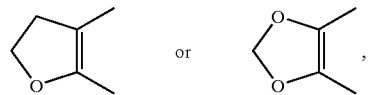

the ring B is

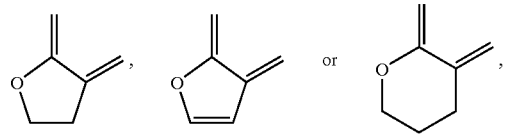

$R^3$ is a hydrogen atom, a $C_{1-4}$ alkyl group or a halogen atom, $R^4$ is (i) a $C_{6-14}$ aryl group, (ii) a 5- or 6-membered heterocyclic group which contains 1 to 4 hetero atoms selected from a nitrogen atom, an oxygen atom and a sulfur atom other than carbon atoms, (iii) a carbamoyl group, (iv) a mono- or di-$C_{1-10}$ alkyl-carbamoyl group which may be substituted by hydroxy, $C_{3-7}$ cycloalkyl or $C_{1-6}$ alkoxy-carbonyl, (v) a mono- or di-$C_{3-7}$ cycloalkyl-carbamoyl group, (vi) a mono- or di-$C_{6-14}$ aryl carbamoyl group, (vii) a mono- or di-$C_{7-16}$ aralkyl carbamoyl group, (viii) a 3- to 7-membered cyclic amino-carbonyl group, (ix) a 5- or 6-membered heterocyclic-carbamoyl group which contains 1 to 4 hetero atoms selected from a nitrogen atom, an oxygen atom and a sulfur atom other than carbon atoms, (x) a $C_{1-6}$ alkoxy-carbamoyl group, $R^5$ is a hydrogen atom or a $C_{1-4}$ alkyl group, (6) A compound as defined in (1), wherein R is a hydrogen atom, $R^1$ is a straight chain or branched $C_{1-6}$ alkyl group, $R^2$ is a group represented by the formula (3), $R^3$ is a hydrogen atom, $R^4$ is a mono- or di-$C_{1-10}$ alkyl-carbamoyl group or a $C_{3-7}$ cycloalkyl-carbamoyl group and $R^5$ is a hydrogen atom, (7) A compound as defined in (1), which is (i) 6-[1-hydroxy-1-(1H-imidazol-4-yl)-2-methylpropyl]-N-methyl-2-naphthamide, (ii) 6-[1-hydroxy-1-(1H-imidazol-4-yl)-2-methylpropyl]-N-isopropyl-2-naphthamide, (iii) N-cyclopropyl-6-[1-hydroxy-1-(1H-imidazol-4-yl)-2-methylpropyl]-2-naphthamide, (iv) 6-[1-hydroxy-1-(1H-imidazol-4-yl)propyl]-N-methyl-2-naphthamide, (v) 6-[1-hydroxy-1-(1H-imidazol-4-yl)-3-methylbutyl]-N-methyl-2-naphthamide, (vi) (S)-(−)-6-[1-hydroxy-1-(1H-imidazol-4-yl)-2-methylpropyl]-N-methyl-2-naphthamide, (vii) (S)-(−)-N-cyclopropyl-6-[1-hydroxy-1-(1H-imidazol-4-yl)-2-methylpropyl]-2-naphthamide, (viii) (S)-(−)-6-[1-hydroxy-1-(1H-imidazol-4-yl)-2-methylpropyl]-N-isopropyl-2-naphthamide, (ix) (S)-(−)-6-[1-hydroxy-1-(1H-imidazol-4-yl)propyl]-N-methyl-2-naphthamide, (x) (S)-(−)-6-[1-hydroxy-1-(1H-imidazol-4-yl)propyl]-N-methyl-2-naphthamide-fumarate, or a salt thereof, (8) A compound as defined in (1), wherein the configuration of the carbon which connects to the hydroxy group is (S)-configuration, (9) A pro-drug of the compound as defined in (1),

(10) A pharmaceutical composition which comprises a compound of the formula:

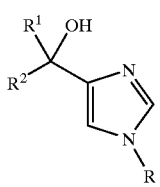

(I)

wherein R is a hydrogen atom or a protecting group, $R^1$ is a lower alkyl group or a cyclic alkyl group, $R^2$ is a group represented by the formula:

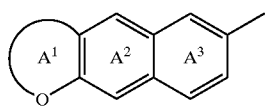

(1)

(wherein a ring $A^1$ is a 5- or 6-membered ring containing an oxygen atom optionally having substituents, and a ring $A^2$ and a ring $A^3$ may have substituents), a group represented by the formula:

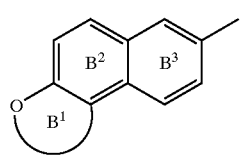

(2)

(wherein the ring $B^1$ is a 5- or 6-membered ring containing an oxygen atom optionally having substituents and a ring $B^2$ and a ring $B^3$ may have substituents) or a group of the formula:

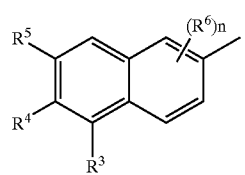

(3)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3.), or a salt thereof, or a pro-drug thereof,

(11) The pharmaceutical composition as defined in (10), which is a steroid $C_{17,20}$-lyase inhibitor,

(12) The composition as defined in (10), which is an antitumor agent,

(13) The composition for an antitumor agent as defined in (10), which is a treating or preventing agent for breast cancer or prostate cancer,

(14) An androgen reducer which combines a compound of the formula:

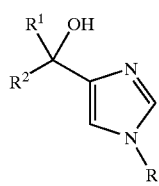

(I)

wherein R is a hydrogen atom or a protecting group, $R^1$ is a lower alkyl group or a cyclic alkyl group, $R^2$ is a group represented by the formula:

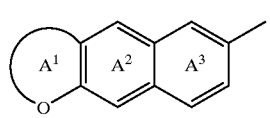

(1)

(wherein a ring $A^1$ is a 5- or 6-membered ring containing an oxygen atom optionally having substituents, and a ring $A^2$ and a ring $A^3$ may have substituents), a group represented by the formula:

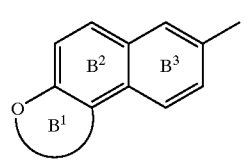

(2)

(wherein the ring $B^1$ is a 5- or 6-membered ring containing an oxygen atom optionally having substituents and a ring $B^2$ and a ring $B^3$ may have substituents) or a group of the formula:

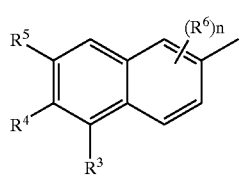

(3)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3.), or a salt thereof, or a pro-drug thereof with a LH-RH modulator,

(15) A process for producing a compound of the formula:

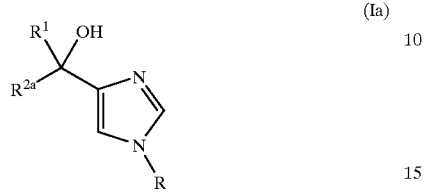

(Ia)

wherein $R^1$ is a lower alkyl group or a cyclic alkyl group, $R^{2a}$ is a group of the formula:

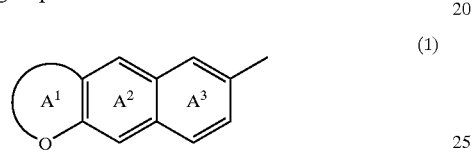

(1)

(wherein a ring $A^1$ is a 5- or 6-membered ring containing an oxygen atom optionally having substituents, and a ring $A^2$ and a ring $A^3$ may have substituents), a group represented by the formula:

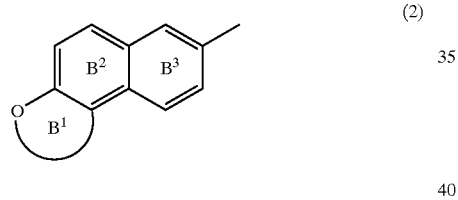

(2)

(wherein the ring $B^1$ is a 5- or 6-membered ring containing an oxygen atom optionally having substituents and a ring $B^2$ and a ring $B^3$ may have substituents) or a group of the formula:

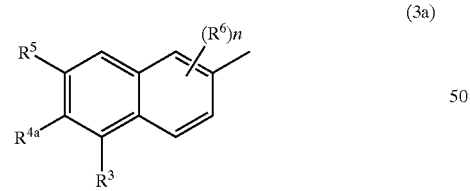

(3a)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^{4a}$ is a lower alkyl group optionally having substituents, a hydroxyl group optionally having substituents, a thiol group optionally having substituents, an amino group optionally having substituents, an acyl group, an aromatic hydrocarbon group optionally having substituents, a heterocyclic group optionally having substituents, a carbamoyl group optionally having substituents or halogen atom, $R^6$ is an optionally halogenated lower alkyl group and n is an integer of 0 to 3), and R is a hydrogen atom or a protecting group, or a salt thereof, which comprises reacting a compound of the formula:

(IIa)

wherein $R^1$ and $R^{2a}$ have the meanings given above, or a salt thereof with a reaction product of a compound of the formula:

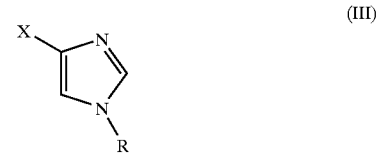

(III)

wherein X is a leaving group and R has the meaning given above,

(16) A method for inhibiting a steroid $C_{17,20}$-lyase which comprises administering a compound of the formula:

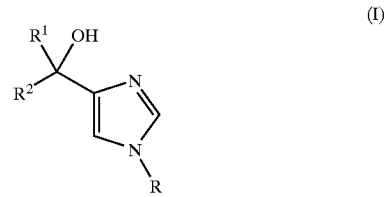

(I)

wherein R is a hydrogen atom or a protecting group, $R^1$ is a lower alkyl group or a cyclic alkyl group, $R^2$ is a group represented by the formula:

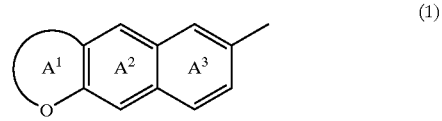

(1)

(wherein a ring $A^1$ is a 5- or 6-membered ring containing an oxygen atom optionally having substituents, and a ring $A^2$ and a ring $A^3$ may have substituents), a group represented by the formula:

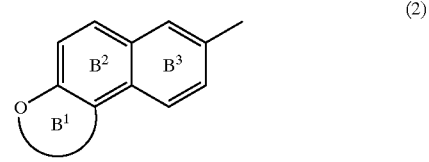

(2)

(wherein the ring $B^1$ is a 5- or 6-membered ring containing an oxygen atom optionally having substituents and a ring $B^2$ and a ring $B^3$ may have substituents) or a group of the formula:

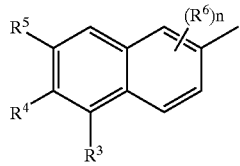

(3)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3.), or a salt thereof, or a pro-drug thereof to mammals, and

(17) Use of a compound represented by the formula:

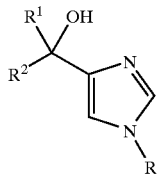

(I)

wherein R is a hydrogen atom or a protecting group, $R^1$ is a lower alkyl group or a cyclic alkyl group, $R^2$ is a group represented by the formula:

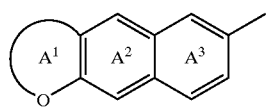

(1)

(wherein a ring $A^1$ is a 5- or 6-membered ring containing an oxygen atom optionally having substituents, and a ring $A^2$ and a ring $A^3$ may have substituents), a group represented by the formula:

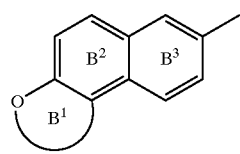

(2)

(wherein the ring $B^1$ is a 5- or 6-membered ring containing an oxygen atom optionally having substituents and a ring $B^2$ and a ring $B^3$ may have substituents) or a group of the formula:

(3)

(wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3.), or a salt thereof, or a pro-drug thereof for preparing a pharmaceutical composition for inhibiting a steroid $C_{17,20}$-lyase.

DETAILED DESCRIPTION

Figure 1:
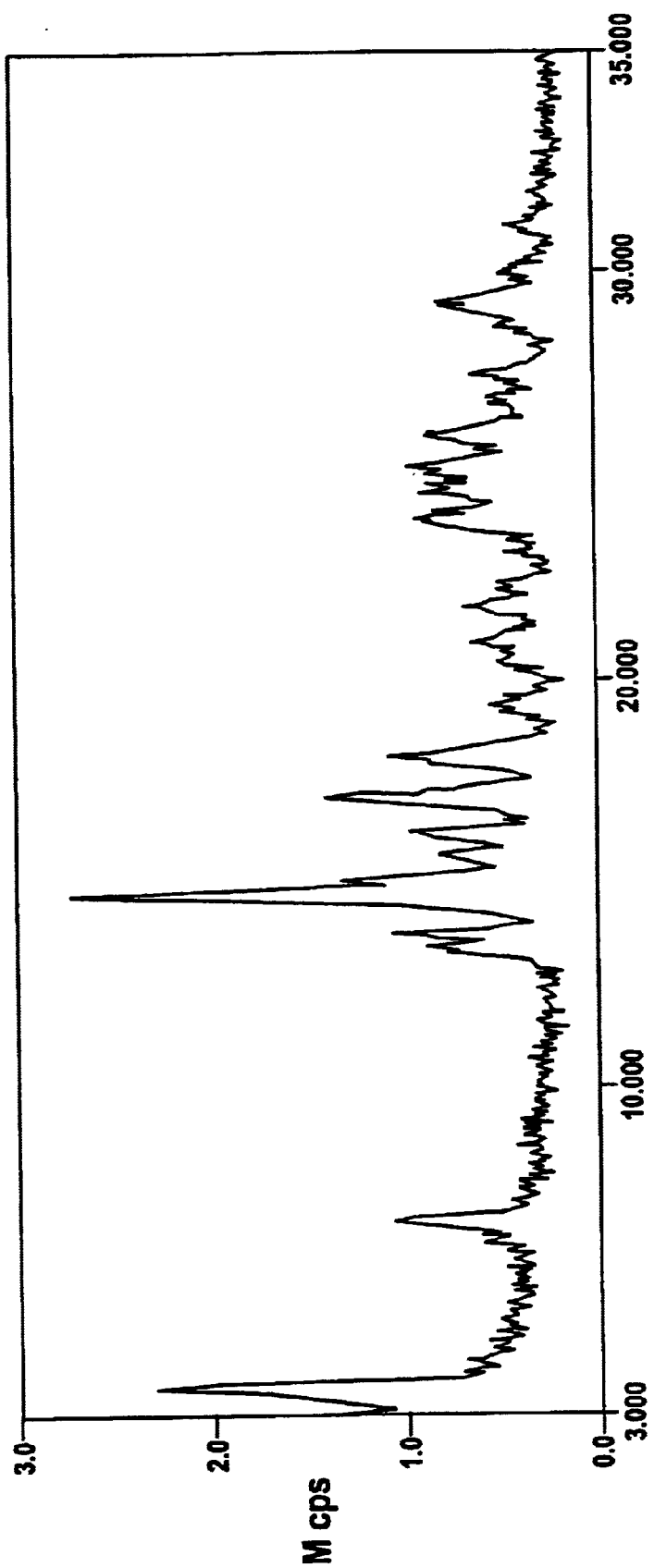
FIG. 1 shows powder X-ray diffraction spectrum (Cu, 40 kv, 50 mA) of compound produced in Example 23. Transverse axis shows angle of diffraction (2θ), and ordinate axis shows peak strength.

The lower alkyl group represented by $R^1$ is a straight chain or branched one having 1 to 6 carbon atoms, and examples of the embodiment include a $C_{1-6}$ alkyl group such as methyl, ethyl, n-propyl, isopropyl, butyl, isobutyl, sec-butyl, tert-butyl, n-pentyl, isopentyl, neopentyl, n-hexyl, isohexyl, etc., etc. Examples of the cycloalkyl group include, for example, a $C_{3-6}$ cycloalkyl group such as cyclopropyl, cyclobutyl, cyclopentyl, cyclohexyl, etc. As $R^1$, a $C_{1-4}$ alkyl group such as methyl, ethyl, n-propyl, isopropyl, n-butyl, iso-butyl, sec-butyl, tert-butyl, etc., is preferable.

In the formulas (1) and (2) represented by $R^2$ or $R^{2a}$, while each of the ring $A^1$ or the ring $B^1$ is a 5- or 6-membered ring containing an oxygen atom together with carbon atoms as ring constituting atoms, each of the rings may further contain a nitrogen atom and a sulfur atom as the ring constituting atoms.

Examples of the ring $A^1$ or the ring $B^1$ include, for example, furan, dihydrofuran, pyran, dihydropyran, dioxolene, oxazole, isooxazole, etc., and furan, dihydrofuran, dioxolene, etc. are preferable.

The ring $A^1$ and the ring $B^1$ may have 1 to 4 substituents at any substitutable position on the ring, respectively. As the substituent, there may be mentioned a lower alkyl group optionally having substituents, a lower alkoxy group, an acyl group, etc. Examples of the lower alkyl optionally having substituents include an unsubstituted $C_{1-4}$ alkyl group such as methyl, ethyl, propyl, etc., and an $C_{1-4}$ alkyl group substituted by an $C_{1-4}$ alkanoyl such as acetyl, propionyl, etc., carboxyl, a $C_{1-4}$ alkoxy-carbonyl (e.g. methoxycarbonyl, ethoxycarbonyl, butoxycarbonyl, etc.), etc. As the lower alkoxy group, there may be mentioned, for example, a $C_{1-3}$ alkoxy group such as methoxy, ethoxy, propoxy, isopropoxy, etc. As the acyl group, there may be mentioned, for example, an alkanoyl group (e.g. such a $C_{1-6}$ alkanoyl as formyl, acetyl, propionyl, etc.), an alkylsulfonyl group (e.g. such a $C_{1-4}$ alkylsulfonyl as methylsulfonyl, ethylsulfonyl, etc.), a carbamoyl group optionally having substituents (e.g. such a mono- or di-$C_{1-10}$ alkyl carbamoyl group as methylcarbamoyl, ethylcarbamoyl, dimethylcarbamoyl, diethylcarbamoyl, etc., such a mono- or di-$C_{6-14}$ arylcarbamoyl as phenylcarbamoyl, diphenylcarbamoyl, etc., such a mono- or di-$C_{7-16}$ aralkylcarbamoyl group as benzylcarbamoyl, dibenzylcarbamoyl, etc.), a sulfamoyl optionally having substituents (e.g. such a mono- or di-$C_{1-10}$ alkyl sulfamoyl group as methylsulfamoyl, ethylsulfamoyl, dimethylsulfamoyl, diethylsulfamoyl, etc., such a mono- or di-$C_{6-14}$ arylsulfamoyl group as phenylsulfamoyl, diphenylsulfamoyl, etc., such a mono- or di-$C_{7-16}$ aralkyl sulfamoyl group as benzylsulfamoyl, dibenzylsulfamoyl, etc.), etc.

The ring $A^2$, the ring $A^3$, the ring $B^2$ and the ring $B^3$ may have 1 to 3 substituents at any substitutable position on the ring, respectively. As the substituent, the same those with the substituents for the ring $A^1$ and the ring $B^1$ are used.

Examples of the lower alkyl group optionally having substituents represented by $R^3$, $R^{4a}$ and $R^5$ include, for example, an unsubstituted $C_{1-4}$ alkyl, such as methyl, ethyl, propyl, etc., a $C_{1-4}$ alkyl substituted by an alkanoyl such as acetyl, propionyl, etc., carboxyl, a $C_{1-4}$ alkoxy-carbonyl (e.g., methoxycarbonyl, ethoxycarbonyl, butoxycarbonyl, etc.), etc.

Examples of the hydroxy group optionally having substituents shown by $R^3$, $R^{4a}$, or $R^5$, include an unsubstituted hydroxy group, a lower alkoxy (e.g. a $C_{1-4}$ alkoxy group such as methoxy, ethoxy, propoxy, etc.), a lower alkanoyloxy (e.g. a $C_{1-4}$ alkanoyloxy such as acetyloxy, propionyloxy, etc.), a carbamoyloxy optionally having substituents (e.g. unsubstituted carbamoyloxy, a carbamoyloxy substituted by 1 or 2 of $C_{1-4}$ alkyl groups such as methylcarbamoyloxy, ethylcarbamoyloxy, dimethylcarbamoyloxy, diethylcarbamoyloxy, methylethylcarbamoyloxy, etc.), etc.

Examples of the thiol group optionally having substituents shown by $R^3$, $R^{4a}$ or $R^5$ include an unsubstituted thiol group, a lower alkylthio (e.g. a $C_{1-4}$ alkylthio group such as methylthio, ethylthio, propylthio, etc.), a lower alkanoylthio (e.g. a $C_{1-4}$ alkanoylthio such as acetylthio, propionylthio, etc.), etc.

Examples of the amino group optionally having substituents shown by $R^3$, $R^{4a}$ or $R^5$ include an unsubstituted amino group, a lower alkylamino (e.g. a $C_{1-4}$ alkyl amino group such as methylamino, ethylamino, propylamino, etc.), a di-lower alkylamino (e.g. a di-$C_{1-4}$ alkylamino such as dimethylamino, diethylamino, etc.), a $C_{1-4}$ alkanoylamino (e.g. acetamide, propionamide, etc.), and the like.

Examples of the acyl group represented by $R^3$, $R^{4a}$ or $R^5$ include, for example, an alkanoyl group (e.g. formyl, a $C_{1-6}$ alkanoyl such as acetyl, propionyl, etc.), an alkylsulfonyl group (e.g. a $C_{1-4}$ alkylsulfonyl such as methylsulfonyl, ethylsulfonyl, etc.), a carbamoyl group optionally having substituents (a mono- or di-$C_{1-10}$ alkyl carbamoyl group such as methylcarbamoyl, ethylcarbamoyl, dimethylcarbamoyl, diethylcarbamoyl, etc., a mono-di-$C_{6-14}$ arylcarbamoyl group such as phenylcarbamoyl, diphenylcarbamoyl, etc., a mono-di-$C_{7-16}$ aralkyl carbamoyl group such as benzylcarbamoyl, dibenzylcarbamoyl, etc.), a sulfamoyl group optionally having substituents (a mono- or di-$C_{1-10}$ alkylsulfamoyl group such as methylsulfamoyl, ethylsulfamoyl, dimethylsulfamoyl, diethylsulfamoyl, etc., a mono- or di-$C_{6-14}$ arylsulfamoyl group such as phenylsulfamoyl, diphenylsulfamoyl, etc., a mono- or di-$C_{7-16}$ aralkyl sulfamoyl group such as benzylsulfamoyl, dibenzylsulfamoyl, etc.), and the like.

Examples of the halogen shown by $R^3$, $R^{4a}$ or $R^5$ include fluorine, chlorine, bromine, iodine.

Examples of the aromatic hydrocarbon group in "aromatic hydrocarbon group optionally having substituents" represented by $R^4$ include a monocyclic aromatic hydrocarbon group, a condensed polycyclic aromatic hydrocarbon group, etc., each of which is constituted with 6 to 18 carbon atoms. Examples of the embodiment include a $C_{6-14}$aryl group such as phenyl, 1-naphthyl, 2-naphthyl, 2-indenyl, 2-anthryl, etc. Among them, a $C_{6-10}$ aryl group (for example, phenyl, etc.) is preferable.

Examples of the heterocyclic group in "a heterocyclic group optionally having substituents" represented by $R^4$ include, for example, a 3- to 13-membered, preferably 5- to 9-membered, more preferably 5- or 6-membered heterocyclic group (e.g. aromatic heterocyclic group, non-aromatic heterocyclic group) which contains 1 to 4 hetero atoms selected from a nitrogen atom, an oxygen atom, a sulfur atom, etc. other than carbon atoms and the like. Specifically, as the aromatic heterocyclic group, for example, thienyl (e.g. 2-thienyl, 3-thienyl), pyridyl, (e.g. 2-pyridyl, 3-pyridyl, 4-pyridyl), furyl (e.g. 2-furyl, 3-furyl), quinolyl (e.g. 2-quinolyl, 4-quinolyl, 8-quinolyl), isoquinolyl (e.g. 3-isoquinolyl, 4-isoquinolyl), pyrazinyl, pyrimidinyl (e.g. 2-pyrimidinyl), pyrrolyl (e.g. 3-pyrrolyl), imidazolyl (e.g. 1-imidazolyl, 2-imidazolyl), pyrazolyl (e.g. 1-pyrazolyl), thiazolyl (e.g. 2-thiazolyl, 4-thiazolyl, 5-thiazolyl), isothiazolyl (e.g. 3-isothiazolyl, 4-isothiazolyl), oxazolyl (e.g. 2-oxazolyl, 4-oxazolyl, 5-oxazolyl), isoxazolyl (e.g. 3-isoxazolyl), pyridazinyl (e.g. 3-pyridazinyl), indolyl (e.g. 1-indolyl), isoindolyl (e.g. 1-isoindolyl, 2-isoindolyl), tetrazolyl (e.g. 1-tetrazolyl, 2-tetrazolyl, 5-tetrazolyl), etc.), etc. are used, and as the non-aromatic heterocyclic group, for example, 1-pyrrolidyl, 1-piperidyl, 4,5-dihydro-1,3-oxazol-2-yl, etc. are used. Among them, preferable examples are thienyl, furyl, oxazolyl, isoxazolyl, imidazolyl, triazolyl, 4,5-dihydro-1,3-oxazol-2-yl, and the like.

In the "heterocyclic group optionally having substituents" and "aromatic hydrocarbon group" represented by $R^4$, 1 to 3 substituents may substitute at any position on the ring. As the substituent, there may be mentioned a lower alkyl group optionally having substituents, a lower alkoxy group, an acyl group, etc. Examples of the lower alkyl optionally having substituents include an unsubstituted $C_{1-4}$ alkyl group such as methyl, ethyl, propyl, etc., and an $C_{1-4}$ alkyl group substituted by an $C_{1-4}$ alkanoyl such as acetyl, propionyl, etc., carboxyl, a $C_{1-4}$ alkoxy-carbonyl (e.g. methoxycarbonyl, ethoxycarbonyl, butoxycarbonyl, etc.), etc. As the lower alkoxy group, there may be mentioned, for example, a $C_{1-3}$ alkoxy group such as methoxy, ethoxy, propoxy, isopropoxy, etc. As the acyl group, there may be mentioned, for example, an alkanoyl group (e.g. such a $C_{1-6}$ alkanoyl as formyl, acetyl, propionyl, etc.), an alkylsulfonyl group (e.g. such a $C_{1-4}$ alkylsulfonyl as methylsulfonyl, ethylsulfonyl, etc.), a carbamoyl group optionally having substituents (e.g. such a mono- or di-$C_{1-10}$ alkyl carbamoyl group as methylcarbamoyl, ethylcarbamoyl, dimethylcarbamoyl, diethylcarbamoyl, etc., such a mono- or di-$C_{6-14}$ arylcarbamoyl as phenylcarbamoyl, diphenylcarbamoyl, etc., such a mono- or di-$C_{7-16}$ aralkylcarbamoyl group as benzylcarbamoyl, dibenzylcarbamoyl, etc.), a sulfamoyl optionally having substituents (e.g. such a mono- or di-$C_{1-10}$ alkyl sulfamoyl group as methylsulfamoyl, ethylsulfamoyl, dimethylsulfamoyl, diethylsulfamoyl, etc., such a mono- or di-$C_{6-14}$ arylsulfamoyl group as phenylsulfamoyl, diphenylsulfamoyl, etc., such a mono- or di-$C_{7-16}$ aralkyl sulfamoyl group as benzylsulfamoyl, dibenzylsulfamoyl, etc.), etc.

Examples of the "carbamoyl group optionally having substituents" represented by $R^4$ include
(1) a carbamoyl group,
(2) a mono- or di-alkyl carbamoyl group (e.g. a mono- or di-$C_{1-10}$ alkyl carbamoyl group) such as methyl carbamoyl, ethyl carbamoyl, dimethyl carbamoyl, etc.,
(3) a mono- or di-cycloalkyl carbamoyl group (e.g. a mono- or di-$C_{3-7}$ cycloalkyl carbamoyl group) such as cyclopropyl carbamoyl, cyclobutyl carbamoyl, cyclopentyl carbamoyl, cyclohexyl carbamoyl, cycloheptyl carbamoyl, etc.,
(4) an aryl carbamoyl group (e.g. a $C_{6-14}$ aryl carbamoyl group) such as phenyl carbamoyl,
(5) an aralkyl carbamoyl group (e.g. a $C_{7-16}$ aralkyl carbamoyl group) such as benzyl carbamoyl,
(6) a 3- to 7-membered, preferably 5-membered cyclic amino-carbonyl group,
(7) a 5- or 6-membered heterocyclic-carbamoyl group which contains 1 to 4 hetero atoms selected from a nitrogen atom, an oxygen atom, a sulfur atom, etc. other than carbon atoms such as thiazolyl (e.g. 2-thiazolyl), pyridyl, pyrimidazyl, furyl, thienyl, oxazolyl, isooxazolyl, imidazolyl, etc.,
(8) an alkoxy carbamoyl group (e.g. a $C_{1-6}$ alkoxy carbamoyl group) such as methoxy carbamoyl, etc., and a lower alkyl carbamoyl group (e.g. a $C_{1-6}$ alkyl carbamoyl group) such as methyl carbamoyl, ethyl carbamoyl, etc. is preferable.

These carbamoyl groups may have 1 to 3 substituents may substitute at any position on the ring. As the substituent, there may be mentioned hydroxy, halogen atom (e.g. fluoro, chloro), $C_{1-6}$ alkyl (e.g. methyl, ethyl), $C_{3-7}$ cycloalkyl (e.g. cyclopropyl, cyclobutyl, cyclopentyl, cyclohexyl), $C_{1-6}$ alkoxy (e.g. methoxy, ethoxy), $C_{1-6}$ acyl (e.g. formyl, acetyl, ethylcarbonyl), carboxy, $C_{1-6}$ alkoxy-carbonyl (e.g. methoxycarbonyl, ethoxycarbonyl) and the like.

As the optionally halogenated lower alkyl group represented by $R^6$, for example, a $C_{1-6}$ alkyl group (e.g. methyl, ethyl, propyl, I-propyl, butyl, sec-butyl, tert-butyl) optionally having 1 to 5, preferably 1 to 3 halogen atoms such as fluorine, chlorine, bromine, iodine, and the like are used, and a $C_{1-3}$ alkyl group (e.g. methyl, ethyl, propyl) optionally having 1 to 5, preferably 1 to 3 halogen atoms such as fluorine, chlorine, bromine, iodine, and the like are preferable, and particularly methyl, ethyl, trifluoromethyl, etc. are used, n represents a integer of 0 to 3, and this means 0 to 3 substituents:R may substitute. As n, 0, 1 or 2 is preferable.

Examples of the protecting group represented by R include for example, formyl, a $C_{1-6}$ alkyl-carbonyl (for example, acetyl, propionyl, etc.), phenyl-carbonyl, a $C_{1-6}$ alkyl-oxycarbonyl (for example, methoxycarbonyl, ethoxycarbonyl, etc.), allyl-oxycarbonyl, phenyloxycarbonyl, a $C_{7-10}$ aralkyl-oxy-carbonyl (for example, a phenyl-$C_{1-4}$ alkyl-oxy-carbonyl such as benzyloxycarbonyl, etc.), trityl, N,N-dimethylaminosulfonyl, $C_{7-16}$ aralkyl-oxy-$C_{1-6}$ alkyl (e.g. benzyl-oxy-methyl, etc.) each of which may be substituted, and trityl is preferable. Examples of the substituent of the protecting group include a halogen atom (for example, fluorine, chlorine, bromine, iodine, etc.), a $C_{1-6}$ alkyl-carbonyl (for example, acetyl, propionyl, valeryl, etc.), a nitro group, and number of these substituents is 1 to 3.

Examples of the leaving group represented by X include a halogen atom (chlorine, bromine, iodine, etc.), an alkyl or aryl-sulfonyloxy group (methanesulfonyloxy, ethanesulfonyloxy, benzenesulfonyloxy, p-toluenesulfonyloxy, etc.), etc.

As the compound represented by the formula (I) of the present invention, for example, the following compounds are preferable.
(A) The compound (I) wherein R is a hydrogen atom, $R^1$ is a straight chain or branched $C_{1-4}$ alkyl group (e.g. methyl, ethyl, isopropyl, butyl, sec-butyl, tert-butyl), $R^2$ is a group represented by the formula (3), $R^4$ is a carbamoyl group optionally having substituents.
(B) The compound (I) wherein R is a hydrogen atom or a trityl group, $R^1$ is a straight chain or branched $C_{1-6}$ alkyl group (e.g. methyl, ethyl, isopropyl, butyl, isobutyl, sec-butyl, tert-butyl) or a $C_{3-6}$ cycloalkyl group (e.g. cyclopropyl, cyclobutyl, cyclopentyl, cyclohexyl), the ring A is

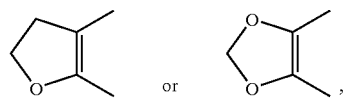

the ring B is

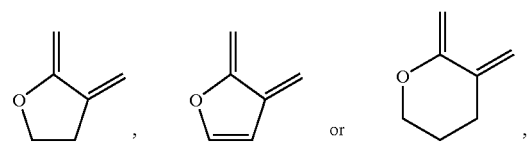

$R^3$ is a hydrogen atom, a $C_{1-4}$ alkyl group or a halogen atom,
$R^4$ is
(1) a $C_{6-14}$ aryl group (e.g. phenyl, naphthyl),
(2) a 5- or 6-membered heterocyclic group which contains 1 to 4 hetero atoms selected from a nitrogen atom, an oxygen atom and a sulfur atom other than carbon atoms (e.g. thiazolyl, pyridyl, pyrimidazyl, furyl, thienyl, oxazolyl, isooxazolyl, imidazolyl, triazolyl, 4,5-dihydro-1,3-oxazol-2-yl, etc.).
(3) a carbamoyl group,
(4) a mono-or di-$C_{1-10}$ alkyl-carbamoyl group (particularly, a mono- or di-$C_{1-6}$ alkyl carbamoyl group) which may be substituted by hydroxy, $C_{3-7}$ cycloalkyl or $C_{1-6}$ alkoxy-carbonyl,
(5) a mono- or di-$C_{3-7}$ cycloalkyl-carbamoyl group,
(6) a mono- or di-$C_{6-14}$ aryl carbamoyl group (e.g. mono- or di-phenyl group),
(7) a $C_{7-16}$ aralkylcarbamoyl group (e.g. a benzyl carbamoyl group),
(8) a 3- to 7-membered cyclic amino-carbonyl group,
(9) a 5- or 6-membered heterocyclic-carbamoyl group which contains 1 to 4 hetero atoms selected from a nitrogen atom, an oxygen atom, a sulfur atom, etc. other than carbon atoms (e.g. thiazolyl),
(10) a $C_{1-6}$ alkoxy-carbamoyl group (particularly, a $C_{1-3}$ alkoxy carbamoyl group),
$R^5$ is a hydrogen atom or a $C_{1-4}$ alkyl group.
(C) The compound (I) wherein R is a hydrogen atom, $R^1$ is a straight chain or branched $C_{1-6}$ alkyl group (particularly, methyl, ethyl, isopropyl, butyl, isobutyl, sec-butyl), $R^2$ is a group represented by the formula (3), $R^3$ is a hydrogen atom, $R^4$ is a mono- or di-$C_{1-10}$ alkyl-carbamoyl group or a $C_{3-7}$ cycloalkyl-carbamoyl group, $R^5$ is a hydrogen atom.

(D) The compound produced in Examples 1 to 54 described below.

(E) (i) 6-[1-hydroxy-1-(1H-imidazol-4-yl)-2-methylpropyl]-N-methyl-2-naphthamide (Example 9-(ii)), (ii) 6-[1-hydroxy-1-(1H-imidazol-4-yl)-2-methylpropyl]-N-isopropyl-2-naphthamide (Example 26), (iii) N-cyclopropyl-6-[1-hydroxy-1-(1H-imidazol-4-yl)-2-methylpropyl]-2-naphthamide (Example 28), (iv) 6-[1-hydroxy-1-(1H-imidazol-4-yl)propyl]-N-methyl-2-naphthamide (Example 51), (v) 6-[1-hydroxy-1-(1H-imidazol-4-yl)-3-methylbutyl]-N-methyl-2-naphthamide (Example 54), (vi) (S)-(−)-6-[1-hydroxy-1-(1H-imidazol-4-yl)-2-methylpropyl]-N-methyl-2-naphthamide (Example 55), (vii) (S)-(−)-N-cyclopropyl-6-[1-hydroxy-1-(1H-imidazol-4-yl)-2-methylpropyl]-2-naphthamide (Example 57), (viii) (S)-(−)-6-[1-hydroxy-1-(1H-imidazol-4-yl)-2-methylpropyl]-N-isopropyl-2-naphthamide (Example 58), (ix) (S)-(−)-6-[1-hydroxy-1-(1H-imidazol-4-yl)propyl]-N-methyl-2-naphthamide (Example 65-(i)), (x) (S)-(−)-6-[1-hydroxy-1-(1H-imidazol-4-yl)propyl]-N-methyl-2-naphthamide-fumarate (Example 65-(ii)), or a salt thereof.

The compound of the formula (I) may be a salt. Examples of the salt include a salt of inorganic acid (for example, a hydrochloric acid salt, a sulfuric acid salt, a hydrobromic acid salt, a phosphoric acid salt, etc.), a salt of an organic acid (for example, an acetic acid salt, a trifluoroacetic acid salt, a succinic acid salt, a maleic acid salt, a fumaric acid salt, a propionic acid salt, a citric acid salt, a tartaric acid salt, a lactic acid salt, an oxalic acid salt, a methanesulfonic acid salt, a p-toluenesulfonic acid salt, etc.), etc.

The compound represented by the formula (I) or a salt thereof may be hydrated. These including the salt and hydrate are hereinafter referred to as Compound (I).

The pro-drug of Compound (I) means a compound which is converted to Compound (I) having a steroid $C_{17,20}$-lyase inhibitory activity by enzymes, gastric acid, etc. in vivo.

Examples of the pro-drug of Compound (I) include Compound (I) wherein the nitrogen atom of imidazole is substituted with acyl or alkyl, etc. (e.g. a compound wherein the nitrogen atom is substituted with dimethylaminosulfonyl, acetoxymethyl, (5-methyl-2-oxo-1,3-dioxolen-4-yl) methoxycarbonylmethyl, pivaloyloxymethyl, benzyloxymethyl, etc.); Compound (I) wherein the hydroxy group is substituted with an acyl, an alkyl, phosphoric acid, sulfuric acid, boric acid, etc. (e.g. a compound wherein an hydroxy group of is substituted with acetyl, palmitoyl, propanoyl, pivaloyl, succinyl, fumaryl, alanyl, dimethylaminomethylcarbonyl, etc.); etc. These compound can be produced by a per se known method.

The pro-drug of Compound (I) may be in the form of any pharmaceutically acceptable salts thereof.

When the pro-drug of Compound (I) has an acidic group such as a carboxyl group, examples of the salt include a salt with an inorganic base (e.g., an alkali metal such as sodium, potassium, etc.; an alkaline earth metal such as calcium, magnesium, etc.; a transition metal such as zinc, iron, copper, etc.; etc.); an organic base (e.g., an organic amine such as trimethylamine, triethylamine, pyridine, picoline, ethanolamine, diethanolamine, triethanolamine, dicyclohexylamine, N,N'-dibenzylethylenediamine, etc.; a basic amino acid such as arginine, lysine, ornithine, etc.; etc.); and the like.

When the pro-drug of Compound (I) has a basic group such as an amino group, examples of the salt include a salt with an inorganic acid or an organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); acidic amino acids such as aspartic acid, glutamic acid, etc.; and the like.

Also, the pro-drug of Compound (I) may be hydrated.

Compound (I) may have one or more asymmetric carbons in the molecule. The compound of the present invention may have R-configuration or S-configuration as to the asymmetric carbons.

As the compound (I), a compound wherein the configuration of the carbon which connects to the hydroxy group is (S)-configuration is preferable.

Throughout the specification, among the compounds shown by the formulas (I), (I'), (I'), (Ia), (II), (II')(III), (IV), (IV'), (V), (VI), (XIV), (XV) and (XVI), a compound having a basic group or an acidic group can form a salt with an acid or a salt with a base, respectively. Examples of the salt include the salt of the Compound (I) mentioned above. Hereinafter the compound of the formula (Number of formula) and its salt are referred to as Compound (Number of formula). For example, a compound of formula (II) and a salt thereof are referred to as Compound (II).

Compound (I) can be produced, for example, by the following process steps.

The starting compound and an intermediate can be used as free form or a salt thereof like Compound (I), and they are used as the reaction mixture as it is or after isolation by a known method for the following reaction.

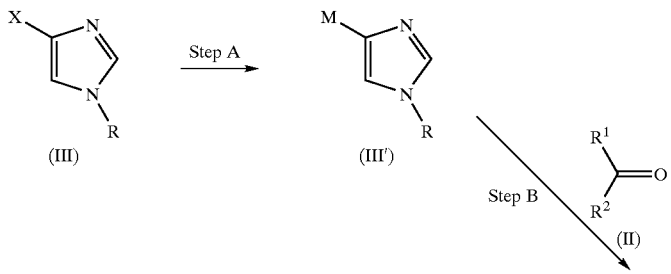

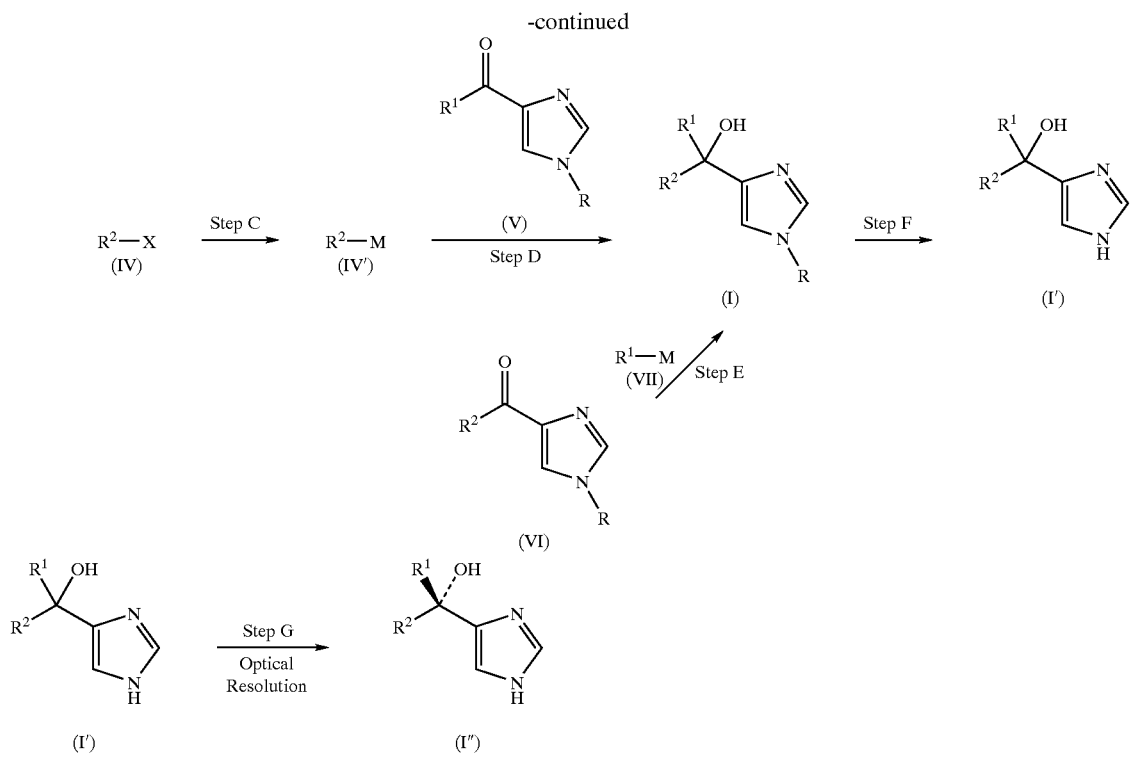

wherein M is a metal or a salt thereof, and the other symbols have the meanings as given above.

Examples of the metal shown by M include lithium or magnesium, etc. Examples of the salt of metal shown by M include, for example, a metal halide such as magnesium chloride, magnesium bromide, etc.

Processes A and B

The Compound (III) is allowed to react with an alkyl-lithium or magnesium metal, etc., to give an organometal Compound (III'). The Compound (III') is allowed to react with Compound (II) to give Compound (I). Examples of the alkyl-lithium used in the reaction include a $C_{1-4}$ alkyl-lithium such as n-butyllithium, s-butyllithium, tert-butyllithium, etc., and tert-butyllithium is preferable. The alkyl-lithium is used in an amount of 1 to 3 moles, preferably 1 to 1.5 mole per one mole of the starting material (III). The reaction temperature in case of the reaction with an alkyl-lithium is in the range of −100° C. to 0° C., preferably −80° C. to −20° C. Examples of the alkyl-magnesium halide include ethylmagnesium bromide, methylmagnesium chloride, etc., and ethylmagnesium halide is preferable. The used amount of the alkyl-magnesium halide is 1 to 10 moles, preferably 1 to 4 moles per mole of the starting Compound (III). The temperature in case of the reaction with magnesium metal is in the range of −40° C. to 60° C., preferably 20° C. to 40° C. The reaction time is about 5 min to 20 h. The reaction is usually carried out in the presence of an organic solvent which does not affect to the reaction. Examples of the organic solvent which does not affect to the reaction include, for example, an ether such as diethyl ether, dioxane, tetrahydrofuran (THF), etc., a saturated hydrocarbon such as hexane, pentane, etc., a halogenated hydrocarbon such as dichloromethane, chloroform, etc., an aromatic hydrocarbon such as benzene, toluene, etc. These solvent may be used solely or in combination of two or more in an appropriate ratio. The Compound (II) is used in 0.1 to 10 equivalents, preferably 0.2 to 2 equivalents relative to one equivalent of Compound (III).

Processes C and D

The Compound (IV) is allowed to react with an alkyl-lithium or magnesium metal, etc., to give an organometal Compound (IV'). The Compound (IV') is allowed to react with Compound (V) to give Compound (I). Examples of the alkyl-lithium used include a $C_{1-4}$ alkyl-lithium such as n-butyllithium, sec-butyllithium, tert-butyllithium, etc. The alkyl-lithium is used in an amount of 1 to 3 moles, preferably 1 to 1.5 mole per one mole of Compound (IV). The reaction temperature in case of the reaction with an alkyl-lithium is in the range of −100° C. to 0° C., preferably −80° C. to −20° C. The reaction time is about 5 minutes to 20 hours. In case that Compound (IV) is reacted with magnesium metal, the used amount of magnesium metal is in the range of 1 to 3 moles, preferably 1 to 1.5 mole per mole of Compound (IV), and the temperature is in the range of −20° C. to 100° C., preferably 10° C. to 50° C. The reaction time is about 5 min to 20 h. The reaction is usually carried out in the presence of an organic solvent which does not affect to the reaction. Examples of the organic solvent which does not affect to the reaction include, for example, an ether such as diethyl ether, dioxane, tetrahydrofuran (THF), etc., a saturated hydrocarbon such as hexane, pentane, etc., a halogenated hydrocarbon such as dichloromethane, chloroform, etc., an aromatic hydrocarbon such as benzene, toluene, etc. These solvent may be used solely or in combination of two or more in an appropriate ratio. Compound (V) is used in 0.1 to 10 moles, preferably 0.5 to 1.5 mole per mole of Compound (V).

Process E

Compound (I) can be produced by reacting an organometal Compound (VI) with Compound (VII). Compound (VII) is used in an amount ranging 0.5 to 10 moles, preferably 1 to 5 moles per mole of Compound (VI). The reaction temperature ranges −80° C. to 50° C., preferably −50° C. to 20° C. The reaction is usually carried out in an organic solvent which does not have a bad influence to the reaction. Examples of the solvent include, for example, an ether such as diethyl ether, dioxane, tetrahydrofuran (THF), etc., a saturated hydrocarbon such as hexane, pentane, etc., a halogenated hydrocarbon such as dichloromethane, chloroform, etc., and an aromatic hydrocarbon such as benzene, toluene. These solvents may be used solely or in combination of more than two kinds of solvent.

Process F

Compound (I') can be produced by allowing Compound (I) wherein R is a protecting group to de-protecting reaction which is a known method or a similar manner to a known method. For example, Compound (I') can be produced by treating Compound (I) wherein R is trityl group with acidic condition or by allowing it to hydrogenolysis to remove the trityl group. Examples of the acid include an organic acid such as formic acid, acetic acid, etc., an inorganic acid such as hydrochloric acid, etc. The reaction can be carried out in an inert solvent such as an alcohol, an ether (e.g. tetrahydrofuran, etc.), etc. The reaction temperature is usually 0° C. to 100° C.

Process G

Process G is a process in which racemic Compound (I') is divided to optically active compounds (I"). Compound (I") can be obtained by allowing Compound (I') to a known optical resolution or a similar manner to a known optical resolution. Examples of the optical resolution method include a liquid chromatography method using chiral column, diastereomer salt method using an optically active acid or an optically active base, etc.

When the desired compound is obtained in free form, the compound may be converted to a salt by a conventional manner. When the desired compound is obtained in a salt, the compound can be converted to free form by a conventional manner. Compounds (I), (I') and (I") thus obtained can be isolated from the reaction mixture and purified by a known procedure such as phase transfer, concentration, solvent extraction, fractional distillation, crystallization, recrystallization, chromatography, etc.

In the above reactions, an amino group, a carboxyl group, a hydroxy group, each of which is not involved in the reaction, in the compound or a salt thereof which is to be reacted may be protected. The protection with a protecting group and deprotection can be carried out by a known manner. Examples of the protecting group of an amino group include, for example, formyl, a $C_{1-6}$alkylcarbonyl (for example, acetyl, propionyl, etc.), a phenylcarbonyl, a $C_{1-6}$ alkyl-oxycarbonyl (for example, methoxycarbonyl, ethoxycarbonyl, etc.), phenyloxycarbonyl, a $C_{7-10}$ aralkyloxy-carbonyl (for example, a phenyl-$C_{1-4}$ alkyloxy-carbonyl such as benzyloxycarbonyl, etc.), trityl, phthaloyl or N,N-dimethylaminomethylene, etc., each of which may be substituted. Examples of the substituent include a halogen atom (for example, fluorine, chlorine, bromine, iodine, etc.), formyl, a $C_{1-6}$ alkyl-carbonyl (for example, acetyl, propionyl, valeryl, etc.), nitro, etc. The number of substituent is about 1 to 3.

Examples of the protecting group of a carboxyl group include, for example, a $C_{1-6}$ alkyl (for example, methyl, ethyl, propyl, isopropyl, butyl, tert-butyl, etc.), phenyl, trityl or silyl, etc., each of which may be substituted. Examples of the substituent include, a halogen atom (for example, fluorine, chlorine, etc.), formyl, a $C_{1-6}$ alkyl-carbonyl (for example, acetyl, propionyl, valeryl, etc.), nitro, etc. The number of substituent is about 1 to 3.

Examples of the protecting group of a hydroxy group include, for example, a $C_{1-6}$alkyl (for example, methyl, ethyl, propyl, isopropyl, butyl, tert-butyl, etc.), phenyl, a $C_{7-10}$aralkyl (for example, a phenyl-$C_{1-4}$ alkyl such as benzyl, etc.), formyl, a $C_{1-6}$alkyl-carbonyl (for example, acetyl, propionyl, etc.), phenyloxycarbonyl, benzoyl, a ($C_{7-10}$aralkyloxy)carbonyl (for example, a phenyl-$C_{1-4}$ alkyloxy-carbonyl such as benzyloxycarbonyl, etc.), pyranyl, furanyl or silyl, etc., each of which may be substituted. Examples of the substituent include a halogen atom (for example, fluorine, chlorine, etc.), a $C_{1-6}$alkyl (for example, methyl, ethyl, propyl, etc.), phenyl, a $C_{7-10}$aralkyl (for example, a phenyl-$C_{1-4}$alkyl such as benzyl, etc.), nitro, etc. The number of substituent is about 1 to 4.

The deprotection reaction is carried out by a known manner or a similar manner thereof. Examples of the deprotection reaction include a manner treating with, for example, acid, base, reduction, ultraviolet ray, hydrazine, phenyl hydrazine, sodium N-methyldithiocarbamate, tetrabutylammonium fluoride, palladium acetate, etc.

Compound A can be produced, for example, by the following manner.

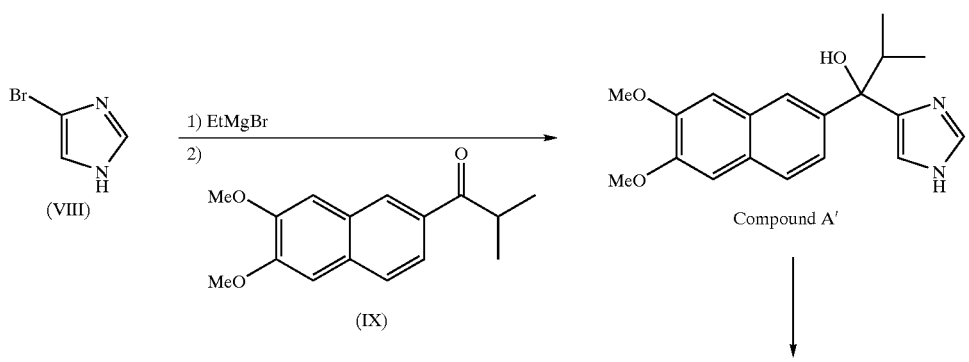

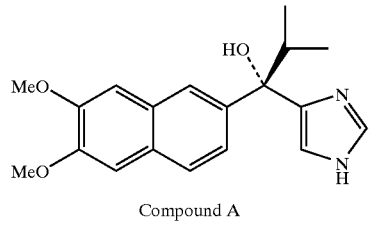

Compound A

Compound (VIII) is treated with 2 to 5 equivalents of ethylmagnesium bromide in an inert solvent (e.g., THF, diethyl ether) to give a Grignard reagent of imidazole. The obtained product with reacted with Compound (IX) in the same solvent to give Compound (A'). Compound (A') can also produced by converting Compound (VIII) to a lithium salt of the imidazole compound by treating with tert-butyllithium and then reacting the lithium salt with Compound (XI). Compound A can be obtained by allowing Compound A' to optical resolution by using chiral column (e.g., CHIRALPAK AD, manufactured by Daicel chemical Industries, Ltd.). Compound A can also be obtained by converting Compound A' to a diastereomer salt with an optically active acid, followed by utilizing the difference of solubility.

Compound B can be produced, for example, by the following manner.

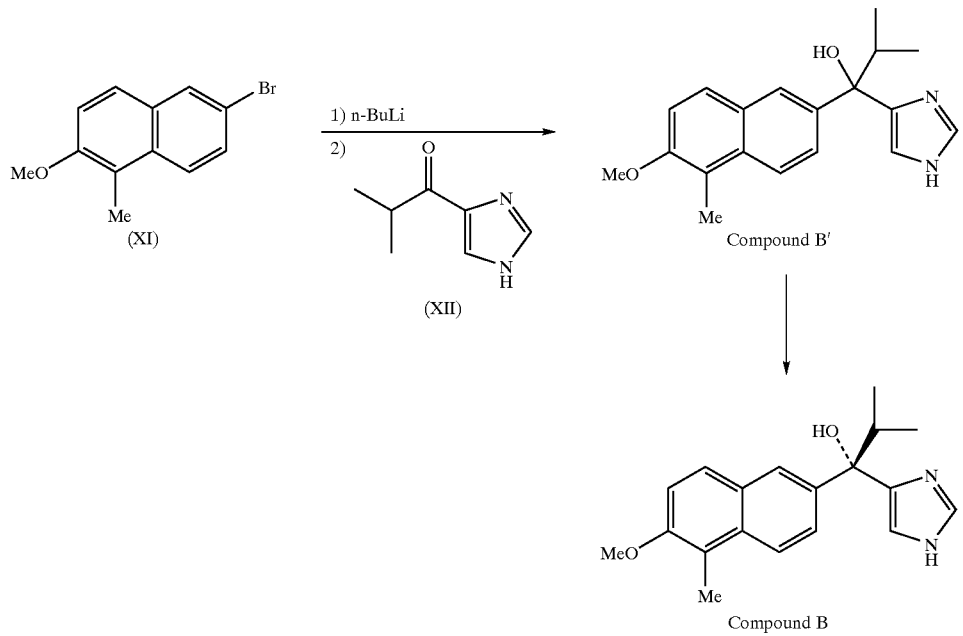

wherein n-BuLi is n-butyllithium.

Compound (XI) is reacted with an alkyl-lithium (e.g., n-butyllithium) to give a lithium salt. The lithium salt is reacted with Compound (XII) to give Compound B'. The amount of the alkyl-lithium used in the reaction is in the range of from 1 to 2 equivalent, preferably 1 to 1.5 equivalent. The reaction temperature is in the range of −80° C. to 0° C., preferably −80° C. to −20° C. As the reaction solvent, THF, etc., is preferable. Compound B can be obtained from Compound B' by a similar manner to optical resolution of Compound A'.

Compound C can, for example, be synthesized by the following method.

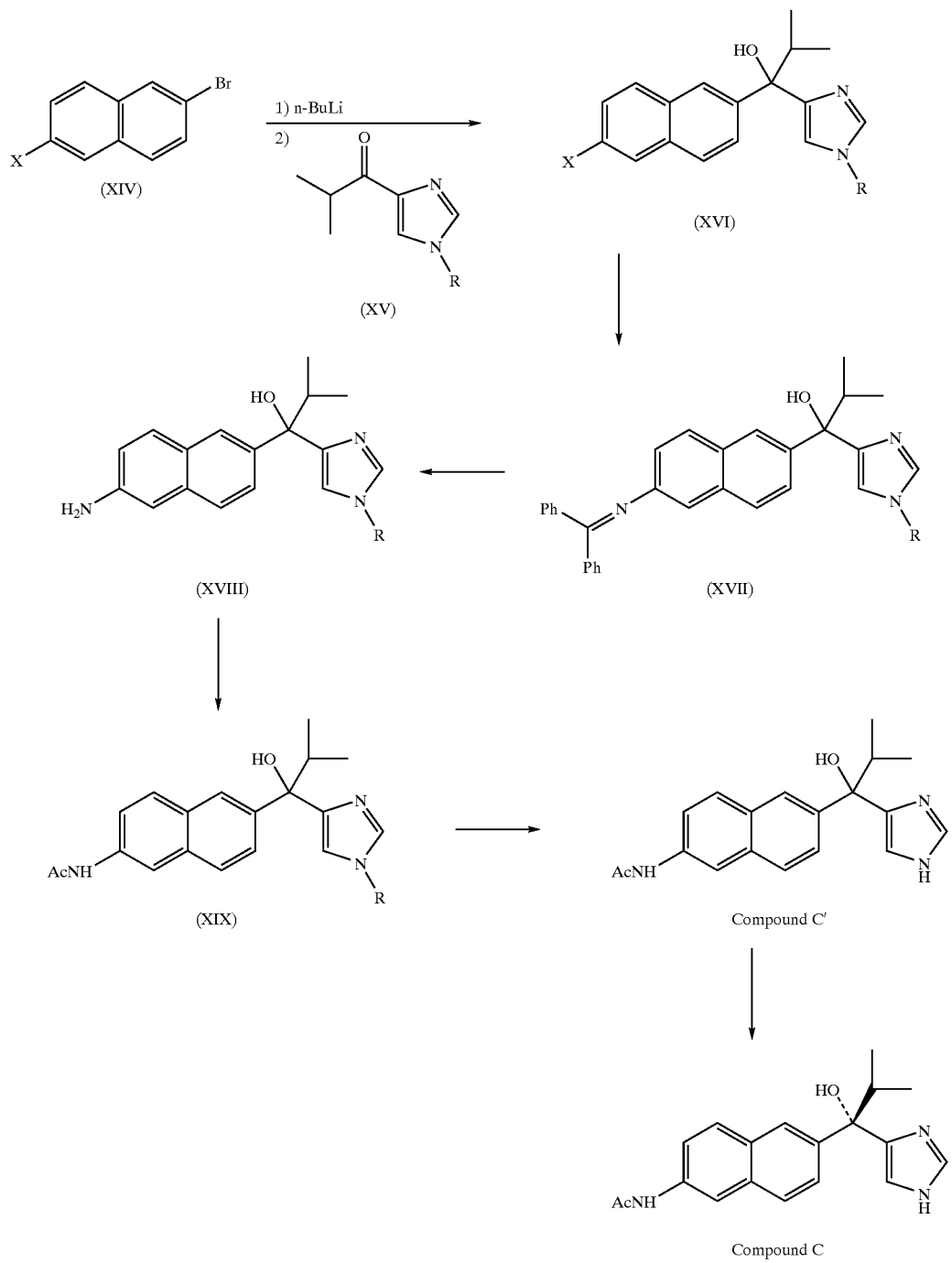

wherein Ac is an acetyl group, Ph is a phenyl group, and the other symbols have the meanings given above.

Compound (XI) is reacted with an alkyl-lithium (e.g., n-butyllithium) to give a lithium salt, and the lithium salt is reacted to Compound (XV) to give Compound (XVI). The amount of the alkyl-lithium used in the reaction is 1 to 2 equivalents, preferably 1 to 1.5 equivalent. As the solvent, THF, etc. is preferable.

Compound (XVI) can be converted to Compound (XVII) and Compound (XVIII) by a method described in a literature (Buchwald et al., Tetrahedron Letters, Vol.38, pp.6367–6370, 1997). Compound C' can be obtained by acetylated Compound (XVIII), followed by deprotecting a protective group. Compound C can be obtained from Compound C' by a similar manner to optical resolution of Compound A'.

Each of Compounds (I), A, B and C can be obtained as a stable crystals by allowing to form a salt with an acid. The salt has a solubility in water and an absorbability, each of the solubility and the absorbability is higher than that of free form. Examples of the acid include an organic acid such as fumaric acid, oxalic acid, malic acid, etc., and among them, fumaric acid is preferable.

Compounds (I), A, B and C can effectively be resolved to their enantiomers by using chiral column (e.g. CHIRALPAK AD, manufactured by Daicel Chemical Industries, Ltd.).

These compounds can also be resolved by allowing to form a diastereomer salt with an optically active acid, followed by utilizing the difference of solubility.

Compounds (I), A, B and C (hereinafter referred to as the compound of the present invention) have superior effect as medicine, and especially has a superior inhibitory activity of steroid $C_{17,20}$-lyase. The compound of the present invention is less toxic and has little adverse side effect. The compound of the present invention is useful as (i) an androgen and/or estrogen reducer, (ii) an agent for the preventing and treating various androgen- and/or estrogen-related diseases such as (1) primary cancer, metastasis or recurrence of malignant tumor (for example, prostate cancer, breast cancer, uterine cancer, ovarian cancer, etc.), (2) various symptoms accompanied with these cancer (for example, pain, cachexia, etc.), (3) prostatic hypertrophy, virilism, hirsutism, male pattern alopecia, precocious puberty, endometriosis, uterus myoma, adenomyosis of uterus, mastopathy, polycystic ovary syndrome, etc. to a mammal (for example, humans, bovines, horses, pigs, dogs, cats, monkeys, mice, rats, etc., especially humans).

While the compound of the present invention has a superior effect when used solely, the effect can be promoted by using the compound of the present invention in combination with other medicaments and remedies. Examples of the medicament and remedy, include, for example, sex hormones, alkylating agents, antimetabolites, antitumor antibiotics, plant alkaloids, immunotherapies, etc., but not limited to.

Examples of the hormone-related agent include, for example, Fosfestrol, Diethylstilbestrol, chlorotrianisene, Medroxyprogesterone acetate, Megestrol acetate, Chlormadinone acetate, Cyproterone acetate, Danazol, Allylestrenol, Gestrinone, Mepartricin, Raloxifene, Ormeloxifene, Levormeloxifene, antiestrogens (for example, Tamoxifen, Toremifene, etc.), the contraceptive pill, Mepitiostane, Testolactone, Aminoglutethimide, LH-RH agonists (for example, Goserelin acetate, Buserelin, Leuprorelin, etc.), LH-RH antagonists (for example. Ganirelix, Cetrorelix, Abarelix, etc.), Droloxifene, Epitiostanol, Ethinylestradiol sulfonate, aromatase inhibitors (for example, Fadrozole, Anastrozole, Letrozole, Exemestane, Vorozole, Formestane, etc.), anti-androgens (for example, Flutamide, Bicalutamide, Nilutamide, etc.), 5 α-reductase inhibitors (for example, Finasteride, Episteride, etc.), adrenocortical hormones (for example, Cortisol, Dexamethasone, Prednisolone, Betamethasone, Triamcinclone, etc.), inhibitors of androgen-synthesis (for example, Abiraterone, etc.), Retinoid and suppressing agents of Retinoid metabolism (for example, Liarozole, etc.), etc.

Examples of the alkylating agents include, for example, Nitrogen mustard, Nitrogen mustard N-oxide hydrochloride, Chlorambucil, Cyclophosphamide, Ifosfamide, Thiotepa, Carboquone, Improsulphan tosilate, Busulfan, Nimustine, Mitobronitol, Melphalan, Dacarbazine, Ranimustine, Estramustine phosphate sodium, Triethylenemelamine, Carmustine, Lomustine, Streptozocin, Pipobroman, Ethoglucid, Carboplatin, Cisplatin, Miboplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Adozelesin, Cystemustine, Bizelesin, etc.

Examples of the antimetabolites include, for example, Mercaptopurine, 6-Mercaptopurine riboside, Thioinosine, Methotrexate, Enocitabine, Cytarabine, Cytarabine ocfosfate, Ancitabine hydrochloride, 5-FU analogues (for example, Fluorouracil, Tegafur, UFT, Doxifluridine, Carmofur, Galocitabine, Emitefur, etc.), Aminopterin, Leucovorin calcium, Tabloid, Butocin, Calcium folinate, Calcium levofolinate, Cladribine, Fludarabine, Gemcitabine, Hydroxycarbamide, Pentostatin, Piritrexim, Idoxuridine, Mitoguazone, Tiazofurin, etc.

Example of antitumor antibiotics include, for example, Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, etc.

Examples of the plant alkaloid include, for example, Etoposide, Etoposide Phosphate, Vinblastine sulfate, Vincristine sulfate, Vindesine sulfate, Teniposide, Paclitaxel, Vinorelbine, etc.

Examples of the immunotherapy (BRM) include, for example, Picibanil, Krestin, Sizofiran, Lentinan, Ubenimex, Interferons, Interleukins, Macrophage-colony stimulating factor, granulocyte-colony stimulating factor, Erythropoietin, Lymphotoxin, BCG vaccine, Corynebacterium parvum, Levamisole, Polysaccharide-K, Procodazol, etc.

Others: L-asparaginase, Aceglatone, Procarbazine hydrochloride, Protoporphyrin, Hematoporphyrin, topoisomerase Iinhibitors (for example, Irinotecan, Topotecan, etc.), topoisomerase II inhibitors (for example, Sobuzoxane, etc.), differentiation promoter (for example, Retinoid, Vitamin D, etc.), inhibitor of proliferation factor (for example, Suramin, etc.), Antibodies(for example, Herceptin, etc.), Angiogenesis inhibitors, α-broker (for example, Tamsulosin hydrochloride, etc.), Tyrosin kinase inhibitors, etc.

Therapies other than chemotherapies, such as an operation including orchidectomy, thermotherapy, radiotherapy, etc., can be conducted together with the administration of Compound (I).

Particularly, androgens and/or estrogens in blood can be removed effectively by using the compound of the present invention in combination with a LH-RH modulator such as LH-RH agonist (for example, Goserelin acetate, Buserelin, Leuprorelin, etc.) and LHRH antagonist (for example, Ganirelix, Cetrorelix, Abarelix, etc.).

Thus, the compound of the present invention has high selectivity to Steroid $C_{17,20}$-lyase, and effectively reduce androgen concentration without affecting to drug metabolizing enzyme such as CYP3A4.

Examples of the pharmaceutically acceptable carrier include various organic or inorganic carriers which are used as a pharmaceutical ingredients. Excipients, lubricants, binders, disintegrators, thickeners can be used for solid preparations; solvents, dispersants, solubilizing agents, suspending agents, isotonic agents, buffer agents, soothing agents, etc., can be used for liquid preparations. If necessary, additives such as preservatives, antioxidants, coloring agents, sweetening agents, etc., can be used. Examples of the preferable excipient include, for example, lactose, saccharose, D-mannitol, starch, crystalline cellulose, light anhydrous silicic acid, etc. Examples of the preferable lubricant include, for example, magnesium stearate, calcium stearate, talc, colloidal silica, etc. Examples of the preferable binder include, for example, crystalline cellulose, saccharose, D-mannitol, dextrin, hydroxypropylcellulose, hydroxypropylmethylcellulose, polyvinyl pyrrolidone, etc. Examples of the preferable disintegrator include, for example, starch, carboxymethylcellulose, carboxymethylcellulose calcium, crosscarmelose sodium, carboxymethyl starch sodium, etc. Examples of the preferable thickener include, for example, natural rubbers, cellulose derivatives, acrylic acid polymers, etc. Examples of the preferable solvent include, for example, water for injection, alcohol, propyleneglycol, Macrogol, sesame oil, corn oil, etc. Examples of the preferable dispersant include, for example, Tween 80, HCO 60, polyethylene glycol, carboxymethylcellulose, sodium alginate, etc. Examples of the preferable solubilizing agent include, for example, polyethylene glycol, propyleneglycol, D-mannitol, benzyl benzoate, ethanol, trisaminomethane, cholesterol, triethanolamine, sodium carbonate, sodium citrate, etc. Examples of the preferable suspending agent include, for example, surfactants such as stearyl triethanolamine, sodium laurylsulfate, laurylaminopropionic acid, lecithin, benzalkonium chloride, benzethonium chloride, glycerin monostearate, etc.; for example, hydrophilic polymers such as polyvinylalcohol, polyvinyl pyrrolidone, sodium carboxymethyl cellulose, methylcellulose, hydroxymethylcellulose, hydroxyethylcellulose, hydroxypropylcellulose, etc. Examples of the preferable isotonic agent include, for example, sodium chloride, glycerin, D-mannitol, etc. Examples of the preferable buffer agent include, for example, buffer agents such as phosphoric acid salt, acetic acid salt, carbonate, citric acid salt, etc. Examples of the preferable soothing agent include, for example, benzyl alcohol, etc. Examples of the preferable preservative include, for example, paraoxybenzoates, chlorobutanol, benzyl alcohol, phenethylalcohol, dehydroacetic acid, sorbic acid, etc. Examples of the preferable antioxidant include, for example, sulfurous acid salt, ascorbic acid, etc.

The pharmaceutical preparation of the present invention can be manufactured by a usual manner. The ratio of the compound of the present invention contained in a pharmaceutical preparation is usually 0.1 to 100% (w/w). Examples of the embodiment of the pharmaceutical preparation are as follows:

(1) Tablets, Powder, Granules, Capsules:

These preparations can be prepared by adding, for example, exipients, disintegrators, binders or lubricants, etc., to Compound (I), by compressive molding the mixture and, if necessary, by coating for masking of taste, enteric or sustained release.

(2) Injections:

These preparations can be prepared by dissolving the compound of the present invention in aqueous injection together with, for example, dispersants, preservatives, isotonic agents, etc., or by dissolving, dispersing or emulsifying the compound of the present invention in a vegetable oil such as olive oil, sesame oil, cotton seed oil, corn oil, etc., or propyleneglycol, etc., to give an oily injection.

(3) Suppositories:

These preparations can be produced by preparing a liquid composition containing Compound (I), which may be oily, aqueous solid like or aqueous semisolid like. Examples of the oily base used for the composition include, for example, triglycerin ester of long-chain fatty acid (for example, cacao butter, witepsols, etc.), middle-chain fatty acid (for example, miglyols, etc.), vegetable oils (for example, sesame oil, soybean oil, cotton seed oil, etc.), etc. Examples of the aqueous gel base include, for example, natural rubber, cellulose derivative, vinyl polymer, acrylic acid polymer, etc. The content of the compound of the present invention in these preparations is usually 0.01 to 50%, though it varies depending upon the kind of pharmaceutical preparation.

The rate of the compound of the present invention in the above pharmaceutical preparation, varies depending upon the compound used, kind of animal to which the compound is administered, number of administration times, etc. The daily dose of the compound of the present invention, for example, for adult humans suffering from solid tumors (a patient suffering from, for example, prostate cancer), is usually about 0.001 to about 500 mg/kg-weight, preferably about 0.1 to about 40 mg/kg-weight, more preferably about 0.3 to about 5 mg/kg-weight. When the compound of the present invention is non-orally administered or when it is administered in combination with an other anti-cancer agent, the compound of the present invention is administered in a less amount mentioned above. A dose of the compound of the present invention actually administered are decided by a doctor by taking kind of compound, type of pharmaceutical preparation, age of the patient, body weight, sex, degree of disease, administration route, administration term and its interval, etc., into consideration, and the dose may be changed by a doctor.

The pharmaceutical preparation can be administered orally or parenterally. Examples of the parenteral administration route include intravenous, intramuscular, subcutaneous, intranasal, intradermal, instillation, intracerebral, intrarectal, intravaginal and intraperitoneal, etc.

The above mentioned administration term and administration interval varies depending upon the various conditions and decided by a doctor. As the administration, there may be mentioned divided administration, daily administration, intermittent administration, high dose administration therapy in short term, repeat administration, etc. It is preferable to administer the compound, for example, once to some times a day (especially two or three times a day). It is possible to administer the compound once to some times a day when oral administration. It is also possible to the compound as a sustained release preparation. It is also possible to the compound by intravenous drip infusion over a long time.

Modes of Working the Invention

The present invention is hereinafter described in more detail by means of the following Examples, pharmaceutical preparations and Experimental Examples, but these are merely described as examples and they are not intended to limit the present invention. The meanings of the following abbreviated symbols are as follows.

s: singlet, d: doublet, t: triplet, q: quartet, dd: double doublet, dt: double triplet, m: multiplet, br: broad, J: coupling constant, room temperature: 0~30° C., DMF: dimethylformamide, THF: tetrahydrofuran.

EXAMPLE

Reference Example 1

Production of 1-(6-tert-Butyldimethylsilyloxy-2-naphthyl)-2-methyl-1-(1-trityl-1H-imidazol-4-yl)-1-propanol A solution of n-butyllithium (1.6 M in hexane: 111 mL) was slowly added to a solution of 6-bromo-2-tert-butyldimethylsilyloxynaphthalene (60.0 g) in THF (600 mL) at −70° C. and the mixture was stirred for 30 min. A solution of α-methyl-1-(1-trityl-1H-imidazol-4-yl)-1-propanone (52.1 g) in THF (200 mL) was added to the mixture. After being stirred for 30 min at −70° C., the reaction was quenched with water. The organic layer was separated and water layer was extracted with ethyl acetate. The combined organic layer was washed with water and brine, dried and concentrated. The residue was crystallized from ethyl acetate-hexane to give the titled compound (79.5 g) as a colorless powder.

$^1$H-NMR (CDCl$_3$) δ: 0.23 (6H, s), 0.75 (3H, d, J=6.8 Hz), 0.95 (3H, d, J=6.6 Hz), 1.02 (9H, s), 2.45–2.59 (1H, m), 3.66 (1H, s), 6.80 (1H, d, J=1.4 Hz), 7.04 (1H, dd, J=2.4, 8.8 Hz), 7.11–7.16 (6H, m), 7.30–7.34 (11H, m), 7.49 (1H, dd, J=1.6, 8.6 Hz), 7.60 (1H, d, J=8.6 Hz), 7.68 (1H, d, J=8.8 Hz), 7.94 (1H, s). IR (KBr): 3158, 2955, 2930, 1601, 1493, 1480, 1445, 1260, 843 cm$^{-1}$.

Reference Example 2

Production of 6-(1-Hydroxy-2-methyl-1-(1-trityl-1H-imidazol-4-yl)propyl)-2-naphthol A solution of tetrabutylammonium fluoride in THF (1 M, 100 mL) was added to a solution of 1-(6-tert-butyldimethylsilyloxy-2-naphthyl)-2-methyl-1-(1-trityl-1H-imidazol-4-yl)-1-propanol (35.0 g) in THF (100 ml) at 0° C. and the mixture was stirred at room temperature for 1 h. The solvent was evaporated, and water was added to the residue. The precipitate was filtered, washed with diethyl ether and water to give the titled compound (28.3 g) as a colorless powder.

$^1$H-NMR (CDCl$_3$+CD$_3$OD) δ: 0.76 (3H, d, J=6.8 Hz), 0.95 (3H, d, J=6.6 Hz), 2.27–2.71 (1H, m), 6.86 (1H, d, J=1.4 Hz), 7.05–7.17 (7H, m), 7.31–7.38 (11H, m), 7.48 (1H, dd, J=1.8, 8.6 Hz), 7.58 (1H, d, J=8.8 Hz), 7.67 (1H, d, J=8.6 Hz), 7.85 (1H, s). IR (KBr): 3598, 2965, 1603, 1445, 1250, 1223, 1171, 760, 748, 702 cm$^{-1}$.

Reference Example 3

Production of 6-[1-Hydroxy-2-methyl-1-(1-trityl-1H-imidazol-4-yl)propyl]-2-naphthyl Trifluoromethanesulfonate Trifluoromethanesulfonic anhydride (9.1 mL) was added dropwise to a solution of 6-(1-hydroxy-2-methyl-1-(1-trityl-1H-imidazol-4-yl)propyl)-2-naphthol (27.0 g) in pyridine (200 mL) at 0° C. The reaction mixture was stirred for 1 h at 0° C., diluted with water and extracted with ethyl acetate. The organic layer was washed with brine, dried and concentrated. The residue was purified by silica gel column chromatography (eluent; hexane-ethyl acetate=1:1). Crystallization from diisopropyl ether gave the titled compound (29.6 g) as a colorless powder.

$^1$H-NMR (CDCl$_3$) δ: 0.73 (3H, d, J=6.6 Hz), 0.96 (3H, d, J=6.6 Hz), 2.47–2.60 (1H, m), 3.72 (1H, br s), 6.82 (1H, d, J=1.4 Hz), 7.10–7.17 (6H, m), 7.30–7.35 (11H, m), 7.65 (1H, dd, J=1.7, 8.6 Hz), 7.70 (1H, d, J=2.6 Hz), 7.77 (1H, d, J=8.6 Hz), 7.88 (1H, d, J=9.0 Hz), 8.11 (1H, s). IR (KBr): 3164, 2965, 1431, 1412, 1242, 1211, 1142, 909, 897, 748, 702 cm$^{-1}$.

Reference Example 4

Production of 6-(1-Hydroxy-2-methyl-1-(1-trityl-1H-imidazol-4-yl)propyl)-2-naphthonitrile A mixture of 6-[1-hydroxy-2-methyl-1-(1-trityl-1H-imidazol-4-yl)propyl]-2-naphthyl trifluoromethanesulfonate (2.0 g), zinc cyanide (240 mg) and tetrakis(triphenylphosphine)-palladium(0) (196 mg) in DMF (20 mL) was stirred at 80° C. for 4 h. After cooling, 5% aqueous ammonium hydroxide was added to the mixture and extracted with ethyl acetate. The extract was washed with water and brine and concentrated. The residue was purified by silica gel column chromatography (eluent; hexane-THF= 1:1). Crystallization from THF-hexane gave the titled compound (1.60 g) as a pale brown powder.

$^1$H-NMR (CDCl$_3$) δ: 0.72 (3H, d, J=6.8 Hz), 0.97 (3H, d, J=6.8 Hz), 2.47–2.60 (1H, m), 3.76 (1H, s), 6.82 (1H, s), 7.09–7.16 (6H, m), 7.30–7.37 (10H, m), 7.57 (1H, dd, J=1.5, 8.6 Hz), 7.68 (1H, dd, J=1.7, 8.8 Hz), 7.79 (1H, d, J=8.8 Hz), 7.87 (1H, d, J=8.6 Hz), 8.12 (1H, s), 8.17 (1H, s). IR (KBr): 3253, 2969, 2224, 1493, 1447, 1171, 747, 702 cm$^{-1}$.

Reference Example 5

Production of 6-(1-Hydroxy-1-(1H-imidazol-4-yl)-2-methylpropyl)-2-naphthonitrile A solution of 6-(1-hydroxy-2-methyl-1-(1-trityl-1H-imidazol-4-yl)propyl)-2-naphthonitrile (1.40 g) and pyridinium chloride (606 mg) in methanol-CHCl$_3$ (1:1, 8 mL) was heated at 60° C. for 2 h. The reaction mixture was neutralized with aq. NaHCO$_3$ solution and concentrated. The residue was extracted with ethanol, and the extract was purified by silica gel chromatography (eluent; dichloromethane:MeOH=30:1→10:1). Crystallization from ethyl acetate gave the titled compound (737 mg) as a colorless powder.

$^1$H-NMR (CDCl$_3$+CD$_3$OD) δ: 0.78 (3H, d, J=6.8 Hz), 0.97 (3H, d, J=6.8 Hz), 2.69–2.82 (1H, m), 7.03 (1H, d, J=1.2 Hz), 7.53 (1H, d, J=1.2 Hz), 7.58 (1H, dd, J=1.7, 8.6 Hz), 7.75 (1H, dd, J=1.6, 8.8 Hz), 7.83 (1H, d, J=8.8 Hz), 7.92 (1H, d, J=8.6 Hz), 8.12 (1H, s), 8.19 (1H, s). IR (KBr): 3250, 2980, 2230, 1346, 1242, 1113, 1034, 1019, 895, 822 cm$^{-1}$.

Reference Example 6

Production of 1-(6-tert-Butyldimethylsilyloxy-5-chloro-2-naphthyl)-2-methyl-1-(1-trityl-1H-imidazol-4-yl)-1-propanol In a similar manner to that described in Reference example 1, the reaction was carried out by using 1-chloro-6-bromo-2-tert-butyldimethylsilyloxynaphthalene (13.5 g) to give the titled compound (17.3 g) as a colorless powder.

$^1$H-NMR (CDCl$_3$) δ: 0.25 (6H, s), 0.74 (3H, d, J=6.8 Hz), 0.95 (3H, d, J=6.6 Hz), 1.07 (9H, s), 2.45–2.59 (1H, m), 3.70 (1H, s), 6.80 (1H, d, J=1.2 Hz), 7.07–7.16 (7H, m), 7.29–7.34 (10H, m), 7.59 (1H, dd, J=1.8, 8.8 Hz), 7.61 (1H, d, J=8.8 Hz), 7.99 (1H, d, J=1.8 Hz), 8.07 (1H, d, J=8.8 Hz). IR (KBr): 3155, 2957, 1599, 1474, 1360, 1252, 1020, 964, 841, 700 cm$^1$.

Reference Example 7

Production of 1-Chloro-6-(1-hydroxy-2-methyl-1-(1-trityl-1H-imidazol-4-yl)propyl)-2-naphthol In a similar manner to that described in Reference example 2, the reaction was carried out by using 1-(6-tert-butyldimethylsilyloxy-5-chloro-2-naphthyl)-2-methyl-1-(1-trityl-1H-imidazol-4-yl)-1-propanol (12.5 g) to give the titled compound (9.3 g) as a colorless powder.

$^1$H-NMR (CDCl$_3$+CD$_3$OD) δ: 0.73 (3H, d, J=7.0 Hz), 0.97 (3H, d, J=6.6 Hz), 2.48–2.61 (1H, m), 6.86 (1H, d, J=1.4 Hz), 6.90 (1H, d, J=9.2 Hz), 7.12–7.17 (6H, m), 7.31–7.47 (12H, m), 7.85 (1H, s), 7.94 (1H, d, J=9.2 Hz). IR (KBr): 3533, 2971, 1485, 1350, 1310, 1001, 758, 702 cm$^{-1}$.

Reference Example 8

Production of 1-Chloro-6-[1-hydroxy-2-methyl-1-(1-trityl-1H-imidazol-4-yl)propyl)-2-naphthyl Trifluoromethanesulfonate In a similar manner to that described in Reference example 3, the reaction was carried out by using 1-chloro-6-(1-hydroxy-2-methyl-1-(1-trityl-1H-imidazol-4-yl)propyl)-2-naphthol (8.8 g) to give the titled compound (10.2 g) as a colorless powder.

$^1$H-NMR (CDCl$_3$) δ: 0.72 (3H, d, J=6.6 Hz), 0.97 (3H, d, J=6.6 Hz), 2.48–2.61 (1H, m), 3.75 (1H, s), 6.82 (1H, d, J=1.6 Hz), 7.09–7.16 (6H, m), 7.30–7.37 (10H, m), 7.40 (1H, d, J=9.2 Hz), 7.75 (1H, dd, J=1.8, 8.8 Hz), 7.81 (1H, d, J=9.2 Hz), 8.15 (1H, d, J=1.8 Hz), 8.19 (1H, d, J=8.8 Hz). IR (KBr): 3194, 2965, 1422, 1221, 1134, 828, 702 cm$^1$.

Reference Example 9

Production of Methyl 1-Chloro-6-(1-hydroxy-2-methyl-1-(1-trityl-1H-imidazol-4-yl)propyl)-2-naphthoate In a similar manner to that described in Example 8-(i), the reaction was carried out by using 1-chloro-6-[1-(hydroxy-2-methyl-1-(1-trityl-1H-imidazol-4-yl)propyl)-2-naphthyl trifluoromethanesulfonate (3.0 g) to give the titled compound (2.3 g) as a colorless powder.

$^1$H-NMR (CDCl$_3$) δ: 0.72 (3H, d, J=7.0 Hz), 0.97 (3H, d, J=6.0 Hz), 2.44–2.61 (1H, m), 3.79 (1H, s), 3.98 (3H, s), 6.82 (1H, d, J=1.4 Hz), 7.09–7.14 (6H, m), 7.31–7.38 (10H, m), 7.70 (1H, dd, J=1.8, 9.0 Hz), 7.75 (s, 2H), 8.09 (1H, d, J=1.4 Hz), 8.34 (1H, d, J=9.2 Hz). IR (KBr): 3162, 1732, 1240, 1012, 747, 700 cm$^{-1}$.

Reference Example 10

Production of 1-(6-tert-Butyldimethylsilyloxy-5-methyl-2-naphthyl)-2-methyl-1-(1-trityl-1H-imidazol-4-yl)-1-propanol In a similar manner to that described in Reference example 1, the reaction was carried out by using 6-bromo-2-tert-butyldimethylsilyloxy-1-methylnaphthalene (17.0 g) to give the titled compound (21.6 g) as a colorless powder.

$^1$H-NMR (CDCl$_3$) δ: 0.22 (6H, s), 0.75 (3H, d, J=6.6 Hz), 0.95 (3H, d, J=6.6 Hz), 1.05 (9H, s), 2.50 (3H, s), 3.64 (1H, s), 6.80 (1H, d, J=1.2 Hz), 7.03 (1H, d, J=8.8 Hz), 7.10–7.16 (6H, m), 7.28–7.34 (10H, m), 7.55 (1H, d, J=8.8 Hz), 7.56 (1H, dd, J=1.8, 9.0 Hz), 7.81 (1H, d, J=9.0 hz), 7.92 (1H, d, J=1.8 Hz). IR (KBr): 3200, 2961, 1472, 1242, 839, 702 cm$^{-1}$.

Reference Example 11

Production 6-(1-Hydroxy-2-methyl-1-(1-trityl-1H-imidazol-4-yl)propyl)-1-methyl-2-naphthol In a similar manner to that described in Reference example 2, the reaction was carried out by using 1-(6-tert-butyldimethylsilyloxy-5-methyl-2-naphthyl)-2-methyl-1-(1-trityl-1H-imidazol-4-yl)-1-propanol (20 g) to give the titled compound (15.6 g) as a colorless powder.

$^1$H-NMR (CDCl$_3$) δ: 0.69 (1H, d, J=6.6 Hz), 1.03 (1H, d, J=6.6 Hz), 2.30–2.43 (1H, m), 2.43 (3H, s), 3.89 (1H, s), 6.04 (1H, d, J=8.8 Hz), 6.49 (1H, d, J=8.8 Hz), 6.85–6.93 (2H, m), 7.21–7.25 (6H, m), 7.37–7.48 (10H, m), 7.55 (1H, d, J=8.8 Hz), 7.56 (1H, d, J=1.0 Hz). IR (KBr): 3511, 2976, 1485, 1445, 1348, 1169, 1001, 758, 702 cm$^{-1}$.

Reference Example 12

Production of 6-[1-Hydroxy-2-methyl-1-(1-trityl-1H-imidazol-4-yl) propyl)-1-methyl-2-naphthyl Trifluoromethanesulfonate In a similar manner to that described in Reference example 3, the reaction was carried out by using 6-(1-hydroxy-2-methyl-1-(1-trityl-1H-imidazol-4-yl)propyl)-1-methyl-2-naphthol (14 g) to give the titled compound (10.7 g) as a colorless powder.

$^1$H-NMR (CDCl$_3$) δ: 0.73 (3H, d, J=6.6 Hz), 0.96 (3H, d, J=6.6 Hz), 2.48–2.63 (1H, m), 2.67 (3H, s), 3.70 (1H, s), 6.82 (1H, d, J=1.4 Hz), 7.10–7.16 (6H, m), 7.29–7.35 (11H, m), 7.69–7.74 (2H, m), 7.95 (1H, d, J=8.8 Hz), 8.07 (1H, d, J=1.8 Hz). IR (KBr): 3208, 2973, 1408, 1219, 1140, 897, 702 cm$^{-1}$.

Reference Example 13

Production of Methyl 6-(1-Hydroxy-2-methyl-1-(1-trityl-1H-imidazol-4-yl)propyl)-1-methyl-2-naphthoate In a similar manner to that described in Example 8-(i), the reaction was carried out by using 6-[1-(hydroxy-2-methyl-1-(1-trityl-1H-imidazol-4-yl)propyl)-1-methyl-2-naphthyl trifluoromethanesulfonate (6.0 g) to give the titled compound (4.2 g) as a colorless powder.

$^1$H-NMR (CDCl$_3$) δ: 0.74 (3H, d, J=7.0 Hz), 0.76 (3H, d, J=6.0 Hz), 2.48–2.62 (1H, m), 2.91 (3H, s), 3.74 (1H, s), 3.94 (3H, s), 6.82 (1H, d, J=1.4 Hz), 7.10–7.15 (6H, m), 7.30–7.34 (10H, m), 7.64–7.70 (2H, m), 7.80 (1H, d, J=8.8 Hz), 8.02 (1H, d, J=1.4 Hz), 8.08 (1H, d, J=9.2 Hz). IR (KBr): 3162, 2969, 1719, 1445, 1240, 1173, 747, 700 cm$^{-1}$.

Reference Example 14

Production of 1-(6-tert-Butyldimethylsilyloxy-7-methyl-2-naphthyl)-2-methyl-1-(1-trityl-1H-imidazol-4-yl)-1-propanol In a similar manner to that described in Reference example 1, the reaction was carried out by using 6-bromo-2-tert-butyldimethylsilyloxy-3-methyl-naphthalene (14.5 g) to give the titled compound (19.2 g) as a pale yellow powder.

$^1$H-NMR (CDCl$_3$) δ: 0.27 (6H, s), 0.75 (3H, d, J=6.6 Hz), 0.94 (3H, d, J=6.6 Hz), 1.05 (9H, s), 2.35 (3H, s), 2.45–2.58 (1H, m), 3.67 (1H, s), 6.80 (1H, d, J=1.2 Hz), 7.06 (1H, s), 7.11–7.15 (6H, m), 7.30–7.7.33 (10H, m), 7.44 (1H, dd, J=1.8, 8.6 Hz), 7.53–7.57 (2H, m), 7.86 (1H, s). IR (KBr): 3198, 1472, 1445, 1250, 1163, 1124, 914, 700 cm$^{-1}$.

Reference Example 15

Production of 6-(1-Hydroxy-2-methyl-1-(1-trityl-1H-imidazol-4-yl)propyl)-3-methyl-2-naphthol In a similar manner to that described in Reference example 2, the reaction was carried out by using 1-(6-tert-butyldimethylsilyloxy-7-methyl-2-naphthyl)-2-methyl-1-(1-trityl-1H-imidazol-4-yl)-1-propanol (18.5 g) to give the titled compound (14.9 g) as a colorless powder.

$^1$H-NMR (DMSO-d$_6$) δ: 0.61 (3H, d, J=6.8 Hz), 0.71 (3H, d, J=6.6 Hz), 2.27 (3H, s), 2.54–2.64 (1H, m), 5.04 (1H, s), 6.83 (1H, d, J=1.4 Hz), 7.03–7.08 (6H, m), 7.29 (1H, d, J=1.4 Hz), 7.33–7.41 (10H, m), 7.45–7.50 (2H, m), 7.69 (1H, dd, J=1.4, 8.8 Hz), 7.84 (1H, s). IR (KBr): 3603, 2966, 1670, 1447, 1244, 1159, 760, 748, 704 cm$^{-1}$.

Reference Example 16

Production of 6-[1-Hydroxy-2-methyl-1-(1-trityl-1H-imidazol-4-yl)propyl)-3-methyl-2-naphthyl Trifluoromethanesulfonate In a similar manner to that described in Reference example 3, the reaction was carried out by using 6-(1-hydroxy-2-methyl-1-(1-trityl-1H-imidazol-4-yl)propyl)-3-methyl-2-naphthol (14.0 g) to give the titled compound (12.9 g) as a colorless powder.

$^1$H-NMR (CDCl$_3$) δ: 0.72 (3H, d, J=7.0 Hz), 0.96 (3H, d, J=7.0 Hz), 2.46–2.59 (1H, m), 2.51 (3H, s), 3.72 (1H, s), 6.80 (1H, d, J=1.6 Hz), 7.09–7.16 (6H, m), 7.29–7.36 (10H, m), 7.56 (1H, dd, J=1.8, 8.6 Hz), 7.67–7.73 (3H, m), 8.02 (1H, s). IR (KBr): 3219, 2966, 1408, 1215, 1140, 1055, 895, 748, 700 cm$^{-1}$.

Reference Example 17

Production of Methyl 6-(1-Hydroxy-2-methyl-1-(1-trityl-1H-imidazol-4-yl)propyl)-3-methyl-2-naphthoate In a similar manner to that described in Example 8-(i), the reaction was carried out by using 6-[1-(hydroxy-2-methyl-1-(1-trityl-1H-imidazol-4-yl)propyl)-3-methyl-2-naphthyl trifluoromethanesulfonate (9.0 g) to give the titled compound (6.8 g) as a colorless powder.

$^1$H-NMR (CDCl$_3$) δ: 0.73 (3H, d, J=6.8 Hz), 0.95 (3H, d, J=6.6 Hz), 2.45–2.59 (1H, m), 2.71 (3H, s), 3.73 (1H, s), 3.94 (3H, s), 6.80 (1H, d, J=1.6 Hz), 7.10–7.16 (6H, m), 7.29–7.36 (10H, m), 7.54 (1H, dd, J=1.6, 8.6 Hz), 7.59 (1H, d, J=8.6 Hz), 7.96 (1H, s), 8.44 (1H, s). IR (KBr): 3223, 2968, 1724, 1445, 1283, 1267, 748, 700 cm$^{-1}$.

Reference Example 18

Production of (6-tert-Butyldimethylsilyloxy-2-naphthyl)(1-trityl-1H-imidazol-4-yl)methanol In a similar manner to that described in Reference example 1, the reaction was carried out by using 6-bromo-2-tert-butyldimethylsilyloxynaphthalene (50.0 g) and 4-formyl-1-trityl-1H-imidazole (38.6 g) to give the titled compound (49.8 g) as a colorless powder.

$^1$H-NMR (CDCl$_3$) δ: 0.23 (6H, s), 1.01 (9H, s), 3.91 (br s, 1H), 5.88 (1H, d, J=3.0 Hz), 6.63 (1H, s), 7.01–7.14 (8H, m), 7.25–7.33 (9H, m), 7.39–7.44 (2H, m), 7.58–7.68 (2H, m), 7.78 (1H, s). IR (KBr) 3196, 2955, 1607, 1483, 1277, 1159, 831 775, 700 cm$^{-1}$.

Reference Example 19

Production of (6-tert-Butyldimethylsilyloxy-2-naphthyl)(1-trityl-1H-imidazol-4-yl)methanone To a solution of (6-tert-butyldimethylsilyloxy-2-naphthyl)(1-trityl-1H-imidazol-4-yl)methanol (49.0 g) in dichloromethane (400 mL) was added MnO$_2$ (150 g) and the mixture was stirred for 3 h at room temperature. The reaction mixture was filtered and the filtrate was concentrated to give the titled compound (45.3 g) as a pale yellow powder.

$^1$H-NMR (CDCl$_3$) δ: 0.26 (6H, s), 1.02 (9H, s), 7.08–7.22 (8H, m), 7.33–7.40 (9H, m), 7.57 (1H, d, J=1.0 Hz), 7.72 (1H, d, J=8.8 Hz), 7.76 (1H, d, J=1.4 Hz), 7.84 (1H, d, J=8.8 Hz), 8.21 (1H, dd, J=1.8, 8.4 Hz), 8.94 (1H, s). IR (KBr): 2930, 1622, 1474, 1263, 1182, 891, 700 cm$^1$.

Reference Example 20

Production of (6-Hydroxy-2-naphthyl)(1-trityl-1H-imidazol-4-yl)methanone

In a similar manner to that described in Reference example 2, the reaction was carried out by using (6-tert-butyldimethylsilyloxy-2-naphthyl)(1-trityl-1H-imidazol-4-yl)methanone (21.5 g) to give the titled compound (16.8 g) as a colorless powder.

$^1$H-NMR (CDCl$_3$+CD$_3$OD) δ: 7.13–7.23 (8H, m), 7.36–7.42 (9H, m), 7.63–7.70 (3H, m), 7.77 (1H, d, J=9.6 Hz), 8.02 (1H, dd, J=1.6, 8.6 Hz), 8.61 (1H, s). IR (KBr): 3360, 3057, 1618, 1475, 1182, 1173, 768, 754, 706 cm$^{-1}$.

Reference Example 21

Production of 6-[(1-Trityl-1H-imidazol-4-yl)carbonyl]-2-naphthyl Trifluoromethanesulfonate In a similar manner to that described in Reference Example 3, the reaction was carried out by using (6-hydroxy-2-naphthyl)(1-trityl-1H-imidazol-4-yl)methanone (15.0 g) to give the titled compound (18.6 g) as a pale yellow powder.

$^1$H-NMR (CDCl$_3$) δ: 7.15–7.22 (6H, m), 7.31–7.44 (10H, m), 7.58 (1H, d, J=1.2 Hz), 7.78 (1H, d, J=2.2 Hz), 7.83 (1H, d, J=1.2 Hz), 7.93 (1H, d, J=8.6 Hz), 8.06 (1H, d, J=9.0 HZ), 8.38 (1H, dd, J=1.4, 8.6 Hz), 9.08 (1H, s). IR (KBr): 3063, 1645, 1512, 1404, 1219, 1173, 1140, 905, 748, 702 cm$^{-1}$.

Reference Example 22

Production of Methyl 6-[(1-Trityl-1H-imidazol-4-yl)carbonyl]-2-naphthoate

In a similar manner to that described in Example 8-(i), the reaction was carried out by using 6-[(1-trityl-1H-imidazol-4-yl)carbonyl]-2-naphthyl trifluoromethanesulfonate (8.0 g) to give the titled compound (18.6 g) as a pale yellow powder.

$^1$H-NMR (CDCl$_3$) δ: 3.99 (3H, s), 7.15–7.22 (6H, m), 7.35–7.40 (9H, m), 7.58 (1H, d, J=1.4 Hz), 7.82 (1H, d, J=1.4 Hz), 7.99–8.04 (2H, m), 8.10 (1H, dd, J=1.4, 8.8 Hz), 8.31 (1H, dd, J=1.8, 8.6 Hz), 8.63 (1H, s), 9.00 (1H, s). IR (KBr) 2951, 1722, 1512, 1279, 1240, 1169, 750 cm$^{-1}$.

Reference Example 23

Production of N-Methyl-6-[(1-trityl-1H-imidazol-4-yl)carbonyl]-2-naphthamide

In a similar manner to that described in Example 9-(i) the reaction was carried out by using methyl 6-[(1-trityl-1H-imidazol-4-yl)carbonyl]-2-naphthoate (4.0 g) to give the titled compound (3.38 g) as a pale yellow powder.

$^1$H-NMR (CDCl$_3$) δ: 3.06 (3H, d, J=5.0 Hz), 6.48 (1H, d, J=5.0 Hz), 7.14–7.22 (6H, m), 7.36–7.40 (9H, m), 7.58 (1H, d, J=1.0 Hz), 7.80–7.87 (2H, m), 7.91–8.01 (2H, m), 8.25–8.30 (2H, m), 8.96 (1H, s). IR (KBr): 3452, 3128, 1672, 1514, 1242, 1175, 748, 702 cm$^{-1}$.

Reference Example 24

Production of 6-Bromo-2-hydroxy-1-naphthaldehyde

To a solution of 2-hydroxy-1-naphthaldehyde (60.0 g) in AcOH (300 mL) was added dropwise a solution of bromine (66.8 g) in AcOH (30 mL) over 30 min. After being stirred for 1 h, the mixture was poured into aqueous Na$_2$S$_{2O3}$ solution, and the resulting mixture was extracted with AcOEt. The combined organic layers were washed with water, 1N-NaOH, and brine followed by drying over MgSO$_4$. After removal of the solvent in vacuo, the residue was washed with EtOH to give a yellow powder. The powder was crystallized from iPrOH to afford the title compound (28.8 g) as pale yellow needles.

¹H-NMR (CDCl₃) δ: 7.18 (1H, d, J=9.0 Hz), 7.69 (1H, dd, J=2.2, 9.2 Hz), 7.89 (1H, d, J=9.2 Hz), 7.96 (1H, d, J=2.2 Hz), 8.22 (1H, d, J=9.0 Hz), 10.77 (1H, s). IR (KBr): 3096, 1639, 1462, 1308, 1165, 876, 810 cm⁻¹. Anal. Calcd for C₁₁H₇O₂Br: C, 52.62; H, 2.82. Found: C, 52.58; H, 2.61.

Reference Example 25

Production of 6-Bromo-2-hydroxy-1-naphthoic Acid

To a ice-cooled mixture of 6-Bromo-2-hydroxy-1-naphthaldehyde (24.0 g) and aqueous NaH₂PO₄ solution (3.2 g in 30 mL of water) in DMSO (160 mL) was added dropwise a solution of NaClO₂ (80%; 15.1 g) in water (150 mL) over 1 h. After being stirred for 5 h at room temperature, a solution of NaClO₂ (80%; 2.16 g) in water (20 mL) was added, and the reaction mixture was further stirred for 2 h at room temperature. The mixture was alkalized with 1N-NaOH, and the precipitate was filtered off. The filtrate was washed with AcOEt and iPr₂O, and then the aqueous phase was acidified with conc. HCl. The precipitate was filtered, washed with water, and dried in vacuo to give the title compound (22.3 g) as a brown powder.

¹H-NMR (DMSO-d₆) δ: 7.25 (1H, d, J=9.2 Hz), 7.66 (1H, dd, J=2.2. 9.0 Hz), 7.99 (1H, d, J=9.0 Hz), 8.15 (1H, d, J=2.2 Hz), 8.39 (1H, d, J=9.2 Hz). IR (KBr): 3000, 1649, 1441, 1298, 1248, 1190 cm⁻¹.

Reference Example 26

Production of 6-Bromo-2-hydroxy-N-methyl-1-naphthamide

To a ice-cooled solution of 6-Bromo-2-hydroxy-1-naphthoic acid (10.0 g) and triethylamine (26.1 mL) in anhydrous THF (300 mL) was added dropwise methanesulfonyl chloride (7.0 mL), and the mixture was stirred for 90 min at room temperature. A solution of methylamine (2M in THF; 60 mL) was added, and the reaction mixture was further stirred for overnight at room temperature. The mixture was acidified with conc. HCl and extracted with ethyl acetate. The combined organic layer was washed with brine, dried over MgSO₄ followed by concentrating in vacuo. The residue was washed hexane-ethyl acetate (1:1) to give a light brown powder. The powder was dissolved in THF-MeOH-4N-NaOH (6:1:1, 80 mL), and the mixture was heated at 70° C. for 30 min. After cooling to room temperature, the mixture was acidified with conc. HCl and concentrated in vacuo. The residue was washed with water and AcOEt to give the title compound (4.61 g) as light brown powder.

¹H-NMR (DMSO-d₆) δ: 2.82 (3H, d, J=4.4 Hz), 7.22 (1H, d, J=9.0 Hz), 7.54 (1H, dd, J=1.4, 9.2 Hz), 7.61 (1H, d, J=9.2 Hz), 7.79 (1H, d, J=9.0 Hz), 8.08 (1H, d, J=1.4 Hz), 8.23 (1H, d, J=4.4 Hz). IR (KBr): 3360, 3053, 1609, 1580, 1499, 1408, 1344 cm₋₁.

Reference Example 27

Production of 6-Bromo-2-methoxy-N-methyl-1-naphthamide

A mixture of 6-Bromo-2-hydroxy-N-methyl-1-naphthamide (1.20 g), dimethylsulfate (0.49 mL), and powdered K₂CO₃ (1.18 g) in anhydrous DMF (10 mL) was heated at 60° C. for 30 min. After dilution with 1N HCl, the resulting mixture was extracted with Ethyl acetate. The combined organic layers were washed with water and brine followed by drying over MgSO₄. After removal of the solvent in vacuo, the residue was washed with hexane-AcOEt (1:1) to give the title compound (1.21 g) as a colorless powder.

¹H-NMR (DMSO-d₆) δ: 2.82 (3H, d, J=4.6 Hz), 3.90 (3H, s), 7.56–7.60 (3H, m), 7.98 (1H, d, J=9.2 Hz), 8.18 (1H, s), 8.31 (1H, d, J=4.6 Hz).
IR (KBr): 3253, 2943, 1634, 1585, 1493, 1265 cm⁻¹.

Reference Example 28

Production of 6-Bromo-2-(tert-butyldimethylsilyloxy)-N-methyl-1-naphthamide

A mixture of 6-bromo-2-hydroxy-N-methyl-1-naphthamide (2.50 g), tert-butyldimethylsilyl chloride (1.61 g), and imidazole (912 mg) in DMP (30 mL) was stirred for 2 h at room temperature. After dilution with water, the resulting mixture was extracted with AcOEt. The organic layer was washed with water and brine followed by concentrating in vacuo. The residue was passed through silica gel plug (hexane:AcOEt=1:1). The elute was concentrated, and the residue was washed with hexane to give the titled compound (3.33 g) as colorless needles.

¹H-NMR (CDCl₃) δ: 0.24 (6H, s), 1.01 (9H, s), 3.06 (3H, d, J=5.0 Hz), 6.02 (1H, d, J=5.0 Hz), 7.05 (1H, d, J=8.8 Hz), 7.52 (1H, dd, J=2.0, 8.8 Hz), 7.65 (1H, d, J=8.8 Hz), 7.87–7.91 (2H, m). IR (KBr): 3275, 2930, 1632, 1585, 1252, 841 cm⁻¹.

Reference Example 29

Production of 1-[6-(tert-Butyldimethylsilyloxy)-2-naphthyl]-3-methyl-1-(1-trityl-1H-imidazol-4-yl)-1-butanol 6-Bromo-2-tert-butyldimethylsilyloxynaphthalene (33.7 g) and 3-methyl-1-(1-trityl-1H-imidazol-4-yl)-1-butanone (31.5 g) were used as the starting materials. By the same procedure described in Reference example 1, the titled compound (40.6 g) was obtained as a colorless powder.

¹H-NMR (CDCl₃) δ: 0.23 (6H, s), 0.76 (3H, d, J=6.6 Hz), 0.89 (3H, d, J=6.8 Hz), 1.01 (9H, s), 1.62–1.81 (1H, m), 2.07 (2H, d, J=4.4 Hz), 3.55 (1H, s), 6.75 (1H, d, J=1.2 Hz), 7.04 (1H, dd, J=2.4, 8.6 Hz), 7.12–7.19 (7H, m), 7.32–7.35 (10H, m), 7.39 (1H, dd, J=1.8, 8.8 Hz), 7.58 (1H, d, J=8.6 Hz), 7.68 (1H, d, J=9.2 Hz), 7.91 (1H, s). IR (KBr): 3132, 2949, 1495, 1474, 1445, 1261, 700 cm⁻¹.

Reference Example 30

Production of 6-[1-Hydroxy-3-methyl-1-(1-trityl-1H-imidazol-4-yl)butyl]-2-naphthol 1-[6-(tert-Butyldimethylsilyloxy)-2-naphthyl]-3-methyl-1-(1-trityl-1H-imidazol-4-yl)-1-butanol (39.8 g) was used as a starting material. By the same procedure described in Reference example 2, the title compound (31.9 g) was obtained as a colorless powder.

¹H-NMR (CDCl₃) δ: 0.64 (3H, d, J=6.6 Hz), 0.87 (3H, d, J=7.0 Hz), 1.55–1.74 (1H, m), 1.90 (1H, dd, J=5.0, 14.2 Hz), 2.08 (1H, dd, J=6.2, 14.2 Hz), 3.53 (1H, s), 6.29 (1H, dd, J=2.2, 8.8 Hz), 6.40 (1H, s), 6.83 (1H, d, J=9.2 Hz), 6.93 (1H, d, J=7.8 Hz), 7.09 (1H, d, J=8.8 Hz), 7.22–7.25 (6H, m), 7.40–7.43 (11H, m), 7.59 (1H, s), 10.93 (1H, br s). IR (KBr): 3510, 3057, 2951, 1447, 1308, 1175, 856, 748, 704 cm⁻¹.

Reference Example 31

Production of 6-[1-Hydroxy-3-methyl-1-(1-trityl-1H-imidazol-4-yl)butyl]-2-naphthyl Trifluoromethanesulfonate 6-[1-hydroxy-3-methyl-1-(1-trityl-1H-imidazol-4-yl) butyl]-2-naphthol (30.0 g) was used as a starting material.

By the same procedure described in Reference example 3, the titled compound (33.9 g) was obtained as a colorless powder.

$^1$H-NMR (CDCl$_3$) δ: 0.74 (3H, d, J=6.6 Hz), 0.90 (3H, d, J=6.6 Hz), 1.60–1.79 (1H, m), 2.09 (2H, d, J=6.0 Hz), 3.71 (1H, s), 6.77 (1H, d, J=1.0 Hz)<7.11–7.18 (6H, m), 7.31–7.36 (11H, m), 7.55 (1H, dd, J=1.8, 8.8 Hz), 7.69 (1H, d, J=2.4 Hz), 7.75 (1H, d, J=8.8 Hz), 7.87 (1H, d, J=9.2 Hz), 8.09 (1H, s). IR (KBr): 3188, 2951, 1425, 1217, 1138, 908, 702 cm$^{-1}$.

Reference Example 32

Production of Methyl 6-[1-Hydroxy-3-methyl-1-(1-trityl-1H-imidazol-4-yl)butyl]-2-naphthoate 6-[1-Hydroxy-3-methyl-1-(1-trityl-1H-imidazol-4-yl) butyl]-2-naphthyl trifluoromethanesulfonate (28.0 g) was used as a starting material. By the same procedure described in Example 8-(i), the titled compound (21.9 g) was obtained as a light brown powder.

$^1$H-NMR (CDCl$_3$) δ: 0.74 (3H, d, J=6.6 Hz), 0.90 (3H, d, J=6.6 Hz), 1.62–1.81 (1H, m), 2.09 (2H, d, J=6.0 Hz), 3.67 (1H, s), 3.70 (3H, s), 6.77 (1H, d, J=1.4 Hz), 7.11–7.18 (6H, m), 7.30–7.37 (10H, m), 7.52 (1H, dd, J=1.8, 8.4 Hz), 7.83 (2H, d, J=8.2 Hz), 8.00–8.06 (2H, m), 8.55 (1H, s). IR (KBr): 3200, 2957, 1709, 1281, 1232, 1198, 752, 702 cm$^{-1}$.

Reference Example 33

Production of 6-[1-Hydroxy-1-(1H-imidazol-4-yl)-2-methylpropyl]-2-methoxy-N-methyl-1-naphthamide (i) Production of 6-[1-Hydroxy-2-methyl-1-(1-trityl-1H-imidazol-4-yl)propyl]-2-methoxy-N-methyl-1-naphthamide To a cooled (−50° C.) solution of 6-bromo-2-methoxy-N-methyl-1-naphthamide (1.10 g) in anhydrous THF (80 mL) was added dropwise n-butyllithium in hexane (1.6 M; 5.14 mL), and the solution was stirred for 20 min at −50° C. A solution of 2-methyl-1-(1-trityl-1H-imidazol-4-yl)-1-propanol (1.56 g) in anhydrous THF (10 mL) was added dropwise, and the reaction mixture was stirred for 20 min at −50° C. After dilution with water, the resulting mixture was extracted with AcOEt. The organic layer was washed with brine and dried over MgSO$_4$ followed by concentrating in vacuo. The residue was purified by column chromatography on silica gel (hexane:THF=3:2→1:2) to the title compound (680 mg) as a pale yellow amorphous powder.

$^1$H-NMR (CDCl$_3$) δ: 0.71 (3H, d, J=6.6 Hz), 0.93 (3H, d, J=7.0 Hz), 2.44–2.57 (1H, m), 3.09 (3H, d, J=4.6 Hz), 3.71 (1H, s), 3.93 (3H, s), 6.02 (1H, d, J=4.6 Hz), 7.79 (1H, d, J=1.6 Hz), 7.09–7.16 (6H, m), 7.22 (1H, d, J=9.2 Hz), 7.29–7.36 (10H, m), 7.49 (1H, dd, J=1.9, 8.7 Hz), 7.80 (1H, d, J=2.2 Hz), 7.84 (1H, d, J=2.6 Hz), 8.08 (1H, d, J=1.4 Hz). IR (KBr): 3300, 2966, 1641, 1493, 1445, 1254, 1161, 748, 702 cm$^{-1}$.

(ii) Production of 6-[1-Hydroxy-1-(1H-imidazol-4-yl)-2-methylpropyl]-2-methoxy-N-methyl-1-naphthamide 6-[1-Hydroxy-2-methyl-1-(1-trityl-1H-imidazol-4-yl) propyl]-2-methoxy-N-methyl-1-naphthamide (640 mg) was used as a starting material. By the same procedure described in Reference example 5, the titled compound (316 mg) was obtained as a colorless amorphous powder.

$^1$H-NMR (CDCl$_3$+CD$_3$OD) δ: 0.77 (3H, d, J=7.0 Hz), 0.97 (3H, d, J=6.6 Hz), 2.58–2.71 (1H, m), 3.05 (3H, d, J=3.0 Hz), 3.92 (3H, s), 6.69 (1H, br s), 6.89 (1H, d, J=1.0 Hz), 7.22 (1H, d, J=9.2 Hz), 7.35 (1H, d, J=1.0 Hz), 7.51 (1H, d, J=1.8, 9.0 Hz), 7.72 (1H, d, J=9.0 Hz), 7.83 (1H, d, J=9.2 Hz), 7.92 (1H, s). IR (KBr): 3300, 2966, 1636, 1254, 1161, 1090, 824 cm$^{-1}$.

Reference Example 34

Production of 2-Hydroxy-6-[1-hydroxy-1-(1H-imidazol-4-yl)-2-methylpropyl]-N-methyl-1-naphthamide (i) Production of 2-Hydroxy-6-[1-hydroxy-2-methyl-1-(1-trityl-1H-imidazol-4-yl)propyl]-N-methyl-1-naphthamide 6-Bromo-2-(tert-butyldimethylsilyloxy)-N-methyl-1-naphthamide (3.30 g) and 2-methyl-1-(1-trityl-1H-imidazol-4-yl)-1-propanol (2.66 g) were used as the starting materials. By the same procedure described in Reference example 33-(i), a crude mixture of 2-(tert-butyldimethylsilyloxy)-6-[1-hydroxy-2-methyl-1-(-1-trityl-1H-imidazol-4-yl)propyl]-N-methyl-1-naphthamide was obtained. The crude mixture and tetrabutylammonium fluoride hydrate (3.00 g) was dissolved in THF (30 mL), and the solution was stirred for 1 h at room temperature. After dilution with water, the resulting mixture was extracted with AcOEt. The organic layer was washed with brine and dried over MgSO$_4$ followed by concentrating in vacuo. The residue was purified by flash column chromatography on silica gel (hexane:AcOEt=2:1→1:2) to give a colorless solid. The solid was washed with iPr$_2$O to afford the titled compound (1.48 g) as a colorless powder.

$^1$H-NMR (DMSO-d$_6$) δ: 0.61 (3H, d, J=6.8 Hz), 0.77 (3H, d, J=6.6 Hz), 2.57–2.70 (1H, m), 2.82 (3H, d, J=3.6 Hz), 5.12 (1H, s), 6.83 (1H, d, J=1.4 Hz), 7.02–7.07 (5H, m), 7.12 (1H, d, J=8.8 Hz), 7.29 (1H, d, J=1.4 Hz), 7.34–7.41 (10H, m), 7.55 (1H, d, J=8.8 Hz), 7.71 (1H, d, J=8.8 Hz), 7.80 (1H, dd, J=2.0, 8.8 Hz), 7.95 (1H, s), 8.16 (1H, d, J=4:6 Hz). IR (KBr): 3450, 2974, 1651, 1493, 1248, 1173, 750, 702 cm$^{-1}$.

(ii) Production of 2-Hydroxy-6-[1-hydroxy-1-(1H-imidazol-4-yl)-2-methylpropyl]-N-methyl-1-naphthamide 2-Hydroxy-6-[1-hydroxy-2-methyl-1-(1-trityl-1H-imidazol-4-yl)propyl]-N-methyl-1-naphthamide (600 mg) was used as a starting material. By the same procedure described in Reference example 5, the titled compound (233 mg) was obtained as a colorless powder.

$^1$H-NMR (DMSO-d$_6$) δ: 0.65 (3H, d, J=6.6 Hz), 0.83 (3H, d, J=6.2 Hz), 2.62–2.75 (1H, m), 2.80 (3H, d, J=4.4 Hz), 5.08 (1H, br s), 6.94 (1H, s), 7.11 (1H, d, J=8.8 Hz), 7.51–7.56 (2H, m), 7.70–7.74 (2H, m), 7.95 (1H, s), 8.14 (1H, d, J=4.4 Hz), 9.86 (1H, br s), 11.78 (1H, br s). IR (KBr) 3427, 3256, 2976, 1647, 1528, 1352, 1285, 1248 cm$^{-1}$.

Reference Example 35

Production of 6-[1-Hydroxy-1-(1H-imidazol-4-yl)-2-methylpropyl]-N-methyl-1-naphthamide I. Production of 6-[1-Hydroxy-2-methyl-1-(1-trityl-1H-imidazol-4-yl)propyl]-1-(methylaminocarbonyl)-2-naphthyl Trifluoromethanesulfonate 2-Hydroxy-6-[1-hydroxy-2-methyl-1-(1-trityl-1H-imidazol-4-yl)propyl]-N-methyl-1-naphthamide (1.10 g) was used as a starting material. By the same procedure described in Reference example 3, the titled compound (1.38 g) was obtained as a colorless powder.

$^1$H-NMR (CDCl$_3$) δ: 0.69 (3H, d, J=7.0 Hz), 0.94 (3H, d, J=6.6 Hz), 2.45–2.59 (1H, m), 3.11 (3H, d, J=4.8 Hz), 3.76 (1H, br s), 6.18 (2H, d, J=4.8 Hz), 6.81 (1H, d, J=1.2 Hz), 7.08–7.15 (6H, m), 7.29–7.37 (11H,), 7.66 (1H, dd, J=1.6. 9.0 Hz), 8.12 (1H, d, J=1.4 Hz). IR (KBr): 3260, 2970, 1659, 1423, 1219, 1140, 949, 731, 702 cm$^{-1}$.

(ii) Production of 6-[1-Hydroxy-2-methyl-1-(1-trityl-1H-imidazol-4-yl)propyl]-N-methyl-1-naphthamide A mixture of 6-[1-hydroxy-2-methyl-1-(1-trityl-1H-imidazol-4-yl)propyl]-1-(methylaminocarbonyl)-2-naphthyl trifluoromethanesulfonate (700 mg), formic acid (0.1 mL), tributylamine (1.0 mL), dichlorobis(triphenylphosphine) palladium (70 mg), and 1,3-bis-(diphenylphosphino) propane (103 mg) in anhydrous DMF (5 mL) was heated at 80° C. for 4 h. After dilution with water, the yellow precipitate was filtered and washed with water. The precipitate was purified by flash column chromatography on silica gel (hexane:AcOEt=3:2→1:1) to give the title compound (384 mg) as a colorless amorphous powder.

$^1$H-NMR (CDCl$_3$) δ: 0.72 (3H, d, J=6.6 Hz), 0.95 (3H, d, J=6.6 Hz), 2.46–2.59 (1H, m), 3.08 (3H, d, J=5.0 Hz), 3.75 (1H, s), 6.04 (1H, d, J=5.0 Hz), 6.81 (1H, d, J=1.0 Hz), 7.10–7.15 (6H, m), 7.30–7.35 (10H, m), 7.41 (1H, d, J=8.0 Hz), 7.51–7.61 (2H, m), 7.87 (1H, d, J=8.0 Hz), 8.10 (1H, d, J=1.4 Hz), 8.20 (1H, d, J=9.2 Hz). IR (KBr): 3273, 2968, 1639, 1161, 908, 733, 702 cm$^{-1}$.

(iii) Production of 6-[1-Hydroxy-1-(1H-imidazol-4-yl)-2-methylpropyl]-N-methyl-1-naphthamide 6-[1-Hydroxy-2-methyl-1-(1-trityl-1H-imidazol-4-yl)propyl]-N-methyl-1-naphthamide (350 mg) was used as a starting material. By the same procedure described in Reference example 5, the title compound (171 mg) was obtained as a colorless amorphous powder.

$^1$H-NMR (DMSO-d$_6$) δ: 0.65 (3H, d, J=6.6 Hz), 0.85 (3H, d, J=6.4 Hz), 2.68–2.81 (1H, m), 2.83 (3H, d, J=4.4 Hz), 5.17 (1H, br s), 6.98 (1H, s), 7.42–7.53 (3H, m), 7.85–7.95 (2H, m), 8.04–8.12 (2H, m), 8.37 (1H, d, J=4.4 Hz), 11.80 (1H, br s). IR (KBr): 3500–3200, 2968, 1624, 1547, 1410, 1308, 829, 806 cm$^{-1}$.

Example 1

Production of 1-(1H-Imidazol-4-yl)-2-methyl-1-(6-phenyl-2-naphthyl)-1-propanol (i) Production of 2-Methyl-1-(6-phenyl-2-naphthyl)-1-(1-trityl-1H-imidazol-4-yl)-1-propanol 6-[1-hydroxy-2-methyl-1-(1-trityl-1H-imidazol-4-yl)propyl]-2-naphthyl trifluoromethanesulfonate (2.0 g), phenylboronic acid (446 mg), tetrakis(triphenylphosphine)-palladium (0) (115 mg) and lithium chloride (259 mg) were dissolved in dimethoxyethane (DME, 20 mL). Ag.Na$_2$CO$_3$ (2M, 4.5 mL) was added to the mixture, and whole was heated at 80° C. for 20 h. Water was added, the mixture was extracted with AcOEt. The extract was washed with brine, dried and concentrated. The residue was purified by column chromatography (eluent, hexane:THF=2:1) to give the titled compound (1.50 g) as a pale yellow powder.

$^1$H-NMR (CDCl$_3$) δ: 0.76 (3H, d, J=6.8 Hz), 0.97 (3H, d, J=6.8 Hz), 2.49–2.63 (1H, m), 3.72 (1H, s), 6.82 (1H, d, J=1.4 Hz), 7.11–7.17 (6H, m), 7.31–7.39 (12H, m), 7.44–7.51 (2H, m), 7.59 (1H, dd, J=1.8, 8.0 Hz), 7.69 (1H, d, J=1.0 Hz), 7.73 (1H, d, J=1.6 Hz), 7.80 (1H, d, J=8.8 Hz), 7.87 (1H, d, J=8.6 Hz), 7.99 (1H, s), 8.05 (1H, s). IR (KBr): 3200, 2967, 1491, 1470, 1445, 1142, 1015, 872, 820, 754 cm$^{-1}$.

(ii) Production of 1-(1H-Imidazol-4-yl)-2-methyl-1-(6-phenyl-2-naphthyl)-1-propanol In a similar manner to that described in Reference example 5, the reaction was carried out by using 2-methyl-1-(6-phenyl-2-naphthyl)-1-(1-trityl-1H-imidazol-4-yl)-1-propanol (1.30 g) to give the titled compound (629 mg) as a colorless powder.

$^1$H-NMR (CDCl$_3$+CD$_3$OD) δ: 0.83 (3H, d, J=6.8 Hz), 1.03 (3H, d, J=6.6 Hz), 2.69–2.82 (1H, m), 7.02 (1H, d, J=1.2 Hz), 7.33–7.52 (4H, m), 7.61 (1H, dd, J=1.6, 8.6 Hz), 7.69–7.75 (3H, m), 7.83 (1H, d, J=8.8 Hz), 7.90 (1H, d, J=8.6 Hz), 8.00 (1H, s), 8.03 (1H, s). IR (KBr): 3401, 3241, 2973, 1393, 1017, 980, 897, 829, 756 cm$^{-1}$.

Example 2

Production of 1-(6-(2-Furyl)-2-naphthyl)-1-(1H-imidazol-4-yl)-2-methyl-1-propanol (i) Production of 1-(6-(2-Furyl)-2-naphthyl)-2-methyl-1-(1-trityl-1H-imidazol-4-yl)-1-propanol 6-[1-Hydroxy-2-methyl-1-(1-trityl-1H-imidazol-4-yl)propyl]-2-naphthyl trifluoromethanesulfonate (2.0 g), 2-(tributylstannyl)furan (1.26 mL), tetrakis(triphenylphosphine)palladium (115 mg) and lithium chloride (259 mg) were dissolved in DMF (10 mL) and heated at 80 for 4 h. The reaction mixture was diluted with water, extracted with ethyl acetate. The extract was washed with water and brine, dried and concentrated. The residue was purified by column chromatography (eluent; hexane:THF= 4:1) and crystallized from ethyl acetate-hexane to give the titled compound (1.48 g) as a colorless powder.

$^1$H-NMR (CDCl$_3$) δ: 0.76 (3H, d, J=6.8 Hz), 0.96 (3H, d, J=6.6 Hz), 2.47–2.60 (1H, m), 3.72 (1H, s), 6.51 (1H, dd, J=1.8, 3.4 Hz), 6.73 (1H, d, J=3.4 Hz), 6.81 (1H, d, J=1.4 Hz), 7.10–7.17 (6H, m), 7.25–7.7.34 (10H, m), 7.51 (1H, d, J=1.2 Hz), 7.56 (1H, dd, J=1.8, 8.6 Hz), 7.72 (1H, dd, J=1.7, 6.7 Hz), 7.75–7.82 (2H, m), 7.99 (1H, s), 7.08 (1H, s). IR (KBr): 3237, 2973, 1169, 1013, 747, 729, 702 cm$^{-1}$.

(ii) Production of 1-(6-(2-Furyl)-2-naphthyl)-1-(1H-imidazol-4-yl)-2-methyl-1-propanol In a similar manner to that described in Reference example 5, the reaction was carried out by using 1-(6-(2-furyl)-2-naphthyl)-2-methyl-1-(1-trityl-1H-imidazol-4-yl)-1-propanol (1.30 g) to give the titled compound (644 mg) as a pale yellow powder.

$^1$H-NMR (CDCl$_3$+CD$_3$OD) δ: 0.82 (3H, d, J=7.0 Hz), 1.02 (3H, d, J=6.6 Hz), 2.67–2.81 (1H, m), 6.52 (1H, dd, J=1.6, 3.2 Hz), 6.76 (1H, d, J=3.2 Hz), 7.01 (1H, d, J=1.2 Hz), 7.51–7.53 (2H, m), 7.59 (1H, dd, J=1.8, 8.4 Hz), 7.74 (1H, dd, J=1.8. 8.4 Hz), 7.83 (2H, m), 7.97 (1H, s), 8.09 (1H, s). IR (KBr): 3248, 2971, 1381, 1013, 984, 901, 831, 810, 754 cm$^{-1}$.

Example 3

Production of 1-(1H-Imidazol-4-yl)-2-methyl-1-(6-(2-thienyl)-2-naphthyl)-1-propanol (i) Production of 2-Methyl-1-(6-(2-thienyl)-2-naphthyl)-1-(1-trityl-1H-imidazol-4-yl)-1-propanol In a similar manner to that described in Example 2-(i), the reaction was carried out by using 6-[1-hydroxy-2-methyl-1-(1-trityl-1H-imidazol-4-yl)propyl]-2-naphthyl trifluoromethanesulfonate (2.0 g) and 2-(tributylstannyl)thiophene (1.27 mL) to give the titled compound (1.43 g) as a colorless powder.

$^1$H-NMR (CDCl$_3$) δ: 0.75 (3H, d, J=6.6 Hz), 0.96 (3H, d, J=6.6 Hz), 2.47–2.60 (1H, m), 3.71 (1H, s), 6.81 (1H, d, J=1.4 Hz), 7.09–7.17 (7H, m), 7.29–7.34 (11H, m), 7.41 (1H, dd, J=1.1, 3.7 Hz), 7.57 (1H, dd, J=1.6, 8.4 Hz), 7.71 (1H, dd, J=1.4, 8.4 Hz), 7.75 (1H, d, J=8.4 Hz), 7.80 (1H, d, J=8.4 Hz), 8.00 (2H, s). IR (KBr): 3194, 2969, 1491, 1445, 1015, 814, 756, 748, 698 cm$^{-1}$.

(ii) Production of 1-(1H-Imidazol-4-yl)-2-methyl-1-(6-(2-thienyl)-2-naphthyl)-1-propanol In a similar manner to that described in Reference example 5, the reaction was carried out by using 2-methyl-1-(6-(2-thienyl)-2-naphthyl-)-1-(1-trityl-1H-imidazol-4-yl)-1-propanol (1.20 g) to give the titled compound (607 mg) as a colorless powder.

¹H-NMR (CDCl₃+CD₃OD) δ: 0.82 (3H, d, J=6.4 Hz), 1.01 (3H, d, J=6.6 Hz), 2.66–2.76 (1H, m), 7.00 (1H, s), 7.11 (1H, dd, J=3.6, 5.0 Hz), 7.31 (1H, dd, J=1.0, 5.0 Hz), 7.42 (1H, dd, J=1.0, 3.6 Hz), 7.51 (1H, d, J=1.0 Hz), 7.59 (1H, dd, J=2.0, 8.8 Hz), 7.72 (1H, dd, J=2.0, 8.6 Hz), 7.77 (1H, d, J=8.6 Hz), 7.82 (1H, d, J=8.8 Hz), 7.99 (2H, s). IR (KBr): 3551, 3110, 2973, 1017, 941, 882, 826, 810, 702 cm⁻¹.

Example 4

Production of 1-(1H-Imidazol-4-yl)-2-methyl-1-(6-(1H-1,2,3-triazol-4-yl)-2-naphthyl)-1-propanol (i) Production of 2-Methyl-1-(6-(5-trimethylsilyl-1H-1,2,3-triazol-4-yl)-2-naphthyl)-1-(1-trityl-1H-imidazol-4-yl)-1-propanol To a solution of 6-(1-hydroxy-2-methyl-1-(1-trityl-1H-imidazol-4-yl)propyl)-2-naphthonitrile in THF (15 mL) was added a solution of n-butyllithium in hexane (1.6M:2.57 mL) under ice cooling, and the mixture was stirred for 20 min. A solution of trimethylsilyldiazomethane in THF (10% wt.:6.0 g) was added dropwise to the mixture and stirred for 90 min under ice cooling. The reaction mixture was diluted with saturated aq. ammonium chloride and extracted with ethyl acetate. The extract was washed with water and brine, dried and concentrated. The residue was purified by column chromatography (eluent; hexane:THF=1:1) and crystallized from ethyl acetate-hexane (1:1) to give the titled compound (881 mg) as a colorless powder.

¹H-NMR (CDCl₃+CD₃OD) δ: 0.34 (9H, s), 0.77 (3H, d, J=6.8 Hz), 0.98 (3H, d, J=6.8 Hz), 2.55–2.69 (1H, m), 6.86 (1H, d, J=1.4 Hz), 7.11–7.16 (6H, m), 7.33–7.38 (10H, m), 7.59 (1H, dd, J=1.7, 8.9 Hz), 7.69 (1H, dd, J=1.6, 8.6 Hz), 7.78 (1H, d, J=8.6 Hz), 7.88 (1H, d, J=8.2 Hz), 8.00–8.02 (2H, m). IR (KBr): 3551, 3055, 2963, 1481, 1445, 1252, 1173, 995, 841, 747, 702 cm⁻¹.

(ii) Production of 2-Methyl-1-(6-(1H-1,2,3-triazol-4-yl)-2-naphthyl)-1-(1-trityl-1H-imidazol-4-yl)-1-propanol A solution of tetrabutylammonium fluoride in THF (1M:3 mL) was added to a solution of 2-methyl-1-(6-(5-trimethylsilyl-1H-1,2,3-triazol-4-yl)-2-naphthyl)-1-(1-trityl-1H-imidazol-4-yl)-1-propanol (820 mg) in THF (3 mL) and the mixture was stirred at room temperature for 1 h. The reaction mixture was diluted with water and extracted with ethyl acetate. The organic layer was washed with water and brine, dried and concentrated. The residue was purified by column chromatography (eluent; hexane:THF=4:1) and crystallized from ethyl acetate-hexane to give the titled compound (703 mg) as a colorless powder.

¹H-NMR (CDCl₃+CD₃OD) δ: 0.78 (3H, d, J=6.6 Hz), 0.98 (3H, d, J=6.8 Hz), 2.63–2.77 (1H, m), 6.91 (1H, d, J=1.4 Hz), 7.11–7.18 (6H, m), 7.31–7.40 (10H, m), 7.64 (1H, dd, J=1.7, 8.7 Hz), 7.83 (1H, d, J=8.8 Hz), 7.89 (2H, s), 8.01 (1H, s), 8.07 (1H, s), 8.23 (1H, s). IR (KBr): 3584, 3058, 2973, 1480, 1445, 1171, 992, 748, 702 cm⁻¹.

(iii) Production of 1-(1H-Imidazol-4-yl)-2-methyl-1-(6-(1H-1,2,3-triazol-4-yl)-2-naphthyl)-1-propanol In a similar manner to that described In Reference example 5, the reaction was carried out by using 2-methyl-1-(6-(1H-1,2,3-triazol-4-yl)-2-naphthyl)-1-(1-trityl-1H-imidazol-4-yl)-1-propanol (680 mg) to give the titled compound (314 mg) as a colorless powder.

¹H-NMR (CDCl₃+CD₃OD) δ: 0.82 (3H, d, J=6.6 Hz), 1.02 (3H, d, J=6.8 Hz), 2.68–2.82 (1H, m), 7.03 (1H, s), 7.53 (1H, s), 7.61 (1H, dd, J=1.7, 8.7 Hz), 7.80 (1H, d, J=8.8 Hz), 7.87–7.91 (2H, m), 8.01 (2H, S), 8.20 (1H, s). IR (KBr): 3117, 2969, 1134, 999, 976, 897, 816 cm⁻¹.

Example 5

Production of 1-(1H-Imidazol-4-yl)-2-methyl-1-(6-(1H-1,2,3,4-tetrazol-5-yl)-2-naphthyl)-1-propanol (i) Production of 2-Methyl-1-(6-(1H-1H-1,2,3,4-tetrazol-5-yl)-2-naphthyl)-1-(1-trityl-1H-imidazol-4-yl)-1-propanol A solution of 6-(1-hydroxy-2-methyl-1-(1-trityl-1H-imidazol-4-yl)propyl)-2-naphthonitrile (1.0 g) and azidotrimethyltin (770 mg) in toluene (10 mL) was refluxed for 48 h. The precipitate was collected by filtration, dissolved in THF-methanol (1:1) and concentrated. The residue was diluted with water and extracted with a mixed solution of ethyl acetate-THF (1:1). The extract was dried and concentrated. The residue was purified by column chromatography (eluent; hexane:THF=1:3) and crystallized from ethyl acetate to give the titled compound (469 mg) as a pale yellow powder.

¹H-NMR (CDCl₃+CD₃OD) δ: 0.75 (3H, d, J=6.6 Hz), 0.98 (3H, d, J=6.8 Hz), 2.58–2.72 (1H, m), 6.90 (1H, d, J=1.4 Hz), 7.10–7.15 (6H, m), 7.33–7.38 (9H, m), 7.41 (1H, d, J=1.4 Hz), 6.65 (1H, dd, J=1.8, 8.7 Hz), 7.84 (1H, d, J=8.7 Hz), 7.91 (1H, d, J=8.6 Hz), 8.00–8.04 (2H, m), 8.46 (1H, s). IR (KBr): 3389, 3057, 2967, 1493, 1445, 1157, 1140, 1015, 748, 702 cm⁻¹.

(ii) Production of 1-(1H-Imidazol-4-yl)-2-methyl-1-(6-(1H-1,2,3,4-tetrazol-5-yl)-2-naphthyl)-1-propanol In a similar manner to that described in Reference example 5, the reaction was carried out by using 2-methyl-1-(6-(1H-1,2,3,4-tetrazol-5-yl)-2-naphthyl)-1-(1-trityl-1H-imidazol-4-yl)-1-propanol (400 mg) to give the titled compound (71 mg) as a colorless powder.

¹H-NMR (CD₃OD) δ: 0.82 (3H, d, J=6.6 Hz), 1.03 (3H, d, J=6.8 Hz), 2.78–2.92 (1H, m), 7.30 (1H, s), 7.66 (1H, dd, J=1.2, 8.6 Hz), 7.87–7.95 (2H, m), 8.09–8.17 (3H, m), 8.49 (1H, s). IR (KBr): 3140, 2973, 1497, 1441, 1356, 1252, 1140, 903, 841, 758 cm⁻¹.

Example 6

Production of 1-(1H-Imidazol-4-yl)-2-methyl-1-(6-(1H-pyrazol-4-yl)-2-naphthyl)-1-propanol (i) Production of 2-Methyl-1-(1-trityl-1H-imidazol-4-yl)-1-(6-(1-trityl-1H-pyrazol-4-yl)-2-naphthyl)-1-propanol In a similar manner to that described in Example 2-(i), the reaction was carried out by using 6-[1-hydroxy-2-methyl-1-(1-trityl-1H-imidazol-4-yl)propyl]-2-naphthyl trifluoromethanesulfonate (3.0 g) and 4-tributylstannyl-1-trityl-1H-pyrazole (5.48 g) to give the titled compound (3.54 g) as a pale brown powder.

¹H-NMR (CDCl₃) δ: 0.74 (3H, d, J=6.4 Hz), 0.95 (3H, d, J=6.6 Hz), 2.45–2.59 (1H, m), 3.72 (1H, s), 6.80 (1H, d, J=1.4 Hz), 7.10–7.35 (31H, m), 7.50 (1H, dd, J=1.6, 8.6 Hz), 7.53 (1H, dd, J=1.8, 8.4 Hz), 7.66–7.76 (3H, m), 7.82 (1H, s), 7.96 (1H, s), 8.05 (1H, s). IR (KBr): 3463, 3032, 2965, 1493, 1445, 1165, 747, 700 cm⁻¹.

(ii) Production of 1-(1H-Imidazol-4-yl)-2-methyl-1-(6-(1H-pyrazol-4-yl)-2-naphthyl)-1-propanol In a similar manner to that described in Reference example 5, the reaction was carried out by using 2-methyl-1-(1-trityl-1H-imidazol-4-yl)-1-(6-(1-trityl-1H-pyrazol-4-yl)-2-naphthyl)-1-propanol (3.0 g) to give the titled compound (935 mg) as a colorless powder.

¹H-NMR (DMSO-d₆) δ: 0.67 (3H, d, J=6.6 Hz), 0.85 (3H, s), 2.10–2.37 (1H, m), 5.04 (1H, s), 7.01 (1H, s), 7.55 (1H, s), 7.71–7.86 (4H, m), 8.03 (2H, s), 8.16 (2H, s), 11.22 (1H, s). IR (KBr): 3208, 2976, 1337, 1146, 1024 cm⁻¹.

Example 7

Production of 1-(1H-Imidazol-4-yl)-2-methyl-1-(6-(1,3-oxazol-5-yl)-2-naphthyl)-1-propanol (i) Production of 2-Methyl-1-(6-(1,3-oxazol-5-yl)-2-naphthyl)-1-(1-trityl-1H-imidazol-4-yl)-1-propanol A mixture of 6-(1-hydroxy-2-methyl-1-(1-trityl-1H-imidazol-4-yl)propyl)-2-naphthoaldehyde (2.0 g), tosylmethylisocyanide (800 mg) and $K_2CO_3$ (1.0 g) in methanol was refluxed for 2 h. The reaction mixture was diluted with water. The precipitate formed was collected and crystallized from THF-hexane to give the titled compound (1.39 g) as colorless powder.

$^1$H-NMR (CDCl$_3$) δ: 0.75 (3H, d, J=6.8 Hz), 0.97 (3H, d, J=6.6 Hz), 2.48–2.61 (1H, m), 3.74 (1H, s), 6.82 (1H, d, J=1.6 Hz), 7.11–7.15 (6H, m), 7.30–7.36 (10H, m), 7.44 (1H, s), 7.61 (1H, dd, J=1.8, 8.8 Hz), 7.69 (1H, dd, J=1.4, 8.4 Hz), 7.78 (1H, d, J=8.8 Hz), 7.84 (1H, d, J=8.4 Hz), 7.96 (1H, s), 8.04 (1H, s), 8.08 (1H, s). IR (KBr): 3258, 2971, 1489, 1169, 1015, 828, 818, 748, 702 cm$^{-1}$.

(ii) Production of 1-(1H-Imidazol-4-yl)-2-methyl-1-(6-(1,3-oxazol-5-yl)-2-naphthyl)-1-propanol In a similar manner to that described in Reference example 5, the reaction was carried out by using 2-methyl-1-(6-(1,3-oxazol-5-yl)-2-naphthyl)-1-(1-trityl-1H-imidazol-4-yl)-1-propanol (1.20 g) to give the titled compound (407 mg) as a colorless powder.

$^1$H-NMR (CDCl$_3$+CD$_3$OD) δ: 0.82 (3H, d, J=7.0 Hz), 1.02 (3H, d, J=6.6 Hz), 2.68–2.82 (1H, m), 7.02 (1H, s), 7.43 (1H, s), 7.52 (1H, s), 7.65 (1H, dd, J=1.4, 8.6 Hz), 7.70 (1H, dd, J=1.6, 8.4 Hz), 7.81 (1H, d, J=8.6 Hz), 7.88 (1H, d, J=8.4 Hz), 8.02 (s, 2H), 8.09 (1H, s). IR (KBr): 3227, 2971, 1138, 1028, 982, 955, 868, 818 cm$^{-1}$.

Example 8

Production of Methyl 6-(1-Hydroxy-1-(1H-imidazol-4-yl)-2-methylpropyl)-2-naphthoate (i) Production of Methyl 6-(1-Hydroxy-2-methyl-1-(1-trityl-1H-imidazol-4-yl)propyl)-2-naphthoate 6-[1-hydroxy-2-methyl-1-(1-trityl-1H-imidazol-4-yl)propyl]-2-naphthyl trifluoromethanesulfonate (7.0 g), [(1,1'-bis(diphenylphosphino)ferrocene)]dichloropalladium complex with dichloromethane (441 mg) and triethylamine (2.98 mL) were dissolved in a mixed solution of DMF-methanol (1:1, 80 mL) and stirred at 60° C. for 10 h under carbon monoxide atmosphere. After removal of the solvent, the residue was diluted with water and extracted with ethyl acetate. The organic layer was washed with water and brine, dried and concentrated. The residue was purified by column chromatography (eluent; hexane:THF=1:2) to give the titled compound (5.65 g) as a pale yellow powder.

$^1$H-NMR (CDCl$_3$) δ: 0.74 (3H, d, J=7.0 Hz), 0.97 (3H, d, J=6.6 Hz), 2.47–2.61 (1H, m), 3.75 (1H, s), 3.97 (3H, s), 6.82 (1H, d, J=1.2 Hz), 7.10–7.16 (6H, m), 7.29–7.35 (10H, m), 7.62 (1H, dd, J=1.8, 8.6 Hz), 7.81 (1H, d, J=3.2 Hz), 7.85 (1H, d, J=3.2 Hz), 8.02 (1H, dd, J=1.8 Hz, 8.6 Hz), 8.07 (1H, s), 8.55 (1H, s). IR (Kr): 3542, 2965, 1707, 1441, 1279, 1231, 747, 700 cm$^{-1}$.

(ii) Production of Methyl 6-(1-Hydroxy-1-(1H-imidazol-4-yl)-2-methyl-propyl)-2-naphthoate In a similar manner to that described in Reference example 5, the reaction was carried out by using 6-(1-hydroxy-2-methyl-1-(1-trityl-1H-imidazol-4-yl)propyl)-2-naphthoate (1.40 g) to give the titled compound (751 mg) as a pale yellow powder.

$^1$H-NMR (CDCl$_3$+CD$_3$OD) δ: 0.80 (3H, d, J=7.0 Hz), 1.02 (3H, d, J=6.6 Hz), 2.69–2.82 (1H, m), 3.97 (3H, s), 7.02 (1H, d, J=1.2 Hz), 7.52 (1H, d, J=1.2 Hz), 7.68 (1H, dd, J=1.0, 8.4 Hz), 7.87 (2H, d, J=8,4 Hz), 8.01 (1H, dd, J=1.0, 8.4 Hz), 8.08 (1H, s), 8.55 (1H, s). IR (KBr): 3542, 2965, 1707, 1441, 1279, 1231, 747, 700 cm$^{-1}$.

Example 9

Production of 6-(1-Hydroxy-1-(1H-imidazol-4-yl)-2-methyl-propyl)-N-methyl-2-naphthamide (i) Production of 6-(1-Hydroxy-2-methyl-1-(1-trityl-1H-imidazol-4-yl) propyl)-N-methyl-2-naphthamide To a solution of methyl 6-(1-hydroxy-2-methyl-1-(1-trityl-1H-imidazol-4-yl)propyl)-2-naphthoate (1.80 g) in THF (20 mL) was added methanol (4 mL) and 4N-NaOH (20 mL) at 50° C. The mixture was stirred for 90 min, neutralized with conc. HCl. The mixture was concentrated, diluted with water and extracted with ethyl acetate. The extract was concentrated to give crude mixture of 6-(1-hydroxy-2-methyl-1-(1-trityl-1H-imidazol-4-yl)propyl)-2-naphthoic acid. To a solution of the crude mixture was added methylamine in THF (2.0M:3.50 mL), 1-hydroxybenzotriazole (536 mg) and 1-(3-dimethylaminopropyl)-3-ethylcarbodiimide hydrochloride (671 mg) under ice cooling. The mixture was stirred at room temperature for 20 h, diluted with water and extracted with ethyl acetate. The extract was concentrated and purified by column chromatography (eluent; hexane:THF=1:2) followed by crystallization from hexane-ethyl acetate to give the titled compound (1.55 g) as a pale yellow powder.

$^1$H-NMR (CDCl$_3$+CD$_3$OD) δ: 0.75 (3H, d, J=6.6 Hz), 0.97 (1H, d, J=7.0 Hz), 2.60–2.74 (1H, m), 3.01 (1H, d, J=4.4 Hz), 6.89 (1H, s), 7.10–7.14 (6H, m), 7.27–7.38 (10H, m), 7.65 (1H, dd, J=1.4, 8.8 Hz), 7.82–7.86 (3H, m), 8.03 (1H, s), 8.28 (1H, s). IR (KBr): 3345, 2969, 1657, 1443, 1302, 1011, 747, 700 cm$^{-1}$.

(ii) Production of 6-(1-Hydroxy-1-(1H-imidazol-4-yl)-2-methylpropyl)-N-methyl-2-naphthamide In a similar manner to that described in Reference example 5, the reaction was carried out by using 6-(1-hydroxy-2-methyl-1-(1-trityl-1H-imidazol-4-yl)propyl)-N-methyl-2-naphthamide (1.30 g) to give the titled compound (424 mg) as a colorless powder.

$^1$H-NMR (CDCl$_3$+CD$_3$OD) δ: 0.78 (3H, d, J=7.0 Hz), 1.01 (3H, d, J=6.6 Hz), 2.67–2.80 (1H, m), 3.00 (3H, s), 7.00 (1H, d, J=1.2 Hz), 7.49 (1H, d, J=1.0 Hz), 7.63 (1H, dd, J=1.8, 8.8 Hz), 7.74–7.79 (2H, m), 7.83 (1H, d, J=8.4 Hz), 8.03 (1H, s), 8.22 (1H, s). IR (KBr): 3565, 3351, 3318, 2973, 1638, 1628, 1549, 1308, 993 cm$^{-1}$.

Example 10

Production of 6-(1-Hydroxy-1-(1H-imidazol-4-yl)-2-methyl-propyl)-N-methoxy-2-naphthamide (i) Production of 6-(1-Hydroxy-2-methyl-1-(1-trityl-1H-imidazol-4-yl)propyl)-N-methoxy-2-naphthamide In a similar manner to that described in Example 9-(i), a crude mixture of 6-(1-hydroxy-2-methyl-(1-trityl-1H-imidazol-4-yl)propyl)-2-naphthoic acid was obtained by the reaction using methyl 6-(1-hydroxy-2-methyl-1-(1-trityl-1H-imidazol-4-yl)propyl)-2-naphthoate (2.0 g). To a solution of the crude mixture in THF (30 mL) was added methoxyamine hydrochloride (354 mg), 1-hydroxybenzotriazole (594 mg) and 1-(3-dimethylaminopropyl)-3-ethylcarbodiimide hydrochloride (744 mg) under ice cooling. The mixture was stirred at room temperature for 15 h, diluted with water and extracted with ethyl acetate. The extract was concentrated and purified by column chromatography (eluent; hexane:THF=1:2) followed by crystallization from hexane-ethyl acetate to give the titled compound (1.90 g) as a pale yellow powder.

$^1$H-NMR (CDCl$_3$) δ: 0.74 (3H, d, J=6.6 Hz), 0.97 (3H, d, J=6.6 Hz), 2.58–2.71 (1H, m), 3.95 (3H, s), 6.88 (1H, d, J=1.4 Hz), 7.10–7.14 (6H, m), 7.30–7.35 (10H, m), 7.64 (1H, dd, J=1.8, 8.8 Hz), 7.77 (1H, dd, J=1.6, 8.8 Hz), 7.83 (3H, d, J=8.8 Hz), 7.85 (3H, d, J=8.8 Hz), 8.02 (1H, s), 8.25 (1H, s). IR (KBr): 3347, 2967, 1736, 1661, 1493, 1445, 1244, 812, 745, 700 cm$^{-1}$.

(ii) Production of 6-(1-Hydroxy-1-(1H-imidazol-4-yl)-2-methyl-propyl)-N-methoxy-2-naphthamide In a similar manner to that described in Reference example 5, the reaction was carried out by using 6-(1-hydroxy-2-methyl-1-(1-trityl-1H-imidazol-4-yl)propyl)-N-methoxy-2-naphthamide (1.60 g) to give the titled compound (655 mg) as a colorless powder.

$^1$H-NMR (CDCl$_3$+CD$_3$OD) δ: 0.79 (3H, d, J=6.6 Hz), 1.01 (3H, d, J=6.6 Hz), 2.69–2.80 (1H, m), 3.84 (3H, s), 7.03 (1H, d, J=1.0 Hz), 7.52 (1H, d, J=1.2 Hz), 7.67 (1H, dd, J=1.8, 8.8 Hz), 7.73–7.78 (2H, m), 7.86 (1H, d, J=8.4 Hz), 8.05 (1H, s), 8.23 (1H, s). IR (KBr): 3418, 3243, 2967, 1634, 1622, 1011 cm$^{-1}$.

Example 11

Production of 1-(1H-Imidazol-4-yl)-1-(naphtho[2,1-b]furan-7-yl)-2-methyl-1-propanol (i) Production of 2-Bromo-6-(2,2-diethoxyethoxy)naphthalene A mixture of 6-bromo-2-naphthol (25.07 g), bromoacetaldehydediethylacetal (21 mL) and K$_2$CO$_3$ (19.80 g) in DMF (100 mL) was heated at 110° C. for 20 h. After removal of solvent, ethyl acetate and water were add to the residue. The organic layer was washed with water and brine, dried and concentrated. The residue was chromatographed on silica gel(eluent; hexane:ethyl acetate=10:1) followed by crystallization from hexane to give the titled compound (15.63 g) as a colorless solid. The titled compound (13.86 g) was recovered from the mother liquor.

$^1$H-NMR (CDCl$_3$) δ: 1.27 (6H, t, J=7.1 Hz), 3.57–3.89 (4H, m), 4.11 (2H, d, J=5.3 Hz), 4.90 (1H, t, J=5.3 Hz), 7.11 (1H, d, J=2.6 Hz), 7.20 (1H, dd, J=8.8, 2.6 Hz), 7.45–7.68 (3H, m), 7.91 (1H, d, J=1.8 Hz). IR (KBr): 2976, 2880, 1626, 1590, 1501, 1211, 1074 cm$^{-1}$.

(ii) Production of 7-Bromonaphtho[2,1-b]furan

A solution of 2-bromo-6-(2,2-diethoxyethoxy)naphthalene (13.86 g) in toluene (150 mL) was added dropwise to a mixture of polyphosphoric acid (32 g) and toluene (150 g) at 100° C. with vigorous stirring. The mixture was refluxed for 1 h. 1N-NaOH (200 mL) was added to the mixture and the whole was extracted with ethyl acetate.

The organic layer was concentrated and the residue was crystallized with hexane to give the titled compound (6.54 g) as a colorless solid.

$^1$H-NMR (CDCl$_3$) δ: 7.24 (1H, d, J=2.2 Hz), 7.59–7.77 (3H, m), 7.78 (1H, d, J=2.2 Hz), 8.01 (1H, d, J=8.6 Hz), 8.11 (1H, d, J=1.8 Hz). IR (KBr): 3401, 1505, 1136, 820 cm$^{-1}$.

(iii) Production of (Naphtho[2,1-b]furan-7-yl)(1-trityl-1H-imidazol-4-yl)methanol Iodomethyl (0.05 mL) was added to mixture THF (5 mL) and magnesium (turnings, 0.719 g) with stirring. 7-bromonaphtho[2,1-b]furan (6.09 g) was added and the mixture was refluxed for 2 h. The resulting mixture was cooled to 0° C. and a solution of 4-formyl-1-trityl-1H-imidazole (4.71 g) in THF (40 mL) was added. The mixture was stirred at room temperature for 1 h and aq. ammonium chloride was added. The mixture was extracted with ethyl acetate, dried and concentrated. The residue was chromatographed on silica gel (eluent; hexane:ethyl acetate= 2:1→1:2) to give the titled compound (2.30 g) as a colorless solid.

$^1$H-NMR (CDCl$_3$) δ: 3.81 (1H, br s), 5.96 (1H, s), 6.63 (1H, m), 7.07–7.36 (17H, m), 7.43 (1H, d, J=1.4 Hz), 7.60 (1H, dd, J=8.4, 2.0 Hz), 7.65 (1H, d, J=1.4 Hz), 7.74 (1H, d, J=2.0 Hz), 7.97 (1H, d, J=2.0 Hz), 8.05 (1H, d, J=8.4 Hz). IR (KBr): 3061, 1493, 1445, 1132, 909, 702 cm$^{-1}$.

(iv) Production of (Naphtho[2,1-b]furan-7-yl)(1-trityl-1H-imidazol-4-yl)ketone

MnO$_2$ (3.22 g) was added to a solution of (naphtho[2,1-b]furan-7-yl)(1-trityl-1H-imidazol-4-yl)methanol (2.30 g) in dichloromethane (50 ml) and stirred at room temperature for 14 h. The reaction mixture was filtered with celite and the filtrate was concentrated in vacuo. The residue was crystallized from ethyl acetate to give the titled compound (2.14 g) as a colorless solid.

$^1$H-NMR (CDCl$_3$) δ: 7.12–7.44 (16H, m), 7.60 (1H, s), 7.70 (1H, d, J=8.8 Hz), 7.75–7.82 (2H, m), 7.85 (1H, d, J=8.8 Hz), 8.18 (1H, d, J=8.5 Hz), 8.40 (1H, d, J=8.5 Hz), 9.10 (1H, s). IR (KBr): 1622, 1520, 1235, 1167, 702 cm$^{-1}$.

(v) Production of (1H-Imidazol-4-yl)(naphtho[2,1-b]furan-7-yl)ketone

A mixture of (naphtho[2,1-b]furan-7-yl)(1-trityl-1H-imidazol-4-yl)ketone (1.88 g) and pyridinium chloride (0.72 g) in methanol was heated at 60° C. for 2 h. Saturated sodium bicarbonate solution was added to the mixture and concentrated. Water and diethyl ether were added to the residue. The precipitate was washed with water and diethyl ether to give the titled compound (0.86 g) as a colorless solid.

$^1$H-NMR (DMSO-d$_6$) δ: 7.67 (1H, d, J=2.0 Hz), 7.85–8.10 (4H, m), 8.19 (1H, d, J=2.0 Hz), 8.20–8.32 (2H, m), 8.43 (1H, d, J=8.8 Hz), 8.96 (1H, br s). IR (KBr): 3204, 1626, 1418, 1163, 760 cm$^{-1}$.

(vi) Production of 1-(1H-Imidazol-4-yl)-1-(naphtho[2,1-b]furan-7-yl)-2-methyl-1-propanol A solution of isopropyl-magnesium chloride in THF (0.9M; 12 mL) was added dropwise to a solution of (naphtho[2,1-b]furan-7-yl)(1-1H-imidazol-4-yl)ketone (0.71 g) in THF (40 ml) at 0° C. The mixture was warmed to room temperature and stirred for 2 h. Saturated ammonium chloride solution was added to the mixture and the whole was extracted with ethyl acetate. The extract was dried and concentrated. The residue was chromatographed on silica gel (eluent; dichloromethane:methanol=30:1) to give the titled compound (0.54 g) as an amorphous powder.

$^1$H-NMR (CDCl$_3$) δ: 0.81 (3H, d, J=6.8 Hz), 1.02 (3H, d, J=6.8 Hz), 2.74 (1H, m), 3.20–3.80 (2H, m), 7.02 (1H, s), 7.22 (1H, d, J=2.0 Hz), 7.53 (1H, s), 7.59–7.77 (4H, m), 8.06 (1H, d, J=8.6 Hz), 8.16 (1H, d, J=1.8 Hz). IR (KBr): 3127, 2975, 909, 824, 737 cm$^{-1}$.

Example 12

Production of 1-(1,2-Dihydronaphtho[2,1-b]furan-7-yl)-1-(1H-imidazol-4-yl)-2-methyl-1-propanol A mixture of 1-(1H-imidazol-4-yl)-1-(naphtho[2,1-b]furan-7-yl)-2-methyl-1-propanol (0.310 g) and 5% rhodium carbon (1.50 g) in acetic acid (50 mL) was stirred at room temperature for 7 h under hydrogen atmosphere at 4 atom pressure. Catalyst was filtered off, and the filtrate was concentrated. The residue was dissolved in ethyl acetate, washed with saturated sodium bicarbonate solution and brine, dried and concentrated. The residue was chromatographed on silica gel (eluent; dichloromethane:methanol= 20:1) followed by crystallization from ethyl acetate to give the titled compound (0.107 g) as a colorless solid.

$^1$H-NMR (CDCl$_3$) δ: 0.81 (3H, d, J=6.6 Hz), 1.00 (3H, d, J=6.6 Hz), 2.61–2.78 (1H, m), 3.45 (2H, t, J=9.0 Hz), 4.74 (2H, t, J=9.0 Hz), 6.98 (1H, t, J=0.8 Hz), 7.08 (1H, t, J=8.8 Hz), 7.46–7.78 (4H, m), 7.99 (1H, d, J=1.6 Hz). IR (KBr): 3125, 2967, 1470, 1244, 970, 909, 731 cm$^{-1}$.

Example 13

Production of 1-(1H-Imidazol-4-yl)-1-(naphtho[2,3-d][1,3]-dioxol-6-yl)-2-methyl-1-propanol (i) Production of Ethyl Naphtho[2,3-d][1.3]dioxol-6-carboxylate A solution of lithium diisopropylamide in THF (2M; 60 mL) was diluted with THF (100 mL) and cooled to −78° C. A solution of piperonal (14.50 g) in THF (30 mL) was added to the solution and stirred at −78° C. for 1 h. A solution of ethyl 1,3-dioxan-3-propanoate (18.05 g) was added dropwise to the mixture and stirred at −78° C. for 1 h. The mixture was allowed to room temperature and to which was added saturated ammonium chloride solution. The whole was extracted with ethyl acetate and the organic layer was washed with brine, dried and concentrated. The residue was chromatographed on silica gel (eluent; hexane:ethyl acetate=2:1) to give an oily product (19.60 g). The oily product was dissolved in toluene (50 mL) and heated with polyphosphoric acid (39.70 g) at 100° C. for 30 min. Water was added and the mixture was neutralized with 1N-NaOH solution, extracted with ethyl acetate. The organic layer was washed with brine, dried and concentrated. The residue was chromatographed on silica gel (eluent; hexane:ethyl acetate=1:1) followed by crystallization from hexane-diisopropyl ether to give the titled compound (5.83 g) as a pale yellow solid.

$^1$H-NMR (CDCl$_3$) δ: 1.43 (3H, t, J=7.1 Hz), 4.41 (2H, q, J=7.1 Hz), 6.07 (2H, s), 7.14 (1H, s), 7.20 (1H, s), 7.67 (1H, d, J=8.6 Hz), 7.92 (1H, dd, J=8.6, 1.2 Hz), 8.40 (1H, d, J=1.2 Hz). IR (KBr): 2905, 1713, 1470, 1240, 1206, 1040 cm$^{-1}$.

(ii) Production of (Naphtho[2,3-d][1,3]dioxol-6-yl) methanol

Ethyl naphtho[2,3-d][1,3]dioxol-6-carboxylate (5.43 g) was added to a mixture of lithium aluminum hydride (1.10 g) and THF (50 mL) at 0° C. The mixture was stirred at room temperature for 1 h. Potassium sodium tartrate solution was added to the mixture and the whole was extracted with ethyl acetate. The organic layer was concentrated and the residue was crystallized from ethyl acetate to give the titled compound (3.21 g) as a colorless solid.

$^1$H-NMR (CDCl$_3$) δ: 1.61 (1H, br s), 4.80 (2H, s), 6.04 (2H, s), 7.11 (2H, s), 7.33 (1H, dd, J=8.4, 1.8 Hz), 7.61–7.69 (2H, m). IR (KBr): 3237, 2909, 1478, 1260, 932 cm$^{-1}$.

(iii) Production of 6-Formylnaphtho[2,3-d][1,3]dioxol

MnO$_2$ (5.90 g) was added to a solution of (naphtho[2,3-d][1,3]dioxol-6-yl)methanol (3.40 g) in dichloromethane (100 ml) and stirred at room temperature for 24 h. Insoluble material was filtered off and the filtrate was concentrated in vacuo. The residue was crystallized from hexane-ethyl acetate to give the titled compound (3.16 g) as a colorless solid.

$^1$H-NMR (CDCl$_3$) δ: 6.11 (2H, s), 7.17 (1H, s), 7.24 (1H, s), 7.73 (1H, d, J=8.4 Hz), 7.81 (1H, m), 8.14 (1H, s), 10.08 (1H, s). IR (KBr): 1698, 1474, 1260, 1182, 1042, 864 cm$^{-1}$.

(iv) Production of (1H-Imidazol-4-yl)(6-formylnaphtho[2,3-d][1,3]dioxol-6-yl)ketone A solution of 4-bromo-1H-imidazole (2.00 g) in THF (30 ml) was cooled to −78° C. A solution of tert-butyllithium in pentane (1.7 M; 22 ml) was added to the solution. The mixture was stirred at 0° C. for 1.5 h and then cooled to −78° C. 6-formylnaphtho[2,3-d][1,3]dioxol (3.00 g) in THF (30 ml) was added to the mixture. The mixture was allowed to room temperature and was stirred for 16 h. Ammonium chloride solution was added to the mixture and precipitate was collected, washed with water and ethyl acetate to give the titled compound (1.10 g) as a colorless solid.

$^1$H-NMR (DMSO-d$_6$) δ: 6.19 (2H, s), 7.40 (1H, s), 7.52 (1H, s), 7.70–8.18 (5H, m) IR (KBr): 3142, 1632, 1478, 1254, 872 cm$^{-1}$.

(v) Production of 1-(1H-Imidazol-4-yl)-1-(6-formylnaphtho[2,3-d][1,3]dioxol-6-yl)-2-methyl-1-propanol In a similar manner to that described in Example 11-(vi), the reaction was carried out by using (1H-imidazol-4-yl)(6-formylnaphtho[2,3-d][1,3]dioxol-6-yl)ketone (0.911 g) to give the titled compound (490 mg) as a colorless solid.

$^1$H-NMR (CDCl$_3$) δ: 0.80 (3H, d, J=6.8 Hz), 1.00 (3H, d, J=6.8 Hz), 2.56–2.80 (1H, m), 6.01 (2H, s), 7.00 (1H, s), 7.07 (1H, s), 7.10 (1H, s), 7.40–7.64 (3H, m), 7.87 (1H, s). IR (KBr): 3071, 2967, 1470, 1238, 1040 cm$^{-1}$.

Example 14

Production of 1-(2,3-Dihydro-1H-benzo[f]chromen-8-yl)-1-(1H-imidazol-4-yl)-2-methyl-1-propanol (i) Production of 2-Allyloxy-6-bromonaphthalene 6-bromo-2-naphthol (76.1 g) was added to a suspension of NaH (60% oil dispersion, 14.7 g) in DMF (500 ml) under ice cooling. The mixture was stirred at 5° C. for 1 h. 3-bromo-1-propene (42.7 g) was added to the mixture and stirred at room temperature for 2 h. The solvent was evaporated and the residue was dissolved in ethyl acetate. The organic layer was washed with water and brine, dried and concentrated. The residue was crystallized from hexane to give the titled compound (49.30 g) as a colorless solid.

$^1$H-NMR (CDCl$_3$) δ: 4.60–4.70 (2H, m), 5.26–5.54 (2H, m), 6.00–6.23 (1H, m), 7.10 (1H, d, J=2.6 Hz), 7.19 (1H, dd, J=8.9, 2.6 Hz), 7.49 (1H, dd, J=8.9, 1.8 Hz), 7.59 (1H, d, J=8.9 Hz), 7.65 (1H, d, J=8.9 Hz), 7.92 (1H, d, J=1.8 Hz). IR (KBr): 2901, 1591, 1499, 1458, 1262, 1022 cm$^{-1}$.

(ii) Production of 1-Allyl-6-bromonaphthalen-2-ol

2-Allyloxy-6-bromonaphthalene (49.30 g) was heated at 190° C. for 3 h to give the titled compound (48.90 g) as a brown solid.

$^1$H-NMR (CDCl$_3$) δ: 3.79 (2H, dt, J=5.4, 1.6 Hz), 4.95–5.16 (3H, m), 5.92–6.16 (1H, m), 7.10 (1H, d, J=9.1 Hz), 7.52 (1H, dd, J=8.8, 2.2 Hz), 7.57 (1H, d, J=9.1 Hz), 7.76 (1H, d, J=8.8 Hz), 7.92 (1H, d, J=2.2 Hz). IR (KBr): 3314, 1590, 1497, 1346, 1204, 878 cm$^{-1}$.

(iii) Production of 6-Bromo-1-(3-hydroxypropyl) naphthalen-2-ol

A solution of 1-allyl-6-bromo-naphthalen-2-ol (23.80 g) in THF (400 mL) was cooled at 0° C. A solution of 9-BBN (9-borabicyclo[3.3.1]nonane) in THF (0.5M; 400 mL) was added dropwise to the solution and the resulting mixture was stirred at room temperature for 60 h. 3N-NaOH solution (100 mL) and hydrogen peroxide solution (30%; 100 mL) were added. The mixture was stirred at room temperature for 4 h and was extracted with ethyl acetate. The organic layer was washed with brine, dried and concentrated. The residue was chromatographed on silica gel (eluent; hexane-ethyl acetate=1:1) to give the titled compound (22.27 g) as a colorless solid.

$^1$H-NMR (CDCl$_3$) δ: 1.90–2.08 (2H, m), 3.12–3.25 (2H, m), 3.62 (2H, t, J=5.7 Hz), 7.16 (1H, d, J=8.8 Hz), 7.52 (1H, dd, J=9.2, 2.2 Hz), 7.55 (1H, d, J=8.8 Hz), 7.75 (1H, d, J=9.2 Hz), 7.91 (1H, d, J=2.2 Hz). IR (KBr): 3175, 1590, 1501, 1264 cm$^{-1}$.

(iv) Production of 8-Bromo-2,3-dihydro-1H-benzo[f] chromene

A mixture of 6-bromo-1-(3-hydroxypropyl)naphthalene-2-ol (22.27 g) and p-toluenesulfonic acid monohydrate (0.43 g) in toluene was refluxed for 6 h. The mixture was diluted with ethyl acetate, washed with saturated sodium bicarbonate solution and brine, dried and concentrated. The residue was chromatographed on silica gel (eluent; hexane:ethyl acetate=5:1) to give the titled compound (13.35 g) as a colorless solid.

¹H-NMR (CDCl₃) δ: 1.98–2.15 (2H, m), 2.92 (2H, t, J=6.6 Hz), 4.16 (2H, t, J=5.3 Hz), 6.96 (1H, d, J=9.0 Hz), 7.41 (1H, d, J=9.0 Hz), 7.43 (1H, dd, J=8.9, 2.0 Hz), 7.56 (1H, d, J=8.9 Hz), 7.80 (1H, d, J=2.0 Hz). IR (KBr): 2948, 1590, 1497, 1397, 1240, 1096, 804 cm⁻¹.

(v) Production of (2,3-Dihydro-1H-benzo[f]chromen-8-yl)(1-trityl-1H-imidazol-4-yl)methanol n-Butyl-lithium in hexane (1.6M; 41 mL) was added to a solution of 8-bromo-2,3-dihydro-1H-benzo[f]chromene (13.35 g) in THF (250 ml) at −78° C. and stirred at the same temperature for 30 min. A solution of 4-formyl-1-trityl-1H-imidazole (16.83 g) in THF (150 ml) was added to the mixture and the whole was allowed to room temperature. Aqueous ammonium chloride solution was added to the mixture and extracted with ethyl acetate. The organic layer was washed with brine, dried and concentrated. The residue was washed with ethyl acetate to give the titled compound (11.80 g) as a colorless solid.

¹H-NMR (CDCl₃+CD₃OD) δ: 2.06–2.24 (2H, m), 3.02 (2H, t, J=6.5 Hz), 3.75 (1H, m), 4.23 (2H, t, J=5.1 Hz), 5.88 (1H, s), 6.68 (1H, s), 7.01 (1H, d, J=9.0 Hz), 7.06–7.17 (6H, m), 7.25–7.37 (9H, m), 7.42 (1H, d, J=1.6 Hz), 7.48 (1H, dd, J=8.8, 1.6 Hz), 7.55 (1H, d, J=8.8 Hz), 7.70–7.78 (2H, m). IR (KBr): 3056, 1603, 1480, 1240, 1127, 702 cm⁻¹.

(vi) Production of (2,3-Dihydro-1H-benzo[f]chromen-8-yl)(1-trityl-1H-imidazol-4-yl)ketone In a similar manner to that described in Example 11-(iv), the reaction was carried out by using (2,3-dihydro-1H-benzo[f]chromen-8-yl)(1-trityl-1H-imidazol-4-yl)methanol (11.50 g) to give the titled compound (9.11 g) as a colorless solid.

¹H-NMR (CDCl₃) δ: 2.08–2.24 (2H, m), 3.06 (2H, t, J=6.4 Hz), 4.27 (2H, t, J=5.1 Hz), 7.05 (1H, d, J=8.8 Hz), 7.12–7.23 (6H, m), 7.32–7.43 (9H, m), 7.58 (1H, d, J=1.5 Hz), 7.71 (1H, d, J=8.8 Hz), 7.76 (1H, d, J=1.5 Hz), 7.83 (1H, d, J=8.8 Hz), 8.29 (1H, dd, J=8.8, 1.8 Hz), 8.90 (1H, d, J=1.8 Hz). IR (KBr): 3061, 1615, 1520, 1476, 1240, 1179, 702 cm⁻¹.

(vii) Production of (2,3-Dihydro-1H-benzo[f]chromen-8-yl)(1H-imidazol-4-yl)ketone In a similar manner to that described in Example 11-(v), the reaction was carried out by using (2,3-dihydro-1H-benzo[f]chromen-8-yl)(1-trityl-1H-imidazol-4-yl)ketone (8.90 g) to give the titled compound (629 mg) as a colorless powder.

¹H-NMR (DMSO-d₆) δ: 1.96–2.18 (2H, m), 3.03 (2H, t, J=6.5 Hz), 4.25 (2H, t, J=4.9 Hz), 7.11 (1H, d, J=9.2 Hz), 7.82–8.03 (4H, m), 8.14 (1H, d, J=8.8 Hz), 8.79 (1H, br s). IR (KBr): 3144, 1634, 1345, 1240, 853 cm⁻¹.

(viii) Production of 1-(2,3-Dihydro-1H-benzo[f]chromen-8-yl)-1-(1H-imidazol-4-yl)-2-methyl-1-propanol In a similar manner to that described in Example 11-(vi), the reaction was carried out by using (2,3-dihydro-1H-benzo[f]chromen-8-yl)(1H-imidazol-4-yl)ketone (2.43 g) to give the titled compound (1.65 g) as a colorless powder.

¹H-NMR (CDCl₃) δ: 0.79 (3H, d, J=6.8 Hz), 0.98 (3H, d, J=6.8 Hz), 2.00–2.20 (2H, m), 2.56–2.74 (1H, m), 3.00 (2H, t, J=6.4 Hz), 4.21 (2H, t, J=5.1 Hz), 6.89 (1H, d, J=1.2 Hz), 6.99 (1H, d, J=8.8 Hz), 7.35 (1H, d, J=1.2 Hz), 7.50–7.60 (2H, m), 7.70 (1H, d, J=8.6 Hz), 7.90 (1H, d, J=1.8 Hz). IR (KBr): 2969, 1601, 1478, 1240, 1096, 814, 733 cm⁻¹.

Example 15

Production of 1-(2,3-Dihydro-1H-benzo[f]chromen-8-yl)-1-(1H-imidazol-4-yl)ethanol A solution of methylmagnesium chloride in diethyl ether (3M; 3 mL) was added to a solution of (2,3-dihydro-1H-benzo[f]chromen-8-yl)(1H-imidazol-4-yl)ketone (0.50 g) in THF (20 ml) at 0° C. The mixture was stirred at room temperature for 3 h. Aqueous ammonium chloride solution was added to the mixture and extracted with ethyl acetate. The extract was dried and concentrated. The residue was washed with ethyl acetate to give the titled compound (0.49 g) as a colorless solid.

¹H-NMR (CDCl₃+CD₃OD) δ: 1.94 (3H, s), 2.06–2.24 (2H, m), 3.03 (2H, t, J=6.6 Hz), 4.24 (2H, t, J=5.2 Hz), 6.86 (1H, d, J=1.0 Hz), 7.01 (1H, d, J=8.8 Hz), 7.46–7.62 (3H, m), 7.75 (1H, d, J=8.8 Hz), 7.80 (1H, d, J=1.8 Hz). IR (KBr): 3085,1603, 1480, 1242, 1096, 808 cm⁻¹.

Example 16

Production of 1-(2,3-Dihydro-1H-benzo[f]chromen-8-yl)-1-(1H-imidazol-4-yl)propanol A solution of ethylmagnesium chloride in THF (3M; 3 mL) was added to a solution of (2,3-dihydro-1H-benzo[f]chromen-8-yl)(1H-imidazol-4-yl)ketone (0.523 g) in THF (20 ml) at 0° C. The mixture was stirred at room temperature for 2 h. Aqueous ammonium chloride solution was added to the mixture and extracted with ethyl acetate. The extract was dried and concentrated. The residue was chromatographed on silica gel (eluent; dichloromethane:methanol=20:1) to give the titled compound (0.512 g) as a colorless solid.

¹H-NMR (CDCl₃) δ: 0.84 (3H, t, J=7.3 Hz), 2.00–2.38 (4H, m), 3.00 (2H, t, J=6.4 Hz), 4.22 (2H, t, J=4.9 Hz), 4.40–5.20 (2H, br), 6.77 (1H, s), 6.99 (1H, d, J=8.8 Hz), 7.30 (1H, s), 7.42 (1H, dd, J=9.2, 1.5 Hz), 7.53 (1H, d, J=9.2 Hz), 7.69 (1H, d, J=8.8 Hz), 7.83 (1H, d, J=1.5 Hz). IR (KBr): 3123, 2973, 1603, 1478, 1248, 1096 cm⁻¹.

Example 17

Production of 1-(1,2-Dihydronaphtho[2,1-b]furan-7-yl)-1-(1H-imidazol-4-yl)-1-ethanol (i) Production of 6-bromo-1-(2-hydroxyethyl)-2-naphthol Ozone gas was introduced to a solution of 1-allyl-6-bromo-2-naphthol (3.29 g) in methanol (100 ml) at −78° C. for 4 h. NaBH₄ was added to the mixture, and the whole was allowed to warm to room temperature and concentrated. The residue was diluted with water and extracted with ethyl acetate, dried and concentrated. The residue was purified by silica gel chromatography (eluent; hexane:ethyl acetate=3:1) followed by crystallization from hexane-ethyl acetate to give the titled compound (0.805 g) as a colorless solid.

¹H-NMR (CDCl₃) δ: 2.32 (1H, brs), 3.30 (2H, t, J=5.4 Hz), 4.09 (2H, t, J=5.4 Hz), 7.20 (1H, d, J=8.8 Hz), 7.51 (1H, dd, J=2.2, 9.2 Hz), 7.58 (1H, d, J=8.8 Hz), 7.70 (1H, d, J=9.2 Hz), 7.78 (1H, brs), 7.93 (1H, d, J=2.2 Hz). IR (KBr): 3196, 1519, 1501, 1348, 1038, 812 cm⁻¹.

(ii) Production of 7-Bromo-1,2-dihydronaphtho[2,1-b]furan

In a similar manner to that described in Example 14-(iv), the reaction was carried out by using 6-bromo-1-(2-hydroxyethyl)-2-naphthol (0.660 g) to give the titled compound (0.43 g) as a colorless solid.

¹H-NMR (CDCl₃) δ: 3.45 (2H, t, J=9.0 Hz), 4.75 (2H, t, J=9.0 Hz), 7.11 (1H, d, J=8.8 Hz), 7.43 (1H, d, J=8.8 Hz), 7.47–7.60 (2H, m), 7.93 (1H, d, J=1.9 Hz). IR (KBr): 2922, 1510, 1348, 1244, 970, 878 cm⁻¹.

(iii) Production of (1,2-Dihydronaphtho[2,1-b]furan-7-yl)(1-trityl-1H-imidazol-4-yl)methanol In a similar manner to that described in Example 14-(v), the reaction was carried out by using 7-bromo-1,2-dihydronaphtho[2,1-b]furan (7.70 g) to give the titled compound (7.48 g) as a colorless solid.

¹H-NMR (CDCl₃) δ: 3.45 (2H, t, J=9.0 Hz), 4.47 (2H, t, J=9.0 Hz), 5.89 (1H, s), 6.33 (1H, m), 7.05–7.17 (7H, m), 7.26–7.36 (9H, m), 7.42 (1H, d, J=1.6 Hz), 7.48–7.57 (2H, m), 7.61 (1H, d, J=8.8 Hz), 7.82 (1H, s). IR (KBr): 3059, 1481, 1445, 1244, 733, 702 cm⁻¹.

(iv) Production of (1,2-Dihydronaphtho[2,1-b]furan-7-yl)(1-trityl-1H-imidazol-4-yl)ketone In a similar manner to that described in Example 11-(iv), the reaction was carried out by using (1,2-dihydronaphtho[2,1-b]furan-7-yl)(1-trityl-1H-imidazol-4-yl)methanol (7.48 g) to give the titled compound (5.82 g) as a colorless solid.

¹H-NMR (CDCl₃) δ: 3.51 (2H, t, J=9.0 Hz), 4.80 (2H, t, J=9.0 Hz), 7.10–7.24 (7H, m), 7.32–7.47 (9H, m), 7.58 (1H, d, J=1.5 Hz), 7.62 (1H, d, J=8.8 Hz), 7.76 (1H, d, J=1.5 Hz), 7.80 (1H, d, J=8.8 Hz), 8.27 (1H, dd, J=1.8, 8.8 Hz), 9.00 (1H, d, J=1.8 Hz). IR (KBr): 3395, 1620, 1522, 1175, 747, 702 cm⁻¹.

(v) Production of (1,2-Dihydronaphtho[2,1-b]furan-7-yl)(1H-imidazol-4-yl)ketone

In a similar manner to that described in Example 11-(v), the reaction was carried out by using (1,2-dihydronaphtho[2,1-b]furan-7-yl)(1-trityl-1H-imidazol-4-yl)ketone (5.50 g) to give the titled compound (2.56 g) as a colorless powder.

¹H-NMR (DMSO-d₆) δ: 3.51 (2H, t, J=9.1 Hz), 4.78 (2H, t, J=9.1 Hz), 7.23 (1H, d, J=8.8 Hz), 7.74 (1H, d, J=8.8 Hz), 7.88–8.03 (3H, m), 8.12 (1H, dd, J=1.6, 8.8 Hz), 8.86 (1H, s). IR (KBr): 2969, 1620, 1468, 1356, 1246, 1154, 858 cm⁻¹.

(vi) Production of 1-(1,2-Dihydronaphtho[2,1-b]furan-7-yl)-1-(1H-imidazol-4-yl)-1-ethanol In a similar manner to that described in Example 15, the reaction was carried out by using (1,2-dihydronaphtho[2,1-b]furan-7-yl)(1H-imidazol-4-yl)ketone (0.501 g) to give the titled compound (0.491 g) as a colorless solid.

¹H-NMR (DMSO-d₆) δ: 1.83 (3H, s), 3.41 (2H, t, J=8.9 Hz), 4.69 (2H, t, J=8.9 Hz), 6.83 (1H, br s), 7.08 (1H, d, J=8.6 Hz), 7.40–7.80 (4H, m), 7.91 (1H, s). IR (KBr): 3164, 1248, 970, 802 cm⁻¹.

Example 18

Production of 1-(1,2-Dihydronaphtho[2,1-b]furan-7-yl)-1-(1H-imidazol-4-yl)-1-propanol In a similar manner to that described in Example 16, the reaction was carried out by using (1,2-dihydronaphtho[2,1-b]furan-7-yl)(1H-imidazol-4-yl)ketone (0.523 g) to give the titled compound (0.512 g) as a colorless solid.

¹H-NMR (CDCl₃) δ: 0.86 (3H, t, J=7.3 Hz), 2.12–2.40 (2H, m), 3.43 (2H, t, J=9.0 Hz), 4.73 (2H, t, J=9.0 Hz), 6.84 (1H, d, J=1.0 Hz), 7.08 (1H, d, J=8.8 Hz), 7.38 (1H, d, J=1.0 Hz), 7.44 (1H, dd, J=1.8, 8.6 Hz), 7.51 (1H, d, J=8.6 Hz), 7.62 (1H, d, J=8.8 Hz), 7.90 (1H, d, J=1.2 Hz). IR (KBr): 3121, 2973, 1480, 1244, 970, 820, 733 cm⁻¹.

Example 19

Production of 1-(1,2-Dihydronaphtho[2,1-b]furan-7-yl)-1-(1H-imidazol-4-yl)-2-methyl-1-propanol (i) Production of Ethyl 2,3-Dihydronaphtho[2,3-b]furan-6-carboxylate 5-Bromo-2,3-dihydrobenzofuran (38.86 g), which was prepared according to the literature (Alabaster, Ramon J. et al., Synthesis, 1988, vol. 12, pp950.), was dissolved in THF (300 mL) and cooled to −78° C. n-Butyl-lithium in hexane (1.6M; 160 mL) was added to the solution and stirred for 30 min. DMF (40 mL) was added to the mixture and was allowed to warm to room temperature. Water was added to the mixture and the solvent was evaporated. The residue was diluted with ethyl acetate, washed with water and brine, dried and concentrated to give crude product of 5-formyl-2,3-dihydrobenzofuran (28.47 g) as an oil. The similar reaction described in Example 13-(i) was carried out by using the crude product (25.85 g) to give the titled compound (10.15 g) as a colorless solid.

¹H-NMR (CDCl₃) δ: 1.43 (3H, t, J=7.2 Hz), 3.38 (2H, dt, J=1.0, 8.5 Hz), 4.42 (2H, q, J=7.2 Hz), 4.68 (2H, t, J=8.5 Hz), 7.11 (1H, s), 7.68 (1H, d, J=9.2 Hz), 7.72 (1H, s), 7.96 (1H, dd, J=1.4, 9.2 Hz), 8.46 (1H, m). IR (KBr): 2982, 1703, 1466, 1285, 1204, 1096, 868 cm⁻¹.

(ii) Production of (2,3-Dihydronaphtho[2,3-b]furan-6-yl)methanol

In a similar manner to that described in Example 13-(ii), the reaction was carried out by using ethyl 2,3-dihydronaphtho[2,3-b]furan-6-carboxylate (9.35 g) to give the titled compound (6.88 g) as a colorless solid.

¹H-NMR (CDCl₃) δ: 3.35 (2H, dt, J=1.4, 8.3 Hz), 4.63 (2H, t, J=8.3 Hz), 4.75 (2H, s), 7.07 (1H, s), 7.37 (1H, dd, J=1.6, 8.6 Hz), 7.57–7.70 (3H, m). IR (KBr): 3322, 2901, 1478, 1240, 1034, 988, 866 cm⁻¹.

(iii) Production of 6-Formyl-2,3-dihydronaphtho[2,3-b]furan

In a similar manner to that described in Example 13-(iii), the reaction was carried out by using (2,3-dihydronaphtho[2,3-b]furan-6-yl)methanol (5.96 g) to give the titled compound (4.22 g) as a colorless solid.

¹H-NMR (CDCl₃) δ: 3.41 (2H, t, J=8.7 Hz), 4.71 (2H, t, J=8.7 Hz), 7.14 (1H, s), 7.60–7.90 (3H, m), 8.20 (1H, s), 10.07 (1H, s). IR (KBr): 1698, 1464, 1175, 988, 868 cm⁻¹.

(iv) Production of (2,3-Dihydronaphtho[2,3-b]furan-6-yl)(1H-imidazol-4-yl)methanol A solution of 4-bromo-1H-imidazole (2.11 g) in THF (40 ml) was cooled to −78° C. A solution of tert-butyllithium in pentane (1.7 M; 13 ml) was added to the solution. The mixture was stirred at 5° C. for 2 h and then cooled to −78° C. 6-formyl-2,3-dihydronaphtho[2,3-b]furane (1.46 g) in THF (30 ml) was added to the mixture. The mixture was allowed to room temperature and was stirred for 20 h. Ammonium chloride solution was added to the mixture and extracted with mixed solution of THF and ethyl acetate. The organic layer was dried and concentrated. The residue was purified by silica gel chromatography to give the titled compound (1.01 g) as a colorless solid.

¹H-NMR (DMSO-d₆) δ: 3.33 (2H, t, J=8.2 Hz), 4.59 (2H, t, J=8.2 Hz), 5.79 (1H, s), 6.79 (1H, s), 7.07 (1H, s), 7.40 (1H, d, J=8.8 Hz), 7.57 (1H, s), 7.65 (1H, d, J=8.8 Hz), 7.70 (1H, s), 7.76 (1H, s). IR (KBr): 3069, 1460, 1229, 1028, 886, 839 cm⁻¹.

(v) Production of (2,3-Dihydronaphtho[2,3-b]furan-6-yl)(1H-imidazol-4-yl)ketone

In a similar manner to that described in Example 11-(iv), the reaction was carried out by using (2,3-dihydronaphtho[2,3-b]furan-6-yl)(1H-imidazol-4-yl)methanol (0.850 g) to give the titled compound (0.754 g) as a colorless solid.

¹H-NMR (DMSO-d₆) δ: 3.85 (2H, t, J=8.1 Hz), 4.67 (2H, t, J=8.1 Hz), 7.21 (1H, s), 7.80 (1H, d, J=8.7 Hz), 7.91 (1H, s), 7.94 (2H, s), 8.00 (1H, d, J=8.7 Hz), 8.71 (1H, s). IR (KBr): 2892, 1632, 1458, 1171, 1148, 880 cm⁻¹.

(vi) Production of 1-(2,3-Dihydronaphtho[2,3-b]furan-6-yl)-1-(1H-imidazol-4-yl)-2-methyl-1-propanol In a similar manner to that described in Example 11-(vi), the reaction was carried out by using (2,3-dihydronaphtho[2,3-b]furan-6-yl)(1H-imidazol-4-yl)ketone (0.620 g) to give the titled compound (0.366 g) as a colorless solid.

¹H-NMR (CDCl₃) δ: 0.80 (3H, d, J=6.7 Hz), 0.99 (3H, d, J=6.7 Hz), 2.56–2.77 (1H, m), 3.34 (2H, t, J=8.1 Hz), 4.62

(2H, t, J=8.1 Hz), 6.98 (1H, s), 7.04 (1H, s), 7.44 (1H, d, J=8.8 Hz), 7.50 (1H, s), 7.55–7.66 (2H, m), 7.85 (1H, s). IR (KBr): 2973, 1460, 1219, 990, 853 cm$^{-1}$.

Example 20

Production of (S)-(-)-1-(6,7-Dimethoxy-2-naphthyl)-1-(1H-imidazol-4-yl)-2-methyl-1-propanol (i) Production of 1-(Benzyloxymethyl-1H-imidazol-4-yl)-1-(6,7-dimethoxy-2-naphthyl)-2-methyl-1-propanol 1-benzyloxymethyl-4-iodoimidazole (31.5 g) was dissolved in dichloromethane (500 mL) under argon atmosphere. A solution of ethylmagnesium bromide in THF (0.96M; 110 mL) was added dropwise to the solution with keeping the reaction temperature below 8° C. and the mixture was stirred for 1 h. A solution of 6,7-dimethoxy-2-isobutyrylnaphthalene (31 g) in dichloromethane (50 mL) was added to the mixture and stirred at room temperature for 24 h. Saturated ammonium chloride solution (150 mL) and water (350 mL) were added to the mixture, and organic layer was concentrated. The residue was dissolved in THF (200 mL)-ethyl acetate (1 L), washed with water and brine, dried over Na$_2$SO$_4$ and concentrated in vacuo to one tenth of initial volume. The crystals were collected and washed with ethyl acetate to give the titled compound (23.4 g) as colorless crystals. Second crystals (4.53 g) were recovered from the mother liquor.

mp 156–157° C. (AcOEt-hexane); $^1$H-NMR (CDCl$_3$) δ: 0.82 (3H, d, J=6.8 Hz), 0.99 (3H, d, J=6.8 Hz), 2.71 (1H, quintet, J=6.8 Hz), 3.50 (1H, s), 3.97 (6H, s), 4.41 (2H, s), 5.26 (2H, s), 7.01 (1H, d, J=1.2 Hz), 7.08 (1H, s), 7.14 (1H, s), 7.20–7.37 (5H, m), 7.49 (1H, d, J=1.2 Hz), 7.53 (1H, dd, J=1.8 Hz, 8.4 Hz), 7.64 (1H, d, J=8.4 Hz), 7.97 (1H, d, J=1.8 Hz). IR (KBr): 3455, 3061, 2967, 2938, 2907, 2874, 2830, 1630, 1607, 1580, 1510, 1487, 1464, 1437, 1418, 1383, 1252, 1204, 1163, 1134, 1096, 1038, 1005 cm$^{-1}$. Elemental analysis: calcd for C$_{21}$H$_{30}$N$_2$O$_4$: C, 72.62; H, 6.77; N, 6.27. Found: C, 72.52; H, 6.75; N, 6.21.

(ii) Production of 1-(6,7-Dimethoxy-2-naphthyl)-1-(1H-imidazol-4-yl)-2-methyl-1-propanol 1-(1-benzyloxymethyl-1H-imidazol-4-yl)-1-(6,7-dimethoxy-2-naphthyl)-2-methyl-1-propanol (20 g) was dissolved in warm methanol (1 L). Acetic acid (10.24 mL) and 10% Pd—C (50% wet; 20 g) were added and the mixture was stirred vigorously at 40° C. for 9 h under hydrogen atmosphere at 4 atmospheric pressure. The catalyst was filtered off and the filtrate was concentrated in vacuo. The residue was dissolved in ethyl acetate (600 mL), washed with sodium bicarbonate solution and 1M sodium bisulfite solution. The water layer was extracted with ethyl acetate. The organic layers were combined and dried over Na$_2$SO$_4$, concentrated in vacuo. The residue was crystallized from ethyl acetate-diisopropyl ether to give the titled compound (11.15 g) as colorless crystals.

$^1$H-NMR (CDCl$_3$+CD$_3$OD) δ: 0.81 (3H, d, J=6.8 Hz), 1.00 (3H, d, J=6.8 Hz), 2.68 (1H, quintet, J=6.8 Hz), 3.97 (6H, s), 6.98 (1H, d, J=1.0 Hz), 7.08 (1H, s), 7.12 (1H, s), 7.43 (1H, dd, J=1.8 Hz, 8.4 Hz), 7.48 (1H, d, J=1.0 Hz), 7.61(1H, d, J=8.4 Hz), 7.84 (1H, d, J=1.8 Hz).

(iii) Production of (S)-(-)-1-(6,7-Dimethoxy-2-naphthyl)-1-(1H-imidazol-4-yl)-2-methyl-1-propanol 1-(6,7-dimethoxy-2-naphthyl)-1-(1H-imidazol-4-yl)-2-methyl-1-propanol was chromatographed using chiral column (Chiralpak AD), eluting with hexane-ethanol (8:2) to give (S)-(-)-1-(6,7-dimethoxy-2-naphthyl)-1-(1H-imidazol-4-yl)-2-methyl-1-propanol as the first eluting enantiomer.

Optical purity>99%ee (Chiralcel OJ-R, manufactured by Daicel Chemical Industries, LTD). $[α]_D^{27}$-51.3° (C=1.0, methanol).

Example 21

Production of (S)-(-)-1-(6,7-Dimethoxy-2-naphthyl)-1-(1H-imidazol-4-yl)-2-methyl-1-propanol (i) Production of (S)-(-)-1-(6,7-Dimethoxy-2-naphthyl)-1-(1H-imidazol-4-yl)-2-methyl-1-propanol.(-)-5,5-dimethyl-2-hydroxy-4-phenyl-1,3,2-dioxaphosphorinane 2-Oxide Salt 1-(6,7-dimethoxy-2-naphthyl)-1-(1H-imidazol-4-yl)-2-methyl-1-propanol(485 mg) and (-)-5,5-dimethyl-2-hydroxy-4-phenyl-1,3,2-dioxaphosphorinane 2-oxide (653 mg) were dissolved in methanol (4 mL). Diisopropyl ether (3 mL) was added and the resulting clear solution was left at room temperature for 5 h to give needles. The needles were washed with a mixed solution of methanol-diisopropyl ether (1:3, 4 mL) and diisopropyl ether (1 mL) and then dried to give the titled compound (362 mg) as colorless needles. Optical purity; >99% ee (Chiralcel OJ-R, manufactured by Daicel Chemical Industries, Ltd.).

(ii) Production of (S)-(-)-1-(6,7-Dimethoxy-2-naphthyl)-1-(1H-imidazol-4-yl)-2-methyl-1-propanol The diastereomer salt (1.285 g) obtained in Example 21-(i) was suspended in water (12.8 mL). A mixed solution of ethyl acetate-THF (1:1, 48 mL) and 1N NaOH solution (6.4 mL) were added to the suspension and the whole was stirred vigorously. The organic layer was separated, washed with brine, dried over Na$_2$SO$_4$ and concentrated in vacuo to give the titled compound (1.05 g) as a colorless powder. Optical purity; >99%ee (Chiralcel OJ-R, manufactured by Daicel Chemical Industries, Ltd); $[α]_D^{27}$-49.6° (C=1.0, methanol)

Example 22

Production of (S)-(-)-1-(6,7-Dimethoxy-2-naphthyl)-1-(1H-imidazol-4-yl)-2-methyl-1-propanol.fumaric Acid Salt (S)-(-)-1-(6,7-dimethoxy-2-naphthyl)-1-(1H-imidazol-4-yl)-2-methyl-1-propanol (12.6 g) and fumaric acid (4.48 g) were dissolved in methanol (50 mL). The solution was concentrated with heating, and obtained oil was diluted with ethyl acetate (80 mL). After cooling, crystals were filtered and left under humid vapor stream, for 8 h. Drying the crystals gave the titled compound (15.33 g) as colorless crystalline powder.

mp. 117–120° C. $^1$H-NMR (CDCl$_3$+CD$_3$OD) δ: 0.82 (1H, d, J=6.8 Hz), 1.01 (1H, d, J=6.8 Hz), 2.69 (1H, q, J=6.8 Hz), 3.99 (6H, s), 6.81 (2H, s), 7.07 (1H, d, J=1.2 Hz), 7.10 (1H, s), 7.14 (1H, s), 7.41 (1H, dd, J=1.8 Hz, 8.4 Hz), 7.63 (1H, d, J=8.4 Hz), 7.78 (1H, d, J=1.2 Hz), 7.82 (1H, s). $[α]_D^{20}$-34.4° (C=1.0, methanol); Elemental analysis; Calcd for C$_{23}$H$_{26}$N$_2$O$_7$.0.5H$_2$O: C, 61.19; H, 6.03; N, 6.20. Found: C, 61.05; H, 6.00; N, 6.37. Powder X-ray (FIG. 1).

Example 23

Production of (-)-N-{6-[1-Hydroxy-1-(1H-imidazol-4-yl)-2-methylpropyl]naphthalen-2-yl}acetamide (i) Production of 1-(6-Bromonaphthalen-2-yl)-2-methyl-1-(1-trityl-1H-imidazol-4-yl)-1-propanol 2,6-dibromonaphthalene (25.0 g) was dissolved in THF (1250 mL) and cooled to −50° C. n-Butyl-lithium in hexane (1.6 M; 57 mL) was added to the solution and stirred at −50° C. for 20 min. A solution of α-methyl-1-(1-trityl-1H-imidazol-4-yl)-1-propanone (22.2 g) in THF (200 ml) was added to the mixture and stirred at −50° C. for 20 min. Water was added and the organic layer was separated. The water layer was extracted with ethyl acetate. The organic layers were combined, dried and concentrated. The residue was chromatographed on silica gel (eluent; hexane:THF=1:1) followed by crystallization from hexane-ethyl acetate to give pale brown titled compound (31.2 g).

$^1$H-NMR (CDCl$_3$+CD$_3$OD) δ: 0.72 (3H, d, J=6.7 Hz), 0.95 (3H, d, J=6.7 Hz), 2.45–2.58 (1H, m), 3.75 (1H, s), 6.80 (1H, d, J=1.4 Hz), 7.10–7.15 (6H, m), 7.29–7.35 (10H, m), 7.50 (1H, dd, J=1.8, 8.8 Hz), 7.57 (1H, dd, J=1.8, 8.8 Hz), 7.63–7.69 (2H, m), 7.94 (1H, d, J=1.8 Hz), 8.02 (1H, s). IR (KBr): 3241, 2967, 1493, 1445, 1169, 1017, 826, 812, 756, 747, 700 cm$^{-1}$.

(ii) Production of 1-{6-[(Diphenylmethylene)amino]naphthalen-2-yl}-2-methyl-1-(1-trityl-1H-imidazol-4-yl)-1-propanol A mixture of 1-(6-bromo-naphthalen-2-yl)-2-methyl-1-(1-trityl-1H-imidazol-4-yl)-1-propanol (14.0 g), benzophenone imine (5.18 g), tris(dibenzylideneacetone)dipalladium (440 mg), (R)-(+)-2,2'-bis(diphenylphosphino)-1,1'-binaphthyl (872 mg) and sodium t-butoxide (5.72 g) in toluene (140 ml) was heated at 80° C. for 18 h under argon atmosphere. After cooling, the mixture was diluted with ethyl acetate, filtered with celite pad. The filtrate was concentrated and the residue was chromatographed on silica gel (eluent; hexane:THF=1:1) followed by crystallization from hexane-THF (4:1) to give yellow titled compound (14.3 g).

$^1$H-NMR (CDCl$_3$) δ: 0.74 (3H, d, J=6.7 Hz), 0.93 (3H, d, J=6.7 Hz), 2.42–2.56 (1H, d), 3.65 (1H, br s), 6.79 (1H, d, J=1.4 Hz), 6.87 (1H, dd, J=2.0, 8.6 Hz), 7.10–7.57 (28H, m), 7.76 (1H, d, J=2.0 Hz), 7.80 (1H, d, J=1.4 Hz), 7.86 (1H, s). IR (KBr): 3453, 2969, 1493, 1445, 1256, 1163, 1005, 812, 748 cm$^{-1}$.

(iii) Production of N-{6-[1-Hydroxy-2-methyl-1-(1-trityl-1H-imidazol-4-yl)propyl]naphthalen-2-yl}acetamide To a solution of 1-{6-[(diphenylmethylene)amino]naphthalene-2-yl}-2-methyl-1-(1-trityl-1H-imidazol-4-yl)-1-propanol (15.0 g) in THF (100 mL)-methanol (100 mL) were added sodium acetate (4.29 g) and hydroxylamine hydrochloride (2.73 g), and the mixture was stirred at room temperature for 20 min. After addition of 0.1N-NaOH solution, the mixture was extracted with ethyl acetate. The extract was washed with brine, dried and concentrated. The residue was dissolved in dichloromethane and pyridine (5.3 mL) and acetic anhydride (4.1 mL) were added. The mixture was stirred at room temperature for 40 min and then saturated sodium bicarbonate solution was added and was extracted with dichloromethane. The extract was dried and concentrated and the residue was crystallized from ethyl acetate to give the titled compound (11.6 g) as pale red crystals.

$^1$H-NMR (CDCl$_3$+CD$_3$OD) δ: 0.75 (3H, d, J=6.7 Hz), 0.95 (3H, d, J=6.7 Hz), 2.20 (3H, s), 2.57–2.71 (1H, m), 6.87 (1H, d, J=1.4 Hz), 7.10–7.15 (6H, m), 7.32–7.54 (12H, m), 7.68–7.77 (2H, m), 7.92 (1H, s), 8.15 (1H, s), 9.60 (1H, br s). IR (KBr): 3058, 2969, 1686, 1611, 1547, 1493, 1445, 1298, 1011, 766, 747, 700 cm$^{-1}$.

(iv) Production of N-{6-[1-Hydroxy-1-(1H-imidazol-4-yl)-2-methylpropyl]naphthalen-2-yl}acetamide In a similar manner to that described in Reference example 5, the reaction was carried out by using N-{6-[1-hydroxy-2-methyl-1-(1-trityl-1H-imidazol-4-yl)propyl]naphthalene-2-yl}acetamide (11.5 g) to give the titled compound (5.52 g) as a pale red powder.

$^1$H-NMR (CDCl$_3$+CD$_3$OD) δ: 0.79 (3H, d, J=6.8 Hz), 1.0 (3H, d, J=6.8 Hz), 2.17 (3H, s), 2.63–2.76 (1H, m), 6.99 (1H, s), 7.43–7.54 (3H, m), 7.65–7.74 (2H, m), 7.91 (1H, s), 8.11 (1H, s). IR (KBr): 3248, 2971, 1669, 1609, 1586, 1557, 1495, 1391, 1296, 818 cm$^{-1}$.

(v) Production of (–)-N-{6-[1-Hydroxy-1-(1H-imidazol-4-yl)-2-methylpropyl]naphthalen-2-yl}acetamide N-{6-[1-hydroxy-1-(1H-imidazol-4-yl)-2-methylpropyl]naphthalen-2-yl}acetamide was chromatographed using chiral column (Chiralpak AD), eluting with hexane-ethanol (85:15). (–)-N-{6-[1-hydroxy-1-(1H-imidazol-4-yl)-2-methylpropyl]naphthalen-2-yl}acetamide was obtained as first fraction.

Optical purity; >99%ee (Chiralpak AD, manufactured by Daicel Chemical Industries, Ltd.).

(vi) Production of (–)-N-{6-[1-Hydroxy-1-(1H-imidazol-4-yl)-2-methylpropyl]naphthalen-2-yl}acetamide Fumaric Acid Salt (–)-N-{6-[1-hydroxy-1-(1H-imidazol-4-yl)-2-methylpropyl]naphthalen-2-yl}acetamide (50 mg) and fumaric acid (17 mg) were crystallized from methanol-ethyl acetate to give the titled compound (59 mg) as colorless crystalline powder.

$[\alpha]_D^{20}$ –28.5° (C=1.0, methanol).

Example 24

Production of N-Ethyl-6-[1-hydroxy-1-(1H-imidazol-4-yl)-2-methylpropyl)-2-naphthamide (i) Production of N-Ethyl-6-[1-hydroxy-2-methyl-1-(1-trityl-1H-imidazol-4-yl)propyl)-2-naphthamide To a solution of methyl 6-(1-hydroxy-2-methyl-1-(1-trityl-1H-imidazol-4-yl)propyl)-2-naphthoate (14.0 g) in THF (140 mL) was added methanol (30 mL) and 4N-NaOH (30 mL) at 60° C. The mixture was stirred for 2 h, neutralized with conc.HCl. The mixture was concentrated, diluted with water and extracted with ethyl acetate. The extract was concentrated to give crude mixture of 6-(1-hydroxy-2-methyl-1-(1-trityl-1H-imidazol-4-yl)propyl)-2-naphthoic acid. To a solution of the crude mixture was added ethylamine hydrochloride (2.41 g), 1-hydroxybenzotriazole (4.53 g) and 1-(3-dimethylaminopropyl)-3-ethylcarbodiimide hydrochloride (5.67 g) under ice cooling. The mixture was stirred at room temperature for 20 h, diluted with water and extracted with ethyl acetate. The extract was concentrated and purified by column chromatography (eluent; hexane:THF=1:2) followed by crystallization from hexane-ethyl acetate to give the titled compound (12.0 g) as a colorless powder.

$^1$H-NMR (CDCl$_3$) δ: 0.73 (3H, d, J=3.3 Hz), 0.96 (3H, d, J=6.6 Hz), 1.28 (3H, t, J=7.2 Hz), 2.47–2.60 (1H, m), 3.48–3.61 (2H, m), 3.79 (1H, s), 6.32 (1H, t, J=5.5 Hz), 6.82 (1H, d, J=1.4 Hz), 7.09–7.16 (6H, m), 7.28–7.34 (10H, m), 7.61 (1H, dd, J=1.8, 8.8 Hz), 7.75–7.84 (3H, m), 8.05 (1H, s), 8.23 (1H, s). IR (KBr): 3308, 2967, 1638, 1535, 1308, 1009, 747, 700 cm$^{-1}$.

(ii) Production of N-Ethyl-6-[1-hydroxy-1-(1H-imidazol-4-yl)-2-methylpropyl)-2-naphthamide A mixture of N-ethyl-6-[1-hydroxy-2-methyl-1-(1-trityl-1H-imidazol-4-yl)propyl)-2-naphthamide (11.5 g) and pyridinium chloride (4.62 g) in methanol (60 mL) was stirred at 60° C. for 2 h. The mixture was neutralized with sodium bicarbonate solution and concentrated. The residue was dissolved in ethanol and insoluble material was filtered off. The filtrate was concentrated and purified by column chromatography (eluent; dichloromethane:methanol=10:1→7:1) to give the titled compound (5.75 g) as a colorless powder.

$^1$H-NMR (CDCl$_3$+CD$_3$OD) δ: 0.77 (3H, d, J=7.0 Hz), 1.00 (3H, d, J=7.0 Hz), 1.26 (3H, t, J=7.2 Hz), 2.63–2.77 (1H, m), 3.42–3.56 (2H, m), 6.98 (1H, d, J=1.2 Hz), 7.22 (1H, t, J=5.5 Hz), 7.44 (1H, d, J=1.2 Hz), 7.59 (1H, dd,

J=1.6, 8.6 Hz), 7.70–7.76 (3H, m), 8.01 (1H, s), 8.19 (1H, s). IR (KBr): 3310, 2971, 1638, 1561, 1306, 1146, 816 cm$^{-1}$.

Example 25

Production of 6-[1-(Hydroxy-1-(1H-imidazol-4-yl)-2-methylpropyl)-N-propyl-2-naphthamide (i) Production of 6-[1-(Hydroxy-2-methyl-1-(1-trityl-1H-imidazol-4-yl)propyl)-N-propyl-2-naphthamide In a manner to that described in Example 9-(i), methyl 6-(1-hydroxy-2-methyl-1-(1-trityl-1H-imidazol-4-yl)propyl)-2-naphthoate (2.83 g) was converted to 6-(1-hydroxy-2-methyl-1-(1-trityl-1H-imidazol-4-yl)propyl)-2-naphthoic acid, which was reacted with n-propylamine (0.66 mL) in a similar manner as described in Example 24-(i) to give the titled compound (2.74 g) as a colorless powder.

$^1$H-NMR (CDCl$_3$) δ: 0.73 (3H, d, J=6.8 Hz), 0.96 (3H, d, J=6.8 Hz), 1.02 (3H, t, J=7.2 Hz), 1.60–1.78 (2H, m), 2.53 (1H, quintet, J=6.8 Hz), 3.48 (2H, q, J=7.2 Hz), 3.76 (1H, s), 6.28 (1H, t, J=Hz), 6.81 (1H, d, J=1.4 Hz), 7.07–7.20 (6H, m), 7.28–7.37 (10H, m), 7.62 (1H, dd, J=1.8, 8.6 Hz), 7.75–7.86 (3H, m), 8.06 (1H, s), 8.23 (1H, s). IR (KBr): 3326, 2967, 1642, 1599, 1541, 1445, 1308, 1157 cm$^{-1}$.

(ii) Production of 6-[1-(Hydroxy-1-(1H-imidazol-4-yl)-2-methylpropyl)-N-propyl-2-naphthamide In a similar manner to that described in Reference example 5, the reaction was carried out by using 6-[1-(hydroxy-2-methyl-1-(1-trityl-1H-imidazol-4-yl)propyl)-N-propyl2-naphthamide (2.48 g) to give the titled compound (1.13 g) as a colorless powder.

$^1$H-NMR (CDCl$_3$) δ: 0.78 (3H, d, J=6.6 Hz), 1.00 (3H, t, J=7.2 Hz), 1.00 (3H, d, J=6.6 Hz), 1.58–1.77 (2H, m), 2.68 (1H, quintet, J=7.2 Hz), 3.40–3.52 (2H, m), 3.49 (1H, s), 6.44 (1H, t, J=5.5 Hz), 6.99 (1H, s), 7.45 (1H, s), 7.59–7.80 (4H, m), 8.05 (1H, s), 8.17 (1H, s). IR (KBr): 3400–3100, 2967, 1640, 1601, 1539, 1464, 1308, 1144 cm$^{-1}$.

Example 26

Production of 6-[1-Hydroxy-1-(1H-imidazol-4-yl)-2-methylpropyl)-N-isopropyl-2-naphthamide (i) Production of 6-[1-(Hydroxy-2-methyl-1-(1-trityl-1H-imidazol-4-yl)propyl)-N-isopropyl-2-naphthamide To a solution of methyl 6-(1-hydroxy-2-methyl-1-(1-trityl-1H-imidazol-4-yl)propyl)-2-naphthoate (16.4 g) in THF (160 mL) was added methanol (35 mL) and 4N-NaOH (35 mL) at 60° C. The mixture was stirred for 2 h, neutralized with conc.HCl. The mixture was concentrated, diluted with water and extracted with ethyl acetate. The extract was concentrated to give crude mixture of 6-(1-hydroxy-2-methyl-1-(1-trityl-1H-imidazol-4-yl)propyl)-2-naphthoic acid. To a solution of the crude mixture was added isopropylamine (3.95 mL), 1-hydroxybenzotriazole (5.33 g), 1-(3-dimethylaminopropyl)-3-ethylcarbodiimide hydrochloride (6.67 g) and diisopropylethylamine (6.0 mL) under ice cooling. The mixture was stirred at room temperature for 14 h, diluted with water and extracted with ethyl acetate. The extract was washed with brine, concentrated. The residue was crystallized from ethyl acetate to give the titled compound (16.7 g) as a colorless powder.

$^1$H-NMR (CDCl$_3$) δ: 0.73 (3H, d, J=6.8 Hz), 0.96 (3H, d, J=6.8 Hz), 1.31 (6H, d, J=6.6 Hz), 2.53 (1H, quintet, J=6.8 Hz), 3.76 (1H, s), 4.27–4.43 (1H, m), 6.06 (1H, d, J=7.4 Hz), 6.81 (1H, d, J=1.4 Hz), 7.07–7.18 (6H, m), 7.28–7.38 (10H, m), 7.61 (1H, dd, J=1.8, 8.6 Hz), 7.74–7.85 (3H, m), 8.06 (1H, s), 8.22 (1H, s). IR (KBr): 3301, 2971, 1640, 1601, 1537, 1447, 1289, 1235, 1171 cm$^{-1}$.

(ii) Production of 6-[1-Hydroxy-1-(1H-imidazol-4-yl)-2-methylpropyl)-N-isopropyl-2-naphthamide A mixture of 6-[1-hydroxy-2-methyl-1-(1-trityl-1H-imidazol-4-yl)propyl)-N-isopropyl-2-naphthamide (16.6 g) and pyridinium chloride (6.46 g) in methanol (84 mL) was heated at 60° C. for 3 h. The solvent was evaporated and the residue was dissolved in chloroform, which was washed with saturated sodium bicarbonate solution, dried and concentrated. The residue was purified by column chromatography (eluent; CHCl$_3$: 8% methanolic ammonia=19:1→9:1) to give the titled compound (8.3 g) as a colorless powder.

$^1$H-NMR (CDCl$_3$) δ: 0.77 (3H, d, J=6.8 Hz), 1.00 (3H, d, J=6.8 Hz), 1.29 (6H, d, J=6.6 Hz), 2.67 (1H, quintet, J=6.8 Hz), 3.48 (1H, s), 4.26–4.42 (1H, m), 6.23 (1H, d, J=7.8 Hz), 6.97 (1H, d, J=1.2 Hz), 7.41 (1H, d, J=1.2 Hz), 7.57–7.80 (4H, m), 8.04 (1H, s), 8.14 (1H, s). IR (KBr): 3400–3100, 2973, 1626, 1601, 1537, 1456, 1294, 1246, 1173 cm$^{-1}$.

Example 27

Production of N-Butyl-6-[1-(hydroxy-1-(1H-imidazol-4-yl)-2-methylpropyl)-2-naphthamide (i) Production of N-Butyl-6-[1-hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)propyl)-2-naphthoate (2.83 g) was converted to 6-(1-hydroxy-2-methyl-1-(1-trityl-1H-imidazol-4-yl)propyl)-2-naphthoic acid, which was reacted with n-butylamine (0.80 mL) in a similar manner as described in Example 24-(i) to give the titled compound (2.81 g) as a colorless powder.

$^1$H-NMR(CDCl$_3$) δ: 0.73 (3H, d, J=6.6 Hz), 0.96 (3H, d, J=6.6 Hz), 0.98 (3H, t, J=7.2 Hz), 1.37–1.73 (4H, m), 2.53 (1H, quintet, J=6.6 Hz), 3.47–3.56 (2H, m), 3.76 (1H, s), 6.25 (1H, t, J=5.6 Hz), 6.81 (1H, d, J=1.4 Hz), 7.08–7.18 (6H, m), 7.27–7.39 (10H, m), 7.62 (1H, dd, J=1.6, 8.8 Hz), 7.74–7.86 (3H, m), 8.06 (1H, s), 8.23 (1H, s). IR (KBr): 3316, 2961, 1644, 1599, 1543, 1445, 1306, 1159 cm$^{-1}$.

(ii) Production of N-Butyl-6-[1-hydroxy-1-(1H-imidazol-4-yl)-2-methylpropyl)-2-naphthamide In a similar manner to that described in Reference example 5, the reaction was carried out by using N-butyl-6-[1-hydroxy-2-methyl-1-(1-trityl-1H-imidazol-4-yl)propyl)-2-naphthamide (2.58 g) to give the titled compound (1.24 g) as a colorless powder.

$^1$H-NMR (CDCl$_3$) δ: 0.77 (3H, d, J=6.6 Hz), 0.96 (3H, t, J=7.2 Hz), 1.00 (3H, d, J=6.6 Hz), 1.34–1.52 (2H, m), 1.56–1.72 (2H, m), 2.66 (1H, quintet, J=6. Hz), 3.48 (1H, s), 3.49 (2H, q, J=7.2 Hz), 6.51 (1H, t, J=5.8 Hz), 6.96 (1H, d, J=1.2 Hz), 7.39 (1H, d, J=1.2 Hz), 7.59 (1H, dd, J=1.6, 8.6 Hz), 7.65–7.76 (3H, m), 8.02 (1H, s), 8.14 (1H, s). IR (KBr): 3400–3100, 2963, 1640, 1601, 1547, 1306, 1144 cm$^{-1}$.

Example 28

Production of N-Cyclopropyl-6-[1-hydroxy-1-(1H-imidazol-4-yl)-2-methylpropyl)-2-naphthamide (i) Production of N-Cyclopropyl-6-[1-hydroxy-2-methyl-1-(1-trityl-1H-imidazol-4-yl)propyl)-2-naphthamide To a solution of methyl 6-(1-hydroxy-2-methyl-1-(1-trityl-1H-imidazol-4-yl)propyl)-2-naphthoate (16.5 g) in THF (160 mL) was added methanol (35 mL) and 4N-NaOH (35 mL) at 60° C. The mixture was stirred for 2 h, neutralized with conc.HCl. The mixture was concentrated, diluted with water and extracted with ethyl acetate. The extract was concentrated to give crude mixture of 6-(1-hydroxy-2-methyl-1-(1-trityl-1H-imidazol-4-yl)propyl)-2-naphthoic acid. To a solution of the crude mixture was added cyclopropylamine (3.24 mL), 1-hydroxybenzotriazole (5.37 g) and 1-(3-dimethylaminopropyl)-3-ethylcarbodiimide hydrochloride (6.72 g) under ice cooling. The mixture was stirred at room temperature for 63 h, diluted with water and extracted with ethyl acetate. The extract was washed with brine, dried and concentrated. The residue was washed with diethyl ether to give the titled compound (17.6 g) as a colorless powder.

$^1$H-NMR (CDCl$_3$) δ: 0.63–0.74 (2H, m), 0.73 (3H, d, J=6.8 Hz), 0.87–0.98 (2H, m), 0.96 (3H, d, J=6.8 Hz), 2.53 (1H, quintet, J=6.8 Hz), 2.90–3.03 (1H, m), 3.74 (1H, s), 6.36 (1H, brs), 6.81 (1H, d, J=1.4 Hz), 7.08–7.19 (6H, m), 7.29–7.38 (10H, m), 7.61 (1H, dd, J=1.6, 8.6 Hz), 7.72–7.85 (3H, m), 8.06 (1H, s), 8.20 (1H, s). IR (KBr): 3285, 2969, 1645, 1599, 1532, 1495, 1304, 1165 cm$^{-1}$.

(ii) Production of N-Cyclopropyl-6-[1-hydroxy-1-(1H-imidazol-4-yl)-2-methylpropyl)-2-naphthamide A mixture of N-cyclopropyl-6-[1-hydroxy-2-methyl-1-(1-trityl-1H-imidazol-4-yl)propyl)-2-naphthamide (16.0 g) and pyridinium chloride (6.46 g) in methanol (84 mL) was heated at 60° C. for 3 h. The mixture was neutralized with sodium bicarbonate solution. The solvent was evaporated and the residue was dissolved in ethanol and insoluble material was filtered off. The filtrate was concentrated and purified by column chromatography (eluent; CHCl$_3$: 8% methanolic ammonia=19:1→9:1) to give the titled compound (8.9 g) as a colorless powder.

$^1$H-NMR (CDCl$_3$+CD$_3$OD) δ: 0.64–0.72 (2H, m), 0.77 (3H, d, J=6.6 Hz), 0.82–0.94 (2H, m), 1.00 (3H, d, J=6.6 Hz), 2.69 (1H, quintet, J=6.6 Hz), 2.86–2.98 (1H, m), 6.94 (1H, brs), 6.98 (1H, d, J=1.2 Hz), 7.45 (1H, d, J=1.2 Hz), 7.60 (1H, dd, J=1.4, 8.6 Hz), 7.68–7.80 (3H, m), 8.02 (1H, s), 8.15 (1H, s). IR (KBr): 3400–3100, 2971, 1622, 1537, 1485, 1435, 1304, 1127 cm$^{-1}$.

Example 29

Production of N-Cyclobutyl-6-[1-hydroxy-1-(1H-imidazol-4-yl)-2-methylpropyl)-2-naphthamide (i) Production of N-Cyclobutyl-6-[1-(hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)propyl)-2-naphthoate (1.78 g) was converted to 6-(1-hydroxy-2-methyl-1-(1-trityl-1H-imidazol-4-yl)propyl)-2-naphthoic acid, which was reacted with cyclobutylamine hydrochloride (405 mg) in a similar manner as described in Example 24-(i) to give the titled compound (1.36 g) as a colorless powder.

$^1$H-NMR (CDCl$_3$) δ: 0.73 (3H, d, J=6.6 Hz), 0.96 (3H, d, J=6.6 Hz), 1.74–1.85 (2H, m), 1.91–2.06 (2H, m), 2.40–2.56 (3H, m), 3.77 (1H, s), 4.59–4.71 (1H, m), 6.41 (1H, d, J=7.6 Hz), 6.81 (1H, d, J=1.2 Hz), 7.09–7.14 (6H, m), 7.29–7.34 (10H, m), 7.61 (1H, dd, J=1.8, 8.8 Hz), 7.78–7.85 (3H, m), 8.05 (1H, s), 8.22 (1H, s). IR (KBr): 3333, 2966, 1628, 1529, 746, 702 cm$^{-1}$.

(ii) Production of N-Cyclobutyl-6-[1-(hydroxy-1-(1H-imidazol-4-yl)-2-methylpropyl)-2-naphthamide In a similar manner to that described in Reference example 5, the reaction was carried out by using N-cyclobutyl-6-[1-(hydroxy-2-methyl-1-(1-trityl-1H-imidazol-4-yl)propyl)-2-naphthamide (1.30 g) to give the titled compound (733 mg) as a colorless powder.

$^1$H-NMR (CDCl$_3$+CD$_3$OD) δ: 0.77 (3H, d, J=7.0 Hz), 1.00 (3H, d, J=6.6 Hz), 1.68–1.84 (2H, m), 1.96–2.14 (2H, m), 2.35–2.49 (2H, m), 2.64–2.77 (1H, m), 4.48–4.68 (1H, m), 6.98 (1H, d, J=1.0 Hz), 7.31 (1H, d, J=7.6 Hz), 7.45 (1H, d, J=1.0 Hz), 7.60 (1H, dd, J=1.4, 8.8 Hz), 7.72–7.81 (3H, m), 8.01 (1H, s), 8.19 (1H, s). IR (KBr): 3300, 2970, 1638, 1533, 1302, 816 cm$^{-1}$.

Example 30

Production of N-Cyclopropylmethyl-6-[1-hydroxy-1-(1H-imidazol-4-yl)-2-methylpropyl)-2-naphthamide (i) Production of N-Cyclopropylmethyl-6-[1-hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)propyl)-2-naphthoate (1.78 g) was converted to 6-(1-hydroxy-2-methyl-1-(1-trityl-1H-imidazol-4-yl)propyl)-2-naphthoic acid, which was reacted with cyclopropylamine hydrochloride (405 mg) in a similar manner as described in Example 24-(i) to give the titled compound (1.59 g) as a colorless powder.

$^1$H-NMR (CDCl$_3$) δ: 0.29–0.34 (2H, m), 0.53–0.62 (2H, m), 0.73 (3H, d, J=6.6 Hz), 0.96 (3H, d, J=7.0 Hz), 1.02–1.18 (1H, m), 2.47–2.60 (1H, m), 3.35 (1H, d, J=5.5 Hz), 3.38 (1H, d, J=5.5 Hz), 3.79 (1H, s), 6.43 (1H, t, J=5.3 Hz), 6.82 (1H, d, J=1.4 Hz), 7.09–7.16 (6H, m), 7.29–7.35 (10H, m), 7.62 (1H, dd, J=1.8, 8.8 Hz), 7.79–7.83 (3H, m), 8.06 (1H, s), 8.25 (1H, s). IR (KBr): 3385, 2966, 1651, 1529, 1296, 745, 700 cm$^{-1}$.

(ii) Production of N-Cyclopropylmethyl-6-[1-hydroxy-1-(1H-imidazol-4-yl)-2-methylpropyl)-2-naphthamide In a similar manner to that described in Reference example 5, the reaction was carried out by using N-cyclopropylmethyl-6-[1-(hydroxy-2-methyl-1-(1-trityl-1H-imidazol-4-yl)propyl)-2-naphthamide (1.40 g) to give the titled compound (798 mg) as a colorless powder.

$^1$H-NMR (CDCl$_3$+CD$_3$OD) δ: 0.26–0.33 (2H, m), 0.52–0.61 (2H, m), 0.78 (3H, d, J=7.0 Hz), 1.00 (3H, d, J=7.0 Hz), 1.07–1.18 (1H, m), 2.65–2.78 (1H, m), 3.29–3.36 (2H, m), 6.99 (1H, d, J=1.0 Hz), 7.15 (1H, t, J=5.5 Hz), 7.47 (1H, d, J=1.0 Hz), 7.62 (1H, dd, J=1.7, 8.7 Hz), 7.74–7.84 (3H, m), 8.02 (1H, s), 8.22 (1H, s). IR (KBr): 3300, 2970, 1639, 1539, 1300, 812 cm$^{-1}$.

Example 31

Production of N-Cyclopentyl-6-[1-hydroxy-1-(1H-imidazol-4-yl)-2-methylpropyl)-2-naphthamide (i) Production of N-Cyclopentyl-6-[1-hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)propyl)-2-naphthoate (2.83 g) was converted to 6-(1-hydroxy-2-methyl-1-(1-trityl-1H-imidazol-4-yl)propyl)-2-naphthoic acid, which was reacted with cyclopentylamine (0.16 ml) in a similar manner as described in Example 24-(i) to give the titled compound (509 mg) as a colorless powder.

$^1$H-NMR (CDCl$_3$) δ: 0.73 (3H, d, J=6.6 Hz), 0.96 (3H, d, J=6.6 Hz), 1.45–1.86 (6H, m), 2.05–2.24 (2H, m), 2.53 (1H, quintet, J=6.6 Hz), 3.75 (1H, s), 4.38–4.56 (1H, m), 6.17 (1H, d, J=7.4 Hz), 6.81 (1H, d, J=1.0 Hz), 7.07–7.18 (6H, m), 7.28–7.38 (10H, m), 7.61 (1H, dd, J=1.8, 8.6 Hz), 7.75–7.86 (3H, m), 8.06 (1H, s), 8.21 (1H, s). IR (KBr) 3362, 2965, 1640, 1601, 1532, 1495, 1445, 1318 cm$^{-1}$.

(ii) Production of N-Cyclopentyl-6-[1-hydroxy-1-(1H-imidazol-4-yl)-2-methylpropyl)-2-naphthamide In a similar manner to that described in Reference example 5, the reaction was carried out by using N-cyclopentyl-6-[1-hydroxy-2-methyl-1-(1-trityl-1H-imidazol-4-yl)propyl)-2-naphthamide (428 mg) to give the titled compound (183 mg) as a colorless powder.

$^1$H-NMR (CDCl$_3$) δ: 0.77 (3H, d, J=6.8 Hz), 1.00 (3H, d, J=6.8 Hz), 1.45–1.87 (6H, m), 2.03–2.23 (2H, m), 2.67 (1H, quintet, J=6.8 Hz), 3.48 (1H, s), 4.37–4.53 (1H, m), 6.34

(1H, d, J=7.6 Hz), 6.97 (1H, s), 7.42 (1H, s), 7.57–7.79 (4H, m), 8.04 (1H, s), 8.14 (1H, s). IR (KBr): 3500–3100, 2969, 1634, 1539, 1495, 1316, 1138 cm$^{-1}$.

Example 32

Production of N-Cyclohexyl-6-[1-hydroxy-1-(1H-imidazol-4-yl)-2-methylpropyl]-2-naphthamide (i) Production of N-Cyclohexyl-6-[1-hydroxy-2-methyl-1-(1-trityl-1H-imidazol-4-yl)propyl]-2-naphthamide In a manner to that described in Example 9-(i), methyl 6-(1-hydroxy-2-methyl-1-(1-trityl-1H-imidazol-4-yl)propyl)-2-naphthoate (2.83 g) was converted to 6-(1-hydroxy-2-methyl-1-(1-trityl-1H-imidazol-4-yl)propyl)-2-naphthoic acid, which was reacted with cyclohexylamine (0.18 mL) in a similar manner as described in Example 24-(i) to give the titled compound (598 mg) as a colorless powder.

$^1$H-NMR (CDCl$_3$) δ: 0.73 (3H, d, J=6.6 Hz), 0.96 (3H, d, J=6.6 Hz), 1.17–1.87 (8H, m), 2.01–2.17 (2H, m), 2.53 (1H, quintet, J=6.6 Hz), 3.76 (1H, s), 3.95–4.16 (1H, m), 6.10 (1H, d, J=8.2 Hz), 6.81 (1H, s), 7.08–7.20 (6H, m), 7.29–7.39 (10H, m), 7.61 (1H, dd, J=1.4, 8.6 Hz), 7.76–7.87 (3H, m), 8.06 (1H, s), 8.21 (1H, s). IR (KBr): 3416, 2932, 1651, 1601, 1524, 1495, 1445, 1319 cm$^{-1}$.

(ii) Production of N-Cyclohexyl-6-[1-hydroxy-1-(1H-imidazol-4-yl)-2-methylpropyl]-2-naphthamide In a similar manner to that described in Reference example 5, the reaction was carried out by using N-cyclohexyl-6-[1-hydroxy-2-methyl-1-(1-trityl-1H-imidazol-4-yl)propyl]-2-naphthamide (529 mg) to give the titled compound (241 mg) as a colorless powder.

$^1$H-NMR (CDCl$_3$) δ: 0.78 (3H, d, J=6.8 Hz), 1.00 (3H, d, J=6.8 Hz), 1.16–1.87 (8H, m), 1.98–2.14 (2H, m), 2.69 (1H, quintet, J=6.8 Hz), 3.91–4.12 (1H, m), 6.16 (1H, d, J=7.6 Hz), 6.99 (1H, s), 7.49 (1H, s), 7.60–7.85 (4H, m), 8.07 (1H, s), 8.17 (1H, s). IR (KBr): 3400–3100, 2932, 1638, 1535, 1466, 1323, 1140 cm$^{-1}$.

Example 33

Production of N-Cycloheptyl-6-[1-hydroxy-1-(1H-imidazol-4-yl)-2-methylpropyl]-2-naphthamide (i) Production of N-Cycloheptyl-6-[1-hydroxy-2-methyl-1-(1-trityl-1H-imidazol-4-yl)propyl]-2-naphthamide In a manner to that described in Example 9-(i), methyl 6-(1-hydroxy-2-methyl-1-(1-trityl-1H-imidazol-4-yl)propyl)-2-naphthoate (490 mg) was converted to 6-(1-hydroxy-2-methyl-1-(1-trityl-1H-imidazol-4-yl)propyl)-2-naphthoic acid, which was reacted with cycloheptylamine (0.20 mL) in a similar manner as described in Example 24-(i) to give the titled compound (560 mg) as a colorless powder.

$^1$H-NMR (CDCl$_3$) δ: 0.73 (3H, d, J=6.6 Hz), 0.96 (3H, d, J=6.6 Hz), 1.48–1.78 (10H, m), 2.01–2.18 (2H, m), 2.53 (1H, quintet, J=6.6 Hz), 3.75 (1H, s), 4.13–4.31 (1H, m), 6.16 (1H, d, J=7.8 Hz), 6.81 (1H, s), 7.06–7.19 (6H, m), 7.28–7.39 (10H, m), 7.61 (1H, dd, J=1.8, 8.8 Hz), 7.74–7.86 (3H, m), 8.05 (1H, s), 8.20 (1H, s). IR (KBr): 3418, 2930, 1651, 1601, 1516, 1445, 1323, 1163 cm$^{-1}$.

(ii) Production of N-Cycloheptyl-6-[1-hydroxy-1-(1H-imidazol-4-yl)-2-methylpropyl]-2-naphthamide In a similar manner to that described in Reference example 5, the reaction was carried out by using N-cycloheptyl-6-[1-hydroxy-2-methyl-1-(1-trityl-1H-imidazol-4-yl)propyl]-2-naphthamide (501 mg) to give the titled compound (221 mg) as a colorless powder.

$^1$H-NMR (CDCl$_3$) δ: 0.78 (3H, d, J=6.8 Hz), 1.01 (3H, d, J=6.8 Hz), 1.47–1.80 (10H, m), 1.97–2.16 (2H, m), 2.69 (1H, quintet, J=6.8 Hz), 4.12–4.28 (1H, m), 6.24 (1H, d, J=8.0 Hz), 6.99 (1H, s), 7.48 (1H, s), 7.60–7.85 (4H, m), 8.07 (1H, s), 8.16 (1H, s). IR (KBr): 3400–3100, 2928, 1626, 1537, 1460, 1325, 1138 cm$^{-1}$.

Example 34

Production of 6-[1-Hydroxy-1-(1H-imidazol-4-yl)-2-methylpropyl]-2-naphthamide (i) Production of 6-[1-Hydroxy-2-methyl-1-(1-trityl-1H-imidazol-4-yl)propyl]-2-naphthamide In a manner to that described in Example 9-(i), methyl 6-(1-hydroxy-2-methyl-1-(1-trityl-1H-imidazol-4-yl)propyl)-2-naphthoate (2.0 g) was converted to 6-(1-hydroxy-2-methyl-1-(1-trityl-1H-imidazol-4-yl)propyl)-2-naphthoic acid and this compound was dissolved in DMF (10 mL). Ammonium carbonate (558 mg), diphenylphosphorylazide (0.91 mL) and triethylamine (0.98 mL) were added and the resulting mixture was stirred at room temperature for 12 h. The mixture was diluted with water, extracted with ethyl acetate. The organic layer was washed with brine, dried and concentrated. The residue was purified by column chromatography (eluent; hexane:THF=1:2) to give the titled compound (1.96 g) as a colorless powder.

$^1$H-NMR (CDCl$_3$+CD$_3$OD) δ: 0.74 (3H, d, J=7.0 Hz), 0.97 (3H, d J=7.0 Hz), 2.55–2.68 (1H, m), 6.86 (1H, d, J=1.2 Hz), 7.09–7.14 (6H, m), 7.27–2.38 (10H, m), 7.63 (1H, d, J=1.7, 8.5 Hz), 7.82–7.85 (3H, m), 8.04 (1H, s), 8.33 (1H, s). IR (KBr): 3407, 3189, 2965, 1644, 1443, 748, 700 cm$^{-1}$.

(ii) 6-[1-Hydroxy-1-(1H-imidazol-4-yl)-2-methyl-propyl]-2-naphthamide

In a similar manner to that described in Reference example 5, the reaction was carried out by using 6-[1-hydroxy-2-methyl-1-(1-trityl-1H-imidazol-4-yl)propyl]-2-naphthamide (1.70 g) to give the titled compound (840 mg) as a colorless powder.

$^1$H-NMR (CDCl$_3$+CD$_3$OD) δ: 0.78 (3H, d, J=6.6 Hz), 1.00 (3H, d, J=7.0 Hz), 2.66–2.80 (1H, m), 7.00 (1H, d, J=1.0 Hz), 7.49 (1H, d, J=1.0 Hz), 7.63 (1H, d, J=1.8, 8.8 Hz), 7.77–7.81 (3H, m), 8.04 (1H, s), 8.29 (1H, s). IR (KBr): 3200, 2969, 1659, 1393, 816 cm$^{-1}$.

Example 35

Production of 1-Chloro-6-[1-hydroxy-1-(1H-imidazol-4-yl)-2-methylpropyl]-2-naphthamide (i) Production of 1-Chloro-6-[1-hydroxy-2-methyl-1-(1-trityl-1H-imidazol-4-yl)propyl]-2-naphthamide In a manner to that described in Example 9-(i), methyl 1-chloro-6-(1-hydroxy-2-methyl-1-(1-trityl-1H-imidazol-4-yl)propyl)-2-naphthoate (2.83 g) was converted to 1-chloro-6-(1-hydroxy-2-methyl-1-(1-trityl-1H-imidazol-4-yl)propyl)-2-naphthoic acid, which was reacted with 1-hydroxybenzotriazole ammonium salt (533 mg) in a similar manner as described in Example 24-(i) to give the titled compound (904 mg) as a colorless powder.

$^1$H-NMR (CDCl$_3$) δ: 0.72 (3H, d, J=6.6 Hz), 0.96 (3H, d, J=6.6 Hz), 2.47–2.61 (1H, m), 3.86 (1H, s), 6.30 (1H, br s), 6.38 (1H, br s), 6.83 (1H, d, J=1.2 Hz), 7.09–7.14 (6H, m), 7.29–7.35 (10H, m), 7.67 (1H, d, J=8.4 Hz), 7.72 (1H, dd, J=1.2, 8.4 Hz), 7.74 (1H, d, J=8.4 Hz), 8.06 (1H, s), 8.24 (1H, d, J=8.6 Hz). IR (KBr): 3177, 2966, 1670, 1445, 1394, 824, 748, 702 cm$^{-1}$.

(ii) Production of 1-Chloro-6-[1-(hydroxy-1-(1H-imidazol-4-yl)-2-methylpropyl]-2-naphthamide.

In a similar manner to that described in Reference example 5-(i), the reaction was carried out by using 1-chloro-6-[1-hydroxy-2-methyl-1-(1-trityl-1H-imidazol-4- yl)propyl)-1-methyl-2-naphthamide (8.00 g) to give the titled compound (1.50 g) as a colorless powder.

$^1$H-NMR (CDCl$_3$+CD$_3$OD) δ: 0.76 (3H, d, J=7.06 Hz), 1.00 (3H, d, J=6.6 Hz) 2.65–2.78 )1H, m), 6.99 (1H, d J=1.0 Hz), 7.43 (1H, d, J=1.0 Hz), 7.51 (1H, d, J=8.4 Hz), 7.72 (1H, d, J=8.4 Hz), 7.73 (1H, dd, J=1.6, 9.2 Hz), 8.04 (1H, d, J=1.6 Hz), 8.22 (1H, d, J=9.2 Hz). IR (KBr): 3281, 2970, 1661, 1393, 824, 733 cm$^{-1}$.

Example 36

Production of 6-[1-Hydroxy-1-(1H-imidazol-4-yl)-2-methylpropyl)-1-methyl-2-naphthamide (i) Production of 6-[1-Hydroxy-2-methyl-1-(1-trityl-1H-imidazol-4-yl)propyl)-1-methyl-2-naphthamide In a similar manner to that described in Example 35-(i), the reaction was carried out by using methyl 6-(1-hydroxy-2-methyl-1-(1-trityl-1H-imidazol-4-yl)propyl)-1-methyl-2-naphthoate (2.0 g) to give the titled compound (1.50 g) as a colorless powder.

$^1$H-NMR (CDCl$_3$) δ: 0.73 (3H, d, J=6.6 Hz), 0.96 (3H, d, J=6.6 Hz), 2.48–2.61 (1H, m), 2.78 (3H, s), 3.77 (1H, s), 5.86 (1H, br s), 6.05 (1H, br s), 6.82 (1H, d, J=1.0 Hz), 7.10–7.15 (6H, m), 7.29–7.35 (10H, m), 7.43 (1H, d, J=8.4 Hz), 7.65 (1H, d, J=8.6 Hz), 7.66 (1H, dd, J=1.8, 8.8 Hz), 7.96–8.00 (2H, m). IR (KBr): 3173, 2968, 1663, 1445, 824, 748, 702 cm$^{-1}$.

(ii) Production of 6-[1-Hydroxy-1-(1H-imidazol-4-yl)-2-methylpropyl)-1-methyl-2-naphthamide In a similar manner to that described in Reference example 5, the reaction was carried out by using 6-[1-hydroxy-2-methyl-1-(1-trityl-1H-imidazol-4-yl)propyl)-1-methyl-2-naphthamide (1.30 g) to give the titled compound (662 mg) as a colorless powder.

$^1$H-NMR (CDCl$_3$+CD$_3$OD) δ: 0.77 (3H, d, J=6.6 Hz), 0.99 (3H, d, J=6.6 Hz), 2.60–2.78 (1H, m), 2.70 (3H, s), 6.98 (1H, d, J=1.0 Hz), 7.35–7.42 (2H, m), 7.62–7.67 (2H, m), 7.94–7.98 (2H, m). IR (KBr): 3180, 2970, 1651, 1380, 822, 743 cm$^{-1}$.

Example 37

Production of 1-Chloro-6-[1-(hydroxy-1-(1H-imidazol-4-yl)-2-methylpropyl)-N-methyl-2-naphthamide (i) Production of 1-Chloro-6-[1-(hydroxy-2-methyl-1-(1-trityl-1H-imidazol-4-yl)propyl)-N-methyl-2-naphthamide In a similar manner to that described in Example 9-(i), the reaction was carried out by using methyl 1-chloro-6-(1-hydroxy-2-methyl-1-(1-trityl-1H-imidazol-4-yl)propyl)-2-naphthoate (2.0 g) to give the titled compound (1.50 g) as a colorless powder.

$^1$H-NMR (CDCl$_3$) δ: 0.71 (3H, d, J=7.0 Hz), 0.96 (3H, d, J=6.6 Hz), 2.46–2.60 (1H, m), 3.07 (3H, d, J=4.8 Hz), 3.81 (1H, s), 6.24 (1H, d, J=4.8 Hz), 6.82 (1H, d, J=0.6 Hz), 7.09–7.14 (6H, m), 7.31–7.34 (10H, m), 7.57 (1H, d, J=8.4 Hz), 7.69–7.73 (2H, m), 8.05 (1H, s), 8.22 (1H, d, J=8.8 Hz). IR (KBr): 3376, 2969, 1634, 1157, 1134, 702 cm$^{-1}$.

(ii) Production of 1-Chloro-6-[1-hydroxy-1-(1H-imidazol-4-yl)-2-methylpropyl)-N-methyl-2-naphthamide In a similar manner to that described in Reference example 5, the reaction was carried out by using 1-chloro-6-[1-hydroxy-2-methyl-1-(1-trityl-1H-imidazol-4-yl) propyl)-N-methyl-2-naphthamide (1.40 g) to give the titled compound (777 mg) as a colorless powder.

$^1$H-NMR (CDCl$_3$+CD$_3$OD) δ: 0.76 (3H, d, J=6.6 Hz), 0.99 (3H, d, J=6.6 Hz), 2.64–2.78 (1H, m), 3.01 (3H, d, J=1.4 Hz), 6.98 (1H, s), 7.41 (1H, dd, J=1.4, 8.6 Hz), 7.42 (1H, s), 7.69 (1H, d, J=7.8 Hz), 7.72 (1H, dd, J=1.4, 7.8 Hz), 8.01 (1H, s), 8.19 (1H, d, J=8.6 Hz). IR (KBr): 3242, 2970, 1630, 1553, 1333, 824 cm$^{-1}$.

Example 38

Production of 6-[1-Hydroxy-1-(1H-imidazol-4-yl)-2-methylpropyl)-N,1-dimethyl-2-naphthamide (i) Production of 6-[1-(Hydroxy-2-methyl-1-(1-trityl-1H-imidazol-4-yl)propyl)-N,1-dimethyl-2-naphthamide In a similar manner to that described in Example 9-(i), the reaction was carried out by using methyl 6-(1-hydroxy-2-methyl-1-(1-trityl-1H-imidazol-4-yl)propyl)-1-methyl-2-naphthoate (2.0 g) to give the titled compound (1.89 g) as a colorless powder.

$^1$H-NMR (CDCl$_3$) δ: 0.72 (3H, d, J=6.6 Hz), 0.95 (3H, d, J=6.6 Hz), 2.47–2.61 (1H, m), 2.70 (3H, s), 3.02 (3H, d, J=4.8 Hz), 3.75 (1H, s), 5.89 (1H, br s), 6.81 (1H, d, J=1.2 Hz), 7.09–7.14 (6H, m), 7.28–7.35 (1H, m), 7.59–7.68 (2H, m), 7.93–7.99 (2H, m). IR (KBr): 3407, 3250, 2971, 1634, 1495, 1157, 816, 702 cm$^{-1}$.

(ii) Production of 6-[1-(Hydroxy-1-(1H-imidazol-4-yl)-2-methylpropyl)-N,1-dimethyl-2-naphthamide In a similar manner to that described in Reference example 5, the reaction was carried out by using 6-[1-hydroxy-2-methyl-1-(1-trityl-1H-imidazol-4-yl)propyl)-N,1-dimethyl-2-naphthamide (1.60 g) to give the titled compound (843 mg) as a colorless powder.

$^1$H-NMR (CDCl$_3$+CD$_3$OD) δ: 0.78 (3H, d, J=7.0 Hz), 0.99 (3H, d, J=6.6 Hz), 2.65 (3H, s), 2.65–2.78 (1H, m), 2.98 (3H, s), 6.97 (1H, d, J=1.2 Hz), 7.31 (1H, d, J=8.4 Hz), 7.42 (1H, d, J=1.2 Hz), 7.61–7.67 (2H, m), 7.93–7.97 (2H, m). IR (KBr): 330, 2975, 1634, 1559, 1410, 1159, 822 cm$^{-1}$.

Example 39

Production of 6-[1-Hydroxy-1-(1H-imidazol-4-yl)-2-methyl-propyl)-N,3-dimethyl-2-naphthamide (i) Production of 6-[1-Hydroxy-2-methyl-1-(1-trityl-1H-imidazol-4-yl)propyl)-N,3-dimethyl-2-naphthamide In a similar manner to that described in Example 9-(i), the reaction was carried out by using 6-(1-hydroxy-2-methyl-1-(1-trityl-1H-imidazol-4-yl)propyl)-3-methyl-2-naphthoate (2.0 g) to give the titled compound (1.72 g) as a colorless powder.

$^1$H-NMR (CDCl$_3$+CD$_3$OD) δ: 0.72 (3H, d, J=6.6 Hz), 0.95 (3H, d, J=6.6 Hz), 2.54 (3H, s), 2.52–2.65 (1H, m), 2.99 (3H, d, J=4.0 Hz), 6.85 (1H, d, J=1.6 Hz), 7.10–7.15 (6H, m), 7.32–7.38 (10H, m), 7.53 (1H, dd, J=1.6, 8.6 Hz), 7.58 (1H, s), 7.69 (1H, d, J=8.6 Hz), 7.78 (1H, s), 7.89 (1H, s). IR (KBr): 3412, 3277, 2966, 1645, 1011, 746, 702 cm$^{-1}$.

(ii) Production of 6-[1-Hydroxy-1-(1H-imidazol-4-yl)-2-methylpropyl)-N.3-dimethyl-2-naphthamide In a similar manner to that described in Reference example 5, the reaction was carried out by using 6-[1-(hydroxy-2-methyl-1-(1-trityl-1H-imidazol-4-yl)propyl)-N,3-dimethyl-2-naphthamide (1.50 g) to give the titled compound (734 mg) as a colorless powder.

$^1$H-NMR (CDCl$_3$+CD$_3$OD) δ: 0.77 (3H, d, J=7.0 Hz), 0.99 (3H, d, J=6.6 Hz), 2.48 (3H, s), 2.61–2.74 (1H, m), 2.98 (3H, d, J=3.0 Hz), 6.95 (1H, d, J=1.2 Hz), 7.37 (1H, d, J=1.2 Hz), 7.50 (1H, dd, J=1.8, 8.8 Hz), 7.54 (1H, s), 7.64 (1H, d, J=8.8 Hz), 7.72 (1H, s), 7.88 (1H, s). IR (KBr): 3192, 2968, 1643, 1539, 1408, 1304, 1155, 908, 818 cm$^{-1}$.

Example 40

Production of 6-[1-Hydroxy-1-(1H-imidazol-4-yl)-2-methylpropyl)-3-methyl-2-naphthamide (i) Production of 6-[1-Hydroxy-2-methyl-1-(1-trityl-1H-imidazol-4-yl)propyl)-3-methyl-2-naphthamide In a similar manner to that described in Example 35-(i), the reaction was carried out by using methyl 6-(1-hydroxy-2-methyl-1-(1-trityl-1H-imidazol-4-yl)propyl)-3-methyl-2-naphthoate (2.0 g) to give the titled compound (1.50 g) as a pale yellow powder.

$^1$H-NMR (CDCl$_3$) δ: 0.72 (3H, d, J=7.0 Hz), 0.95 (3H, d, J=6.6 Hz), 2.45–2.59 (1H, m), 2.61 (3H, s), 3.77 (1H, s), 5.94 (2H, br s), 6.81 (1H, d, J=1.2 Hz), 7.10–7.16 (6H, m), 7.29–7.35 (10H, m), 7.55 (1H, dd, J=1.6, 8.6 Hz), 7.59 (1H, s), 7.69 (1H, d, J=8.8 Hz), 7.90 (1H, s), 7.94 (1H, s). IR (KBr): 3312, 2966, 1666, 1447, 748, 700 cm$^{-1}$.

(ii) Production of 6-[1-Hydroxy-1-(1H-imidazol-4-yl)-2-methylpropyl)-3-methyl-2-naphthamide In a similar manner to that described in Reference example 5, the reaction was carried out by using 6-[1-hydroxy-2-methyl-1-(1-trityl-1H-imidazol-4-yl)propyl)-3-methyl-2-naphthamide (1.40 g) to give the titled compound (734 mg) as a colorless powder.

$^1$H-NMR (CDCl$_3$+CD$_3$OD) δ: 0.77 (3H, d, J=6.6 Hz), 1.00 (3H, d, J=7.0 Hz), 2.55 (3H, s), 2.63–2.77 (1H, m), 6.98 (1H, s, J=1.2 Hz), 7.44 (1H, d, J=1.2 Hz), 7.54 (1H, dd, J=1.8, 8.8 Hz), 7.60 (1H, s), 7.69 (1H, d, J=8.8 Hz), 7.86 (1H, s), 7.91 (1H, s). IR (KBr): 3200, 2968, 1653, 1597, 1472, 1381, 907, 824 cm$^{-1}$.

Example 41

Production of 6-[1-(Hydroxy-1-(1H-imidazol-4-yl)-2-methylpropyl)-N,N-dimethyl-2-naphthamide (i) Production of 6-[1-(Hydroxy-2-methyl-1-(1-trityl-1H-imidazol-4-yl)propyl)-N,N-dimethyl-2-naphthamide In a manner to that described in Example 9-(i), methyl 6-(1-hydroxy-2-methyl-1-(1-trityl-1H-imidazol-4-yl)propyl)-2-naphthoate (2.0 g) was converted to 6-(1-hydroxy-2-methyl-1-(1-trityl-1H-imidazol-4-yl)propyl)-2-naphthoic acid, which was reacted with dimethylamine hydrochloride (346 mg) in a similar manner as described in Example 24-(i) to give the titled compound (1.87 g) as a colorless powder.

$^1$H-NMR (CDCl$_3$) δ: 0.74 (3H, d J=6.6 Hz), 0.96 (3H, d, J=6.6 Hz), 2.47–2.61 (1H, m), 3.04 (3H, br s), 3.14 (3H, br s), 3.76 (1H, s), 6.81 (1H, d, J=1.4 Hz), 7.10–7.16 (6H, m), 7.29–7.36 (10H, m), 7.47 (1H, dd, J=1.6, 8.2 Hz), 7.60 (1H, dd, J=1.8, 8.4 Hz), 7.76 (1H, d, J=8.8 Hz), 7.82 (1H, d, J=8.4 Hz), 7.85 (1H, s), 8.05 (1H, s). IR (KBr): 3161, 2932, 1626, 1493, 1447, 1391, 1167, 750, 700 cm$^{-1}$.

(ii) Production of 6-[1-(Hydroxy-1-(1H-imidazol-4-yl)-2-methylpropyl)-N,N-dimethyl-2-naphthamide In a similar manner to that described in Reference example 5, the reaction was carried out by using 6-[1-(hydroxy-2-methyl-1-(1-trityl-1H-imidazol-4-yl)propyl)-N,N-dimethyl-2-naphthamide (1.60 g) to give the titled compound (865 mg) as a pale yellow powder.

$^1$H-NMR (CDCl$_3$+CD$_3$OD) δ: 0.79 (3H, d, J=7.0 Hz), 1.00 (3H, d, J=7.0 Hz) 2.67–2.81 (1H, m), 3.04 (3H, br s), 3.15 (3H, br s), 6.99 (1H, d, J=1.2 Hz), 7.44 (1H, dd, J=1.8, 8.4 Hz), 7.48 (1H, d, J=1.2 Hz), 7.65 (1H, dd, J=1.8, 8.6 Hz), 7.78 (1H, d, J=8.8 Hz), 7.84–7.88 (2H, m), 8.05 (1H, s). IR (KBr): 3200, 2965, 1615, 1505, 1395, 820 cm$^{-1}$.

Example 42

Production of 1-(1H-Imidazol-4-yl)-2-methyl-1-[6-(1-pyrrolidinylcarbonyl)-2-naphthyl]-1-propanol (i) Production of 2-Methyl-1-[6-(1-pyrrolidinylcarbonyl)-2-naphthyl]-1-(1-trityl-1H-imidazol-4-yl)-1-propanol In a manner to that described in Example 9-(i), methyl 6-(1-hydroxy-2-methyl-1-(1-trityl-1H-imidazol-4-yl)propyl)-2-naphthoate (2.83 g) was converted to 6-(1-hydroxy-2-methyl-1-(1-trityl-1H-imidazol-4-yl)propyl)-2-naphthoic acid, which was reacted with pyrrolidine (0.13 mL) in a similar manner as described in Example 24-(i) to give the titled compound (550 mg) as a colorless powder.

$^1$H-NMR (CDCl$_3$) δ: 0.74 (3H, d, J=6.6 Hz), 0.96 (3H, d, J=6.6 Hz), 1.82–2.10 (4H, m), 2.53 (1H, quintet, J=6.6 Hz), 3.49 (2H, t, J=6.6 Hz), 3.70 (2H, t, J=6.6 Hz), 3.73 (1H, s), 6.81 (1H, d, J=1.0 Hz), 7.07–7.18 (6H, m), 7.28–7.39 (10H, m), 7.56–7.65 (2H, m), 7.79 (1H, d, J=8.6 Hz), 7.82 (1H, d, J=8.6 Hz), 7.96 (1H, s), 8.05 (1H, s). IR (KBr): 2971, 1615, 1568, 1489, 1445, 1429, 1339, 1250, 1229 cm$^{-1}$.

(ii) Production of 1-(1H-Imidazol-4-yl)-2-methyl-1-[6-(1-pyrrolidinylcarbonyl)-2-naphthyl]-1-propanol In a similar manner to that described in Reference example 5, the reaction was carried out by using 2-methyl-1-(6-(1-pyrrolidinylcarbonyl)-2-naphthyl]-1-(1-trityl-1H-imidazol-4-yl)-1-propanol (500 mg) to give the titled compound (296 mg) as a colorless powder.

$^1$H-NMR (CDCl$_3$) δ: 0.77 (3H, d, J=6.8 Hz), 0.98 (3H, d, J=6.8 Hz), 1.80–2.07 (4H, m), 2.65 (1H, quintet, J=6.8 Hz), 3.47 (2H, t, J=6.3 Hz), 3.68 (2H, t, J=6.9 Hz), 6.89 (1H, s), 7.34 (1H, s), 7.52 (1H, dd, J=1.6, 8.4 Hz), 7.59 (1H, dd, J=1.6, 8.4 Hz), 7.72 (1H, d, J=8.8 Hz), 7.78 (1H, d, J=8.6 Hz), 7.90 (1H, s), 8.03 (1H, s). IR (KBr): 3156, 2975, 1611, 1566, 1481, 1304, 1142 cm$^{-1}$.

Example 43

Production of 6-[1-Hydroxy-1-(1H-imidazol-4-yl)-2-methylpropyl]-N-(1,3-thiazol-2-yl)-2-naphthamide (i) Production of 6-[1-Hydroxy-2-methyl-1-(1-trityl-1H-imidazol-4-yl)propyl]-N-(1,3-thiazol-2-yl)-2-naphthamide In a manner to that described in Example 9-(i), methyl 6-(1-hydroxy-2-methyl-1-(1-trityl-1H-imidazol-4-yl)propyl)-2-naphthoate (570 mg) was converted to 6-(1-hydroxy-2-methyl-1-(1-trityl-1H-imidazol-4-yl)propyl)-2-naphthoic acid, which was reacted with 2-aminothiazole (150 mg) in a similar manner as described in Example 24-(i) to give the titled compound (370 mg) as a colorless powder.

$^1$H-NMR (CDCl$_3$) δ: 0.74 (3H, d, J=6.6 Hz), 1.01 (3H, d, J=6.6 Hz), 2.56 (1H, quintet, J=6.6 Hz), 4.35 (1H, brs), 6.87 (1H, d, J=1.2 Hz), 6.97 (1H, d, J=3.6 Hz), 7.06–7.19 (6H, m), 7.25–7.38 (11H, m), 7.60 (1H, dd, J=1.6, 8.6 Hz), 7.70 (1H, d, J=8.8 Hz), 7.78 (1H, d, J=8.8 Hz), 7.91 (1H, dd, J=1.6, 8.6 Hz), 8.09 (1H, s), 8.31 (1H, s). IR (KBr): 2969, 1669, 1632, 1549, 1493, 1302, 1231, 1192, 1161 cm$^{-1}$.

(ii) Production of 6-[1-Hydroxy-1-(1H-imidazol-4-yl)-2-methylpropyl]-N-(1,3-thiazol-2-yl)-2-naphthamide In a similar manner to that described in Reference example 5, the reaction was carried out by using 6-[1-hydroxy-2-methyl-1-(1-trityl-1H-imidazol-4-yl)propyl]-N-(1,3-thiazol-2-yl)-2-naphthamide (320 mg) to give the titled compound (200 mg) as a colorless powder.

$^1$H-NMR (DMSO-d$_6$+TFA) δ: 0.74 (3H, d, J=6.6 Hz), 0.99 (3H, d, J=6.6 Hz), 2.85 (1H, quintet, J=6.6 Hz), 7.30 (1H, d, J=3.6 Hz), 7.59 (1H, d, J=3.6 Hz), 7.71 (1H, dd, J=1.6, 8.6 Hz), 7.77 (1H, s), 8.00–8.19 (4H, m), 8.76 (1H, s), 9.00 (1H, s). IR (KBr): 3400–3100, 2969, 1667, 1632, 1549, 1489, 1470, 1302, 1134 cm$^{-1}$.

Example 44

Production of N-Ethoxy-6-(1-hydroxy-1-(1H-imidazol-4-yl)-2-methylpropyl)-2-naphthamide (i) N-Ethoxy-6-(1-hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)

propyl)-2-naphthoate (1.77 g) was converted to 6-(1-hydroxy-2-methyl-1-(1-trityl-1H-imidazol-4-yl)propyl)-2-naphthoic acid, which was reacted with O-ethylhydroxylamine hydrochloride (367 mg) in a similar manner as described in Example 24-(i) to give the titled compound (1.44 g) as a colorless powder.

¹H-NMR (CDCl₃) δ: 0.72 (3H, d, J=7.0 Hz), 0.96 (3H, d, J=6.6 Hz), 1.34 (3H, t, J=7.0 Hz), 2.45–2.59 (1H, m), 3.78 (1H, s), 4.12 (2H, q, J=7.0 Hz), 6.83 (1H, d, J=1.6 Hz), 7.09–7.16 (6H, m), 7.28–7.36 (10H, m), 7.58 (1H, dd, J=1.6, 8.6 Hz), 7.62–7.76 (3H, m), 8.00 (1H, s), 8.15 (1H, s), 9.31 (1H, s). IR (KBr): 3370, 2966, 1661, 1495, 1445, 1240, 816, 700 cm⁻¹.

(ii) Production of N-Ethoxy-6-[1-(hydroxy-1-(1H-imidazol-4-yl)-2-methylpropyl)-2-naphthamide In a similar manner to that described in Reference example 5, the reaction was carried out by using N-ethoxy-6-[1-(hydroxy-2-methyl-1-(1-trityl-1H-imidazol-4-yl)propyl)-2-naphthamide (1.30 g) to give the titled compound (511 mg) as a colorless powder.

¹H-NMR (CDCl₃+CD₃OD) δ: 0.79 (3H, d, J=6.6 Hz), 1.01 (3H, d, J=6.6 Hz), 1.35 (3H, t, J=7.0 Hz), 2.68–2.82 (1H, m), 4.09 (2H, q, J=7.0 Hz), 7.02 (1H, d, J=1.2 Hz), 7.52 (1H, d, J=1.2 Hz), 7.66 (1H, d, J=8.0 Hz), 7.76 (1H, d, J=1.6, 8.8 Hz), 7.81–7.88 (2H, m), 8.05 (1H, s), 8.23 (1H, s). IR (KBr): 3271, 2988, 1622, 1007, 818, 737 cm⁻¹.

Example 45

Production of 6-[1-Hydroxy-1-(1H-imidazol-4-yl)-2-methylpropyl)-N-isopropoxy-2-naphthamide (i) Production of 6-[1-Hydroxy-2-methyl-1-(1-trityl-1H-imidazol-4-yl)propyl)-N-isopropoxy-2-naphthamide In a manner to that described in Example 9-(i), methyl 6-(1-hydroxy-2-methyl-1-(1-trityl-1H-imidazol-4-yl)propyl)-2-naphthoate (1.77 g) was converted to 6-(1-hydroxy-2-methyl-1-(1-trityl-1H-imidazol-4-yl)propyl)-2-naphthoic acid, which was reacted with O-isopropylhydroxylamine hydrochloride (420 mg) in a similar manner as described in Example 24-(i) to give the titled compound (1.46 g) as a pale yellow powder.

¹H-NMR (CDCl₃) δ: 0.72 (3H, d, J=7.0 Hz), 0.96 (3H, d, J=6.6 Hz), 1.34 (6H, d, J=5.8 Hz), 2.46–2.59 (1H, m), 3.78 (1H, s), 4.25–4.37 (1H, m), 6.82 (1H, d, J=1.0 Hz), 7.09–7.16 (6H, m), 7.29–7.36 (10H, m), 7.60 (1H, dd, J=1.4, 8.8 Hz), 7.68–7.80 (3H, m), 8.02 (1H, s), 8.17 (1H, s), 8.91 (1H, s). IR (KBr): 3418, 3140, 2978, 1655, 1493, 1443, 1161, 746, 700 cm⁻¹.

(ii) Production of 6-(1-Hydroxy-1-(1H-imidazol-4-yl)-2-methylpropyl)-N-isopropoxy-2-naphthamide In a similar manner to that described in Reference example 5, the reaction was carried out by using 6-(1-hydroxy-2-methyl-1-(1-trityl-1H-imidazol-4-yl)propyl)-N-isopropoxy-2-naphthamide (1.30 g) to give the titled compound (677 mg) as a colorless powder.

¹H-NMR (CDCl₃+CD₃OD) δ: 0.76 (3H, d, J=6.8 Hz), 0.99 (3H, d, J=6.6 Hz), 1.31 (6H, d, J=6.4 Hz), 2.62–2.75 (1H, m), 4.21–4.33 (1H, m), 6.98 (1H, d, J=1.0 Hz), 7.43 (1H, d, J=1.0 Hz), 7.56 (1H, dd, J=1.7, 8.5 Hz), 7.65 (1H, dd, J=1.8, 7.0 Hz), 7.68–7.74 (2H, m), 8.0 (1H, s), 8.11 (1H, s). IR (KBr): 3200, 2974, 1645, 1383, 1113, 822 cm⁻¹.

Example 46

Production of N-(2-Hydroxyethyl)-6-[1-hydroxy-1-(1H-imidazol-4-yl)-2-methylpropyl)-2-naphthamide (i) Production of N-(2-Hydroxyethyl)-6-[1-hydroxy-2-methyl-1-(1-trityl-1H-imidazol-4-yl)propyl)-2-naphthamide In a manner to that described in Example 9-(i), methyl 6-(1-hydroxy-2-methyl-1-(1-trityl-1H-imidazol-4-yl)propyl)-2-naphthoate (2.0 g) was converted to 6-(1-hydroxy-2-methyl-1-(1-trityl-1H-imidazol-4-yl)propyl)-2-naphthoic acid, which was reacted with ethanolamine (0.26 mL) in a similar manner as described in Example 24-(i) to give the titled compound (1.74 g) as a colorless powder.

¹H-NMR (CDCl₃) δ: 0.72 (3H, d, J=6.6 Hz), 0.97 (3H, d, J=6.6 Hz), 2.46–2.60 (1H, m), 3.59–3.66 (2H, m), 3.78–3.83 (2H, m), 3.92 (1H, br s), 6.83 (1H, d, J=1.6 Hz), 7.04–7.15 (7H, m), 7.24–7.36 (10H, m), 7.56 (1H, dd, J=1.6, 8.6 Hz), 7.66–7.70 (3H, m), 7.99 (1H, s), 8.18 (1H, s). IR (KBr) 3300, 1624, 1537, 1493, 1445, 1315, 1242, 1159, 746, 702 cm⁻¹.

(ii) Production of N-(2-Hydroxyethyl)-6-[1-hydroxy-1-(1H-imidazol-4-yl)-2-methylpropyl)-2-naphthamide In a similar manner to that described in Reference example 5, the reaction was carried out by using N-(2-hydroxyethyl)-6-[1-(hydroxy-2-methyl-1-(1-trityl-1H-imidazol-4-yl)propyl)-2-naphthamide (1.50 g) to give the titled compound (779 mg) as a colorless powder.

¹H-NMR (CDCl₃+CD₃OD) δ: 0.77 (3H, d, J=7.0 Hz), 1.00 (3H, d, J=6.6 Hz), 2.64–2.78 (1H, m), 3.55–3.60 (2H, m), 3.75–3.80 (2H, m), 6.99 (1H, d, J=1.0 Hz), 7.47 (1H, d, J=1.0 Hz), 7.59 (1H, dd, J=1.8, 8.8 Hz), 7.71–7.76 (3H, m), 8.00 (1H, d, J=0.8 Hz), 8.21 (1H, s). IR (KBr): 3300, 2971, 1636, 1541, 1300, 1067, 820 cm⁻¹.

Example 47

Production of Ethyl [[6-(1-Hydroxy-1-(1H-imidazol-4-yl)-2-methylpropyl)-2-naphthoyl]amino]acetate (i) Production of Ethyl [[6-(1-Hydroxy-2-methyl-1-(1-trityl-1H-imidazol-4-yl)propyl)-2-naphthoyl]amino]acetate In a manner to that described in Example 9-(i), methyl 6-(1-hydroxy-2-methyl-1-(1-trityl-1H-imidazol-4-yl)propyl)-2-naphthoate (533 mg) was converted to 6-(1-hydroxy-2-methyl-1-(1-trityl-1H-imidazol-4-yl)propyl)-2-naphthoic acid, which was reacted with glycine ethyl ester hydrochloride (242 mg) in a similar manner as described in Example 24-(i) to give the titled compound (600 mg) as a colorless powder.

¹H-NMR (CDCl₃) δ: 0.74 (3H, d, J=7.0 Hz), 0.97 (3H, d, J=6.6 Hz), 1.34 (3H, t, J=7.4 Hz), 2.50–2.57 (1H, m), 3.76 (1H, m), 4.28 (2H, q, J=7.4 Hz), 4.31 (2H, s), 6.81–6.82 (2H, m), 7.10–7.15 (6H, m), 7.30–7.35 (10H, m), 7.62 (1H, dd, J=2.0, 10.8 Hz), 7.80–7.85 (3H, m), 8.08 (1H, s), 8.29 (1H, s). IR (KBr): 1748, 1651, 1534, 1495, 1198, 747, 733, 702 cm⁻¹.

(ii) Production of Ethyl [[6-[1-Hydroxy-1-(1H-imidazol-4-yl)-2-methylpropyl)-2-naphthoyl]amino]acetate In a similar manner to that described in Reference example 5, the reaction was carried out by using ethyl [[6-[1-hydroxy-2-methyl-1-(1-trityl-1H-imidazol-4-yl)propyl)-2-naphthoyl]amino]acetate (765 mg) to give the titled compound (425 mg) as a colorless powder.

¹H-NMR (CDCl₃+CD₃OD) δ: 0.80 (3H, d, J=6.6 Hz), 1.02 (3H, d, J=6.2 Hz), 1.33 (3H, t, J=7.0 Hz), 2.75 (1H, br s), 4.22–4.32 (4H, m), 7.02 (1H, d, J=1.2 Hz), 7.53 (1H, s), 7.69 (1H, br s), 7.84–7.92 (3H, m), 8.07 (1H, br s), 8.32 (1H, s). IR (KBr): 2975, 1740, 1645, 1541, 1487, 1447, 1377, 1211 cm⁻¹.

Example 48

Production of Methyl (2S)-2-[[6-[1-Hydroxy-1-(1H-imidazol-4-yl)-2-methylpropyl)-2-naphthoyl]amino]propanoate (i) Production of Methyl (2S)-2-[[6-[1-Hydroxy-2-methyl-1-(1-trityl-1H-imidazol-4-yl)propyl)-2-naphthoyl]amino]propanoate In a manner to that described in Example 9-(i), methyl 6-(1-hydroxy-2-methyl-1-(1-trityl-1H-imidazol-4-yl)propyl)-2-naphthoate (533 mg) was converted to 6-(1-hydroxy-2-methyl-1-(1-trityl-1H-imidazol-4-yl)propyl)-2-naphthoic acid, which was reacted with L-alanine methyl ester hydrochloride (283 mg) in a similar manner as described in Example 24-(i) to give the titled compound (604 mg) as a colorless powder.

$^1$H-NMR (CDCl$_3$) δ: 0.74 (3H, d, J=6.6 Hz), 0.97 (3H, d, J=7.0 Hz), 1.57 (3H, t, J=7.0 Hz), 2.50–2.60 (1H, m), 3.76 (1H, s), 3.82 (3H, s), 4.80–5.00 (1H, m), 6.81–6.88 (2H, m), 7.10–7.15 (6H, m), 7.31–7.34 (10H, m), 7.60–7.65 (1H, m), 7.80–7.84 (3H, m), 8.07 (1H, s), 8.28 (1H, s). IR (KBr): 1744, 1651, 1532, 1495, 1447, 1165, 747, 733, 702 cm$^{-1}$.

(ii) Production of Methyl (2S)-2-[[6-[1-Hydroxy-1-(1H-imidazol-4-yl)-2-methylpropyl)-2-naphthoyl]amino]propanoate In a similar manner to that described in Reference example 5, the reaction was carried out by using methyl (2S)-2-[[6-[1-hydroxy-2-methyl-1-(1-trityl-1H-imidazol-4-yl)propyl)-2-naphthoyl]amino]propanoate (574 mg) to give the titled compound (326 mg) as a colorless powder.

$^1$H-NMR (CDCl$_3$+CD$_3$OD) δ: 0.79 (3H, d, J=6.6 Hz), 1.01 (3H, d, J=6.6 Hz), 1.56 (3H, d, J=7.0 Hz), 2.65–2.78 (1H, m), 3.80 (3H, s), 4.76–4.87 (1H, m), 7.00 (1H, s), 7.51 (1H, s), 7.63 (1H, d, J=8.2 Hz), 7.78–7.81 (3H, m), 8.02 (1H, s), 8.25 (1H, s). IR (KBr): 1736, 1645, 1537, 1454, 1221, 1165, 814 cm$^{-1}$.

Example 49

Production of Methyl (2R)-2-[[6-[1-Hydroxy-1-(1H-imidazol-4-yl)-2-methylpropyl)-2-naphthoyl]amino]propanoate (i) Production of Methyl (2R)-2-[[6-[1-Hydroxy-2-methyl-1-(1-trityl-1H-imidazol-4-yl)propyl)-2-naphthoyl]amino]propanoate In a manner to that described in Example 9-(i), methyl 6-(1-hydroxy-2-methyl-1-(1-trityl-1H-imidazol-4-yl)propyl)-2-naphthoate (622 mg) was converted to 6-(1-hydroxy-2-methyl-1-(1-trityl-1H-imidazol-4-yl)propyl)-2-naphthoic acid, which was reacted with D-alanine methyl ester hydrochloride (283 mg) in a similar manner as described in Example 24-(i) to give the titled compound (622 mg) as a colorless powder.

$^1$H-NMR (CDCl$_3$) δ: 0.73 (3H, d, J=6.6 Hz), 0.97 (3H, d, J=6.6 Hz), 1.57 (3H, t, J=7.0 Hz), 2.50–2.60 (1H, m), 3.76 (1H, s), 3.82 (3H, s), 4.80–4.95 (1H, m), 6.81–6.88 (2H, m), 7.10–7.16 (6H, m), 7.29–7.36 (10H, m), 7.62 (1H, dd, J=1.8, 8.8 Hz), 7.80–7.88 (3H, m), 8.07 (1H, s), 8.28 (1H, s). IR (KBr): 1742, 1651, 1532, 1495, 1447, 1163, 747, 733, 702 cm$^{-1}$.

(ii) Production of Methyl (2R)-2-[[6-[1-Hydroxy-1-(1H-imidazol-4-yl)-2-methylpropyl)-2-naphthoyl]amino]propanoate In a similar manner to that described in Reference example 5, the reaction was carried out by using methyl (2R)-2-[[6-[1-hydroxy-2-methyl-1-(1-trityl-1H-imidazol-4-yl)propyl)-2-naphthoyl]amino]propanoate (592 mg) to give the titled compound (335 mg) as a colorless powder.

$^1$H-NMR (CDCl$_3$+CD$_3$OD) δ: 0.80 (3H, d, J=7.0 Hz), 1.01 (3H, d, J=6.4 Hz), 1.56 (3H, d, J=7.0 Hz), 2.66–2.80 (1H, m), 3.81 (3H, s), 4.77–4.86 (1H, m), 7.01 (1H, s), 7.55 (1H, s), 7.64 (1H, d, J=8.0 Hz), 7.80–7.82 (3H, m), 8.02 (1H, s), 8.27 (1H, s). IR (KBr): 1738, 1645, 1537, 1453, 1219, 1165, 812 cm$^{-1}$.

Example 50

Production of 6-[1-Hydroxy-(1H-imidazol-4-yl)ethyl]-N-methyl-2-naphthamide (i) Production of 6-[1-Hydroxy-(1-trityl-1H-imidazol-4-yl)ethyl]-N-methyl-2-naphthamide A solution of methylmagnesium bromide in diethyl ether (3M; 2 mL) was added to a solution of N-methyl-6-[(1-trityl-1H-imidazol-4-yl)carbonyl]-2-naphthamide (500 mg) in THF (10 mL) under ice cooling. The mixture was stirred for 20 min, diluted with water, extracted with ethyl acetate. The organic layer was washed with brine, dried and concentrated. The obtained solid was washed with a mixed solution of hexane-ethyl acetate (1:1) to give the titled compound (506 mg) as a colorless powder.

$^1$H-NMR (CDCl$_3$) δ: 1.84 (3H, s), 3.07 (3H, d, J=4.8 Hz), 3.81 (1H, s), 6.37 (1H, d, J=4.8 Hz), 6.81 (1H, d, J=1.4 Hz), 7.14–7.21 (6H, m), 7.33–7.37 (9H, m), 7.42 (1H, d, J=1.4 Hz), 7.48 (1H, dd, J=1.7, 8.5 Hz), 7.72–7.77 (3H, m), 7.89 (1H, s), 8.20 (1H, s). IR (KBr): 3422, 2982, 1651, 1539, 1493, 1445, 1306, 750, 700 cm$^{-1}$.

(ii) Production of 6-[1-Hydroxy-(1H-imidazol-4-yl)ethyl]-N-methyl-2-naphthamide

In a similar manner to that described in Reference example 5, the reaction was carried out by using 6-[1-hydroxy-(1-trityl-1H-imidazol-4-yl)ethyl]-N-methyl-2-naphthamide (400 mg) to give the titled compound (172 mg) as a colorless powder.

$^1$H-NMR (CDCl$_3$+CD$_3$OD) δ: 1.94 (3H, s), 2.99 (3H, d, J=3.0 Hz), 6.89 (1H, d, J=1.2 Hz), 7.50–7.55 (2H, m), 7.73 (1H, d, J=4.4 Hz), 7.77–7.81 (3H, m), 7.91 (1H, s), 8.23 (1H, s). IR (KBr): 3255, 1628, 1541, 1412, 1308, 1123, 897, 820, 768 cm$^{-1}$.

Example 51

Production of 6-[1-Hydroxy-1-(1H-imidazol-4-yl)propyl]-N-methyl-2-naphthamide (i) Production of 6-[1-Hydroxy-1-(1-trityl-1H-imidazol-4-yl)-2-propenyl]-N-methyl-2-naphthamide The similar reaction as described in Example 50-(i) was carried out by using N-methyl-6-[(1-trityl-1H-imidazol-4-yl)carbonyl]-2-naphthamide (700 mg) and vinylmagnesium bromide in THF (1M; 5 mL) to give the titled compound (478 mg) as colorless powder.

$^1$H-NMR (CDCl$_3$) δ: 3.06 (3H, d, J=4.8 Hz), 3.98 (1H, s), 5.23 (1H, dd, J=1.2, 10.4 Hz), 5.27 (1H, dd, J=1.2, 17.2 Hz), 6.39 (1H, br s), 6.42 (1H, dd, J=10.4, 17.2 Hz), 6.72 (1H, d, J=1.0 Hz), 7.10–7.19 (6H, m), 7.30–7.37 (9H, m), 7.45 (1H, d, J=1.4 Hz), 7.51 (1H, dd, J=1.7, 8.7 Hz), 7.72–7.76 (3H, m), 7.83 (1H, s), 8.19 (1H, s). IR (KBr): 3302, 1645, 1585, 1493, 1447, 1157, 908, 746, 733, 700 cm$^{-1}$.

(ii) Production of 6-[1-Hydroxy-1-(1-trityl-1H-imidazol-4-yl)propyl]-N-methyl-2-naphthamide A mixture of 6-[1-hydroxy-1-(1-trityl-1H-imidazol-4-yl)-2-propenyl]-N-methyl-2-naphthamide (444 mg) and 10% palladium carbon (50% wet; 100 mg) in ethyl acetate (6 mL) was stirred for 12 h at room temperature under hydrogen atmosphere. The catalyst was filtered off, and the filtrate was concentrated and crystallized from ethyl acetate to give the titled compound (359 mg) as a pale yellow powder.

¹H-NMR (CDCl₃) δ: 0.84 (3H, t, J=7.2 Hz), 2.07–2.29 (2H, m), 3.06 (3H, d, J=5.2 Hz), 3.65 (1H, br s), 6.41 (1H, d, J=5.2 Hz), 6.80 (1H, d, J=1.4 Hz), 7.10–7.19 (6H, m), 7.31–7.34 (9H, m), 7.39 (1H, d, J=1.4 Hz), 7.48 (1H, dd, J=1.9, 8.5 Hz), 7.74–7.78 (3H, m), 7.96 (1H, s), 8.21 (1H, s). IR (KBr): 3406, 2976, 1651, 1541, 1493, 1445, 1306, 1248, 750, 700 cm⁻¹.

(iii) Production of 6-[1-Hydroxy-1-(1H-imidazol-4-yl)propyl]-N-methyl-2-naphthamide In a similar manner to that described in Reference example 5, the reaction was carried out by using 6-[1-hydroxy-1-(1-trityl-1H-imidazol-4-yl)propyl]-N-methyl-2-naphthamide (230 mg) to give the titled compound (112 mg) as a colorless powder.

¹H-NMR (CDCl₃+CD₃OD) δ: 0.85 (3H, t, J=7.2 Hz), 2.18–2.40 (2H, m), 3.01 (3H, d, J=4.0 Hz), 6.89 (1H, s), 7.26 (1H, br s), 7.45–7.48 (2H, m), 7.73–7.81 (3H, m), 7.94 (1H, s), 8.19 (1H, s). IR (KBr): 3300, 1638, 1545, 1412, 1308, 1121, 895, 818 cm⁻¹.

Example 52

Production of 6-[Cyclopropyl-hydroxy-(1H-imidazol-4-yl)methyl]-N-methyl-2-naphthamide (i) Production of 6-[Cyclopropyl-hydroxy-(1-trityl-1H-imidazol-4-yl)methyl]-N-methyl-2-naphthamide The similar reaction as described in Example 50-(i) was carried out by using N-methyl-6-[(1-trityl-1H-imidazol-4-yl)carbonyl]-2-naphthamide (500 mg) and cyclopropyl-magnesium bromide in THF (1M; 4 mL) to give the titled compound (332 mg) as colorless powder.

¹H-NMR (CDCl₃) δ: 0.40–0.55 (4H, m), 1.48–1.62 (1H, m), 3.06 (1H, d, J=4.8 Hz), 3.53 (1H, s), 6.34 (1H, d, J=4.8 Hz), 6.83 (1H, d, J=1.4 Hz), 7.11–7.20 (6H, m), 7.31–7.36 (9H, m), 7.39 (1H, d, J=1.0 Hz), 7.56 (1H, dd, J=1.7, 8.7 Hz), 7.72–7.82 (3H, m), 7.96 (1H, s), 8.21 (1H, s). IR (KBr): 3294, 1650, 1553, 1495, 1445, 1306, 1123, 1024, 746, 702 cm⁻¹.

(ii) Production of 6-[Cyclopropyl-hydroxy-(1H-imidazol-4-yl)methyl]-N-methyl-2-naphthamide In a similar manner to that described in Reference example 5, the reaction was carried out by using 6-[cyclopropyl-hydroxy-(1-trityl-1H-imidazol-4-yl)methyl]-N-methyl-2-naphthamide (280 mg) to give the titled compound (73 mg) as a colorless powder.

¹H-NMR (CDCl₃+CD₃OD) δ: 0.41–0.67 (4H, m), 1.59–1.72 (1H, m), 3.00 (3H, d, J=2.8 Hz), 7.07 (1H, d, J=1.2 Hz), 7.51–7.57 (2H, m), 7.68 (1H, d, J=4.8 Hz), 7.76–7.85 (3H, m), 7.92 (1H, s), 8.24 (1H, s). IR (KBr): 3300, 1638, 1545, 1412, 1308, 1121, 895, 818 cm⁻¹.

Example 53

Production of 6-[1-Hydroxy-(1H-imidazol-4-yl)butyl]-N-methyl-2-naphthamide (i) Production of 6-[1-Hydroxy-1-(1-trityl-1H-imidazol-4-yl)-3-butenyl]-N-methyl-2-naphthamide The similar reaction as described in Example 50-(i) was carried out by using N-methyl-6-[(1-trityl-1H-imidazol-4-yl)carbonyl]-2-naphthamide (700 mg) and allyl-magnesium bromide in THF (1M; 7 mL) to give the titled compound (659 mg) as colorless powder.

¹H-NMR (CDCl₃) δ: 2.85–3.11 (2H, m), 3.06 (3H, d, J=4.8 Hz), 3.59 (1H, s), 5.03–5.11 (2H, m), 5.60–5.81 (1H, m), 6.36 (1H, d, J=4.8 Hz), 6.81 (1H, d, J=1.4 Hz), 7.11–7.18 (6H, m), 7.30–7.37 (9H, m), 7.40 (1H, d, J=1.2 Hz), 7.59 (1H, dd, J=2.0, 8.8 Hz), 7.74–7.84 (3H, m), 7.97 (1H, s), 8.22 (1H, s). IR (KBr): 3294, 1659, 1549, 1445, 1306, 1121, 748, 702 cm⁻¹.

(ii) Production of 6-[1-Hydroxy-(1-trityl-1H-imidazol-4-yl)butyl]-N-methyl-2-naphthamide In a similar manner to that described in Example 51-(ii), the reaction was carried out by using 6-[1-hydroxy-(1-trityl-1H-imidazol-4-yl)-3-butenyl]-N-methyl-2-naphthamide (570 mg) to give the titled compound (485 mg) as a colorless powder.

¹H-NMR (CDCl₃) δ: 0.83 (3H, t, J=7.2 Hz), 1.06–1.52 (2H, m), 2.07–2.18 (2H, m), 3.05 (3H, d, J=4.8 Hz), 3.69 (1H, s), 6.40 (1H, d, J=4.8 Hz), 6.79 (1H, d, J=1.6 Hz), 7.10–7.19 (6H, m), 7.31–7.35 (9H, m), 7.38 (1H, d, J=1.6 Hz), 7.48 (1H, dd, J=1.6, 8.6 Hz), 7.73–7.78 (3H, m), 7.96 (1H, s), 8.21 (1H, s). IR (KBr): 3229, 2961, 1641, 1560, 1491, 1445, 1327, 1169, 700 cm⁻¹.

(iii) Production of 6-[1-Hydroxy-1-(1H-imidazol-4-yl)butyl]-N-methyl-2-naphthamide In a similar manner to that described in Reference example 5, the reaction was carried out by using 6-[1-hydroxy-(1-trityl-1H-imidazol-4-yl)butyl]-N-methyl-2-naphthamide (400 mg) to give the titled compound (179 mg) as a colorless powder.

¹H-NMR (CDCl₃+CD₃OD) δ: 0.87 (3H, t, J=7.2 Hz), 1.01–1.26 (1H, m), 1.32–1.54 (1H, m), 2.10–2.36 (2H, m), 3.01 (3H, d, J=3.4 Hz), 6.89 (1H, d, J=1.2 Hz), 7.20 (1H, d, J=4.0 Hz), 7.44–7.49 (2H, m), 7.71–7.81 (3H, m), 7.94 (1H, s), 8.19 (1H, s). IR (KBr): 3300, 2961, 1634, 1539, 1412, 1308, 1123, 818 cm⁻¹.

Example 54

Production of 6-[1-Hydroxy-1-(1H-imidazol-4-yl)-3-methylbutyl]-N-methyl-2-naphthamide (i) Production of 6-[1-Hydroxy-3-methyl-1-(1-trityl-1H-imidazol-4-yl)butyl]-N-methyl-2-naphthamide The similar reaction as described in Example 50-(i) was carried out by using N-methyl-6-[(1-trityl-1H-imidazol-4-yl)carbonyl]-2-naphthamide (500 mg) and isobutyl-magnesium bromide in THF (1M; 5 mL) to give the titled compound (188 mg) as colorless powder.

¹H-NMR (CDCl₃) δ: 0.74 (3H, d, J=6.7 Hz), 0.89 (3H, d, J=6.7 Hz), 1.65–1.77 (1H, m), 2.09 (1H, d, J=6.0 Hz), 3.07 (1H, d, J=4.8 Hz), 3.64 (1H, s), 6.30 (1H, d J=4.8 Hz), 6.77 (1H, d, J=1.4 Hz), 7.11–7.20 (6H, m), 7.30–7.40 (10H, m), 7.51 (1H, dd, J=1.6, 8.6 Hz), 7.76–7.81 (3H, m), 8.03 (1H, s), 8.22 (1H, s). IR (KBr): 3304, 2951, 1647, 1545, 1493, 1447, 1161, 908, 733, 700 cm⁻¹.

(ii) Production of 6-[1-Hydroxy-1-(1H-imidazol-4-yl)-3-methylbutyl]-N-methyl-2-naphthamide In a similar manner to that described in Reference example 5, the reaction was carried out by using 6-[1-hydroxy-3-methyl-1-(1-trityl-1H-imidazol-4-yl)butyl]-N-methyl-2-naphthamide (163 mg) to give the titled compound (59 mg) as a colorless powder.

¹H-NMR (CDCl₃+CD₃OD) δ: 0.69 (3H, d, J=6.6 Hz), 0.93 (3H, d, J=6.6 Hz), 1.61–1.80 (1H, m), 2.23 (2H, d, J=6.0 Hz), 3.00 (3H, d, J=3.0 Hz), 6.89 (1H, s), 7.49–7.53 (2H, m), 7.63 (1H, d, J=3.6 Hz), 7.78–7.87 (3H, m), 8.04 (1H, s), 8.24 (1H, s). IR (KBr) 3300, 2951, 1645, 1558, 1412, 1310, 1161, 818 cm⁻¹.

Example 55

Production of (S)-(−)-6-[1-Hydroxy-1-(1H-imidazol-4-yl)-2-methylpropyl]-N-methyl-2-naphthamide 6-[1-Hydroxy-1-(1H-imidazol-4-yl)-2-methylpropyl]-N-methyl-2-naphthamide was chromatographed using a chiral column (Chiralpak AD), eluting with hexane-EtOH (85:15) to afford (S)-(−)-6-[1-hydroxy-1-(1H-imidazol-4-yl)-2-methylpropyl]-N-methyl-2-naphthamide as the first eluting enantiomer.

Optical purity; >99%ee (Chiralpak AD). $[\alpha]_D^{20}$=−55.4° (C=1.01, in methanol).

Example 56

Production of (S)-(−)-N-Ethyl-6-[1-hydroxy-1-(1H-imidazol-4-yl)-2-methylpropyl]-2-naphthamide N-ethyl-6-[1-Hydroxy-1-(1H-imidazol-4-yl)-2-methylpropyl]-2-naphthamide was chromatographed using a chiral column (Chiralpak AD), eluting with hexane-EtOH (85:15) to afford (S)-(−)-6-[1-hydroxy-1-(1H-imidazol-4-yl)-2-methylpropyl]-N-isopropyl-2-naphthamide as the first eluting enantiomer.

Optical purity; 99.2%ee (Chiralpak AD); $[\alpha]_D^{20}$=−51.0° (C=1.04, in methanol).

Example 57

Production of (S)-(−)-N-Cyclopropyl-6-[1-hydroxy-1-(1H-imidazol-4-yl)-2-methylpropyl]-2-naphthamide N-cyclopropyl-6-[1-Hydroxy-1-(1H-imidazol-4-yl)-2-methylpropyl]-2-naphthamide was chromatographed using a chiral column (Chiralpak AD), eluting with hexane-EtOH (85:15) to afford (S)-(−)-6-[1-hydroxy-1-(1H-imidazol-4-yl)-2-methylpropyl]-N-isopropyl-2-naphthamide as the first eluting enantiomer.

Optical purity; 99%ee (Chiralpak AD); $[\alpha]_D^{20}$=−45.2° (C=1.10, in methanol).

Example 58

Production of (S)-(−)-6-[1-Hydroxy-1-(1H-imidazol-4-yl)-2-methylpropyl]-N-isopropyl-2-naphthamide 6-[1-Hydroxy-1-(1H-imidazol-4-yl)-2-methylpropyl]-N-isopropyl-2-naphthamide was chromatographed using a chiral column (Chiralpak AD), eluting with hexane-EtOH (9:1) to afford (S)-(−)-6-[1-hydroxy-1-(1H-imidazol-4-yl)-2-methylpropyl]-N-isopropyl-2-naphthamide as the first eluting enantiomer.

Optical purity; 99.6%ee (Chiralpak AD); $[\alpha]_D^{20}$=−49.0° (C=1.08, in methanol).

Example 59

Production of 1-[5-Chloro-6-(1H-1,2,3-triazol-4-yl)-2-naphthyl]-1-(1H-imidazol-4-yl)-2-methyl-1-propanol (i) Production of 1-Chloro-6-[1-hydroxy-2-methyl-1-(1-trityl-1H-imidazol-4-yl)propyl]-2-naphthonitrile 1-Chloro-6-[1-hydroxy-2-methyl-1-(1-trityl-1H-imidazol-4-yl)propyl]-2-naphthyl trifluoromethanesulfonate (8.0 g) was used as a starting material. By the same procedure described in Reference example 4, the titled compound (4.87 g) was obtained as a colorless powder.

$^1$H-NMR (CDCl$_3$) δ: 0.71 (3H, d, J=6.6 Hz), 0.97 (3H, d, J=6.6 Hz), 2.47–2.61 (1H, m), 3.78 (1H, s), 6.83 (1H, d, J=1.4 Hz), 7.09–7.16 (6H, m), 7.30–7.37 (10H, m), 7.56 (1H, d, J=8.4 Hz), 7.77 (1H, dd, J=2.0, 9.2 Hz), 7.79 (1H, d, J=8.8 Hz), 8.15 (1H, d, J=1.4 Hz), 8.21 (1H, d, J=9.2 Hz). IR (KBr): 3269, 2968, 2235, 1331, 1171, 1003, 748, 702 cm$^{-1}$.

(ii) Production of 1-{5-Chloro-6-[5-(trimethylsilyl)-1H-1,2,3-triazol-4-yl]-2-naphthyl}-2-methyl-1-(1-trityl-1H-imidazol-4-yl)-1-propanol 1-Chloro-6-[1-hydroxy-2-methyl-1-(1-trityl-1H-imidazol-4-yl)propyl]-2-naphthonitrile (1.50 g) was used as a starting material. By the same procedure described in Example 4-(i), the titled compound (546 mg) was obtained as a colorless amorphous powder.

$^1$H-NMR (CDCl$_3$) δ: 0.15 (9H, s), 0.76 (3H, d, J=6.4 Hz), 0.99 (3H, d, J=6.6 Hz), 2.50–2.64 (1H, m), 3.91 (1H, s), 6.85 (1H, d, J=1.4 Hz), 7.11–7.18 (6H, m), 7.30–7.38 (10H, m), 7.40 (1H, d, J=1.4 Hz), 7.67 (1H, dd, J=1.8, 9.0 Hz), 7.74 (1H, d, J=8.2 Hz), 8.10 (1H, d, J=1.4 Hz), 8.22 (1H, d, J=9.2 Hz). IR (KBr): 3060, 2964, 1447, 1254, 908, 843, 731, 700 cm$^{-1}$.

(iii) Production of 1-[5-Chloro-6-(1H-1,2,3-triazol-4-yl)-2-naphthyl]-2-methyl-1-(1-trityl-1H-imidazol-4-yl)-1-propanol 1-{5-Chloro-6-[5-(trimethylsilyl)-1H-1,2,3-triazol-4-yl]-2-naphthyl}-2-methyl-1-(1-trityl-1H-imidazol-4-yl)-1-propanol (500 mg) was used as a starting material. By the same procedure described in Example 4-(ii), the titled compound (450 mg) was obtained as a pale yellow amorphous powder.

$^1$H-NMR (CDCl$_3$) δ: 0.76 (3H, d, J=6.6 Hz), 1.00 (3H, d, J=6.6 Hz), 2.47–2.63 (1H, m), 3.71 (1H, br s), 6.93 (1H, d, J=1.0 Hz), 7.15–7.22 (6H, m), 7.33–7.38 (9H, m), 7.49 (1H, dd, J=1.8, 9.0 Hz), 7.50 (1H, d, J=1.0 Hz), 7.57 (1H, d, J=8.4 Hz), 7.77 (1H, d, J=8.4 Hz), 7.89 (1H, d, J=1.4 Hz), 8.13 (1H, s), 8.22 (1H, d, J=9.0 Hz). IR (KBr): 3150, 2968, 1491, 1447, 1011, 908, 822, 729, 702 cm$^{-1}$.

(iv) Production of 1-[5-Chloro-6-(1H-1,2,3-triazol-4-yl)-2-naphthyl]-1-(1H-imidazol-4-yl)-2-methyl-1-propanol 1-[5-Chloro-6-(1H-1,2,3-triazol-4-yl)-2-naphthyl]-2-methyl-1-(1-trityl-1H-imidazol-4-yl)-1-propanol (420 mg) was used as a starting material. By the same procedure described in Reference example 5, the titled compound (193 mg) was obtained as a colorless amorphous powder.

$^1$H-NMR (DMSO-d$_6$) δ: 0.67 (3H, d, J=6.6 Hz), 0.87 (3H, d, J=6.6 Hz), 2.72–2.85 (1H, m), 3.36 (1H, br s), 5.32 (1H, br s), 7.04 (1H, s), 7.58 (1H, s), 7.96–8.07 (3H, m), 8.21 (1H, s), 8.22 (1H, d, J=8.8 Hz), 8.54 (1H, s), 11.86 (1H, br s). IR (KBr) 3200, 2968, 1487, 1308, 1015, 820 cm$^{-1}$.

Example 60

Production of 1-[5-Chloro-6-(1,3-oxazol-5-yl)-2-naphthyl]-1-(1H-imidazol-4-yl)-2-methyl-1-propanol (i) Production of 1-Chloro-6-[1-hydroxy-2-methyl-1-(1-trityl-1H-imidazol-4-yl)propyl]-2-naphthaldehyde To a ice-cooled solution of 1-chloro-6-[1-hydroxy-2-methyl-1-(1-trityl-1H-imidazol-4-yl)propyl]-2-naphthonitrile (1.20 g) in anhydrous CH$_2$Cl$_2$ (30 mL) was added dropwise diisobutylaluminium hydride (1.5 M in toluene; 4.2 mL), and the solution was stirred for 30 min at room temperature. The solution was poured into ice-cooled 1N HCl, and the mixture was neutralized with saturated NaHCO$_3$. Rochelle's salt (5.0 g) was added, and the mixture was stirred for 1 h at room temperature, and then extracted with CH$_2$Cl$_2$. The organic layer was washed with 1N-NaOH and dried over MgSO$_4$. After removal of the solvent in vacuo, the residue was purified by flash column chromatography on silica gel (hexane:AcOEt=3:1) to give a solid. The solid was washed with hexane-iPr$_2$O (1:1) to afford the titled compound (757 mg) as a colorless powder.

$^1$H-NMR (CDCl$_3$) δ: 0.73 (3H, d, J=6.6 Hz), 0.97 (3H, d, J=6.6 Hz), 2.48–2.61 (1H, m), 3.76 (1H, s), 6.83 (1H, d, J=1.2 Hz), 7.10–7.16 (6H, m), 7.30–7.35 (10H, m), 7.75–7.79 (2H, m), 7.92 (1H, d, J=8.4 Hz), 8.10 (1H, d, J=1.6 Hz), 8.36 (1H, d, J=9.2 Hz), 10.74 (1H, s). IR (KBr): 3522, 2961, 1682, 1327, 1225, 754, 700 cm$^{-1}$.

(ii) Production of 1-[5-Chloro-6-(1,3-oxazol-5-yl)-2-naphthyl]-2-methyl-1-(1-trityl-1H-imidazol-4-yl)-1-propanol 1-Chloro-6-[1-hydroxy-2-methyl-1-(1-trityl-1H-imidazol-4-yl)propyl]-2-naphthaldehyde (650 mg) was used as a starting material. By the same procedure described in Example 7-(i), the titled compound (693 mg) was obtained as a colorless powder.

$^1$H-NMR (CDCl$_3$) δ: 0.74 (3H, d, J=6.6 Hz), 0.97 (3H, d, J=6.6 Hz), 2.49–2.62 (1H, m), 3.80 (1H, s), 6.83 (1H, d, J=1.4 Hz), 7.10–7.26 (6H, m), 7.31–7.36 (10H, m), 7.69 (1H, dd, J=1.8, 9.0 Hz), 7.79 (1H, d, J=8.6 Hz), 7.87 (1H, d, J=8.6 Hz), 7.92 (1H, s), 8.01 (1H, s), 8.08 (1H, d, J=1.4 Hz), 8.28 (1H, d, J=9.0 Hz). IR (KBr): 3171, 2968, 1491, 1445, 1123, 1013, 818, 748, 702 cm$^{-1}$.

(iii) Production of 1-[5-Chloro-6-(1,3-oxazol-5-yl)-2-naphthyl]-1-(1H-imidazol-4-yl)-2-methyl-1-propanol 1-[5-Chloro-6-(1,3-oxazol-5-yl)-2-naphthyl]-2-methyl-1-(1-trityl-1H-imidazol-4-yl)-1-propanol (590 mg) was used as a starting material. By the same procedure described in Reference example 5, the titled compound (256 mg) was obtained as a colorless amorphous powder.

$^1$H-NMR (DMSO-d$_6$) δ: 0.66 (3H, d, J=6.6 Hz), 0.84 (3H, d, J=6.6 Hz), 2.73–2.90 (1H, m), 5.24 (1H, s), 7.05 (1H, s), 7.59 (1H, s), 7.88 (1H, d, J=8.4 Hz), 7.97–8.13 (3H, m), 8.20–8.24 (2H, m), 8.63 (1H, s), 11.85 (1H, br s). IR (KBr): 3167, 2966, 1506, 1298, 1245, 1132, 1105, 976, 820 cm$^{-1}$.

Example 61

Production of 6-[1-Hydroxy-1-(1H-imidazol-4-yl)-3-methylbutyl]-2-naphthamide (i) Production of 6-[1-Hydroxy-3-methyl-1-(1-trityl-1H-imidazol-4-yl)butyl]-2-naphthamide Methyl 6-[1-hydroxy-3-methyl-1-(1-trityl-1H-imidazol-4-yl)butyl]-2-naphthoate (2.0 g) was used as a starting material. By the same procedure described in Example 35-(i), the titled compound (1.32 g) was obtained as a colorless powder.

$^1$H-NMR (CDCl$_3$) δ: 0.73 (3H, d, J=7.0 Hz), 0.89 (3H, d, J=6.8 Hz), 1.61–1.81 (1H, m), 2.09 (2H, d, J=6.4 Hz), 3.72 (1H, s), 5.95 (1H, br s), 6.16 (1H, br s), 6.77 (1H, d, J=1.6 Hz), 7.11–7.18 (6H, m), 7.30–7.38 (10H, m), 7.52 (1H, dd, J=1.9, 8.5 Hz), 7.77–7.87 (3H, m), 8.04 (1H, s), 8.28 (1H, IR (KBr): 3173, 2949, 1659, 1445, 1396, 754, 700 cm$^{-1}$.

(ii) Production of 6-[1-Hydroxy-1-(1H-imidazol-4-yl)-3-methylbutyl]-2-naphthamide 6-[1-Hydroxy-3-methyl-1-(1-trityl-1H-imidazol-4-yl)butyl]-2-naphthamide (1.20 g) was used as a starting material. By the same procedure described in Reference example 5, the titled compound (467 mg) was obtained as a colorless amorphous powder.

$^1$H-NMR (CDCl$_3$+CD$_3$OD) δ: 0.69 (3H, d, J=6.6 Hz), 0.94 (3H, d, J=6.6 Hz), 1.58–1.80 (1H, m), 2.23 (2H, d, J=5.4 Hz), 6.89 (1H, s), 7.48–7.55 (2H, m), 7.79–7.84 (3H, m), 8.05 (1H, s), 8.31 (1H, s). IR (KBr): 3200, 2955, 1655, 1597, 1398 cm$^{-1}$.

Example 62

Production of 1-(1H-Imidazol-4-yl)-3-methyl-1-[6-(1H-1,2,3-triazol-4-yl)-2-naphthyl]-1-butanol (i) Production of 6-[1-Hydroxy-3-methyl-1-(1-trityl-1H-imidazol-4-yl)butyl]-2-naphthonitrile 6-[1-Hydroxy-3-methyl-1-(1-trityl-1H-imidazol-4-yl)butyl]-2-naphthyl trifluoromethanesulfonate (5.0 g) was used as a starting material. By the same procedure described in Reference example 4, the titled compound (4.08 g) was obtained as a pale yellow powder.

$^1$H-NMR (CDCl$_3$) δ: 0.73 (3H, d, J=6.6 Hz), 0.90 (3H, d, J=7.0 Hz), 1.60–1.78 (1H, m), 2.08 (2H, d, J=5.8 Hz), 3.70 (1H, s), 6.78 (1H, d, J=1.2 Hz), 7.11–7.16 (6H, m), 7.31–7.36 (10H, m), 7.55–7.59 (2H, m), 7.77 (1H, d, J=8.8 Hz), 7.87 (1H, d, J=8.4 Hz), 8.09 (1H, s), 8.17 (1H, s). IR (KBr): 3167, 2970, 2228, 1493, 1445, 758, 748, 702 cm$^{-1}$.

(ii) Production of 3-Methyl-1-{6-[5-(trimethylsilyl)-1H-1,2,3-triazol-4-yl]-2-naphthyl}-1-(1-trityl-1H-imidazol-4-yl)-1-butanol 6-[1-hydroxy-3-methyl-1-(1-trityl-1H-imidazol-4-yl)butyl]-2-naphthonitrile (1.60 g) was used as a starting material. By the same procedure described in Example 4-(i), the titled compound (723 mg) was obtained as a pale yellow amorphous powder.

$^1$H-NMR (CDCl$_3$) δ: 0.27 (9H, s), 0.74 (3H, d, J=6.6 Hz), 0.91 (3H, d, J=6.6 Hz), 1.64–1.83 (1H, m), 2.10–2.14 (2H, m), 4.05 (1H, s), 6.81 (1H, d, J=1.0 Hz), 7.14–7.21 (6H, m), 7.31–7.36 (10H, m), 7.45 (1H, dd, J=1.6, 9.4 Hz), 7.69 (1H, dd, J=1.6, 8.4 Hz), 7.72 (1H, d, J=8.6 Hz), 7.80 (1H, d, J=8.4 Hz), 7.97 (1H, s), 8.03 (1H, s). IR (KBr): 3060, 2953, 1493, 1445, 1252, 908, 843, 733, 702 cm$^{-1}$.

(iii) Production of 3-Methyl-1-[6-(1H-1,2,3-triazol-4-yl)-2-naphthyl]-1-(1-trityl-1H-imidazol-4-yl)-1-butanol 3-Methyl-1-{6-[5-(trimethylsilyl)-1H-1,2,3-triazol-4-yl]-2-naphthyl}-1-(1-trityl-1H-imidazol-4-yl)-1-butanol (670 mg) was used as a starting material. By the same procedure described in Example 4-(ii), the titled compound (503 mg) was obtained as a pale yellow amorphous powder.

$^1$H-NMR (CDCl$_3$) δ: 0.68 (3H, d, J=6.6 Hz), 0.91 (3H, d, J=6.6 Hz), 1.61–1.80 (1H, m), 2.07 (1H, dd, J=5.0, 14.4 Hz), 2.18 (1H, dd, J=6.2, 14.4 Hz), 3.66 (1H, brs), 6.94 (1H, d, J=1.2 Hz), 7.16–7.23 (6H, m), 7.30–7.38 (11H, m), 7.51 (1H, d, J=1.2 Hz), 7.59 (2H, s), 7.66 (1H, d, J=8.8 Hz), 7.86 (1H, s), 7.93 (1H, s). IR (KBr): 3143, 2953, 1495, 1447, 908, 746, 735, 702 cm$^{-1}$.

(iv) Production of 1-(1H-Imidazol-4-yl)-3-methyl-1-[6-(1H-1,2,3-triazol-4-yl)-2-naphthyl]-1-butanol 3-Methyl-1-[6-(1H-1,2,3-triazol-4-yl)-2-naphthyl]-1-(1-trityl-1H-imidazol-4-yl)-1-butanol (473 mg) was used as a starting material. By the same procedure described in Reference example 5, the titled compound (142 mg) was obtained as a pale yellow amorphous powder.

$^1$H-NMR (CDCl$_3$+CD$_3$OD) δ: 0.70 (3H, d, J=6.6 Hz), 0.95 (3H, d, J=6.6 Hz), 1.63–1.82 (1H, m), 2.24 (2H, d, J=5.8 Hz), 6.91 (1H, d, J=0.8 Hz), 7.48 (1H, dd, J=1.6, 8.6 Hz), 7.53 (1H, d, J=0.8 Hz), 7.79 (1H, d, J=8.8 Hz), 7.85–7.91 (2H, m), 7.96 (1H, s), 8.02 (1H, s), 8.18 (1H, s). IR (KBr): 3150, 2899, 1468, 1136, 1070, 988 cm$^{-1}$.

Example 63

Production of 1-(1H-Imidazol-4-yl)-3-methyl-1-[6-(1,3-oxazol-5-yl)-2-naphthyl]-1-butanol (i) Production of 6-[1-Hydroxy-3-methyl-1-(1-trityl-1H-imidazol-4-yl)butyl]-2-naphthaldehyde 6-[1-Hydroxy-3-methyl-1-(1-trityl-1H-imidazol-4-yl)butyl]-2-naphthonitrile (2.0 g) was used as a starting material. By the same procedure described in Example 60-(i), the titled compound (1.78 g) was obtained as a pale yellow amorphous powder.

$^1$H-NMR (CDCl$_3$) δ: 0.74 (3H, d, J=6.0 Hz), 0.90 (3H, d, J=6.0 Hz), 1.58–1.77 (1H, m), 2.09 (2H, d, J=5.8 Hz), 3.68 (1H, s), 6.79 (1H, d, J=1.6 Hz), 7.11–7.18 (6H, m), 7.31–7.36 (10H, m), 7.58 (1H, dd, J=2.0, 8.4 Hz), 7.87–7.92 (3H, m), 8.08 (1H, s), 8.29 (1H, s), 10.14 (1H, s). IR (KBr): 3057, 2951, 1693, 1447, 1157, 1128, 746, 702 cm$^{-1}$.

(ii) Production of 3-Methyl-1-[6-(1,3-oxazol-5-yl)-2-naphthyl]-1-(1-trityl-1H-imidazol-4-yl)-1-butanol 6-[1-Hydroxy-3-methyl-1-(1-trityl-1H-imidazol-4-yl)butyl]-2-naphthaldehyde (1.60 g) was used as a starting material. By the same procedure described in Example 7-(i), the titled compound (1.47 g) was obtained as a pale yellow powder.

$^1$H-NMR (CDCl$_3$) δ: 0.74 (3H, d, J=6.6 Hz), 0.90 (3H, d, J=7.0 Hz), 1.63–1.82 (1H, m), 2.10 (2H, d, J=5.8 Hz), 3.67 (1H, br s), 6.78 (1H, d, J=1.6 Hz), 7.12–7.19 (6H, m), 7.31–7.38 (10H, m), 7.44 (1H, s), 7.50 (1H, dd, J=1.8, 8.4 Hz), 7.69 (1H, dd, J=1.8, 8.8 Hz), 7.77 (1H, d, J=8.4 Hz), 7.84 (1H, d, J=8.8 Hz), 7.95 (1H, s), 8.01 (1H, s), 8.08 (1H, s). IR (KBr): 3204, 2945, 1491, 1445, 1169, 816, 748, 702 cm$^{-1}$.

(iii) Production of 1-(1H-Imidazol-4-yl)-3-methyl-1-[6-(1,3-oxazol-5-yl)-2-naphthyl]-1-butanol 3-Methyl-1-[6-(1,3-oxazol-5-yl)-2-naphthyl]-1-(1-trityl-1H-imidazol-4-yl)-1-butanol (1.30 g) was used as a starting material. By the same procedure described in Reference example 5, the title compound (389 mg) was obtained as a colorless powder.

$^1$H-NMR: (CDCl$_3$+CD$_3$OD) δ: 0.71 (3H, d, J=6.6 Hz), 0.96 (3H, d, J=6.8 Hz), 1.63–1.82 (1H, m), 2.24 (2H, d, J=6.0 Hz), 6.89 (1H, d, J=1.2 Hz), 7.44 (1H, s), 7.51 (1H, d, J=1.2 Hz), 7.52 (1H, dd, J=1.8, 8.8 Hz), 7.71 (1H, dd, J=1.8, 8.4 Hz), 7.80 (1H, d, J=8.8 Hz), 7.89 (1H, d, J=8.4 Hz), 8.00 (1H, s), 8.03 (1H, s), 8.10 (1H, s). IR (KBr): 3140, 2968, 1508, 1119, 891, 816 cm$^{-1}$.

Example 64

Production of 1-[6-(4,4-Dimethyl-4,5-dihydro-1,3-oxazol-2-yl)-2-naphthyl]-1-(1H-imidazol-4-yl)-2-methyl-1-propanol (i) Production of 1-[6-(4,4-Dimethyl-4,5-dihydro-1,3-oxazol-2-yl)-2-naphthyl]-2-methyl-1-(1-trityl-1H-imidazol-4-yl)-1-propanol 2-(6-Bromo-2-naphthyl)-4,4-dimethyl-4,5-dihydro-1,3-oxazole (1.0 g) and 2-methyl-1-(1-trityl-1H-imidazol-4-yl)-1-propanol (835 mg) were used as the starting materials. By the same procedure described in Reference example 1, the titled compound (1.25 g) was obtained as a colorless amorphous powder.

$^1$H-NMR (CDCl$_3$) δ: 0.74 (3H, d, J=7.0 Hz), 0.96 (3H, d, J=6.6 Hz), 1.42 (6H, s), 2.46–2.60 (1H, m), 3.76 (1H, s), 4.16 (2H, s), 6.81 (1H, d, J=1.6 Hz), 7.09–7.16 (6H, m), 7.28–7.35 (10H, m), 7.60 (1H, dd, J=1.8, 8.6 Hz), 7.79 (1H, d, J=8.6 Hz), 7.98 (1H, dd, J=1.6, 8.6 Hz), 8.03 (1H, d, J=0.8 Hz), 8.38 (1H, s). IR (KBr): 3062, 2970, 1645, 1495, 1447, 908, 733, 702 cm$^{-1}$.

(ii) Production of 1-[6-(4,4-Dimethyl-4,5-dihydro-1,3-oxazol-2-yl)-2-naphthyl]-1-(1H-imidazol-4-yl)-2-methyl-1-propanol 1-[6-(4,4-Dimethyl-4,5-dihydro-1,3-oxazol-2-yl)-2-naphthyl]-2-methyl-1-(1-trityl-1H-imidazol-4-yl)-1-propanol (1.0 g) was used as a starting material. By the same procedure described in Reference example 5, the title compound (438 mg) was obtained as a colorless amorphous powder.

$^1$H-NMR (CDCl$_3$) δ: 0.78 (3H, d, J=6.6 Hz), 1.00 (3H, d, J=7.0 Hz), 1.42 (6H, s), 2.61–2.74 (1H, m), 4.17 (2H, s), 6.98 (1H, d, J=1.2 Hz), 7.45 (1H, d, J=1.2 Hz), 7.62 (1H, dd, J=1.6, 8.8 Hz), 7.76 (1H, d, J=8.8 Hz), 7.78 (1H, d, J=8.8 Hz), 7.94 (1H, dd, J=1.6, 8.8 Hz), 8.05 (1H, s), 8.36 (1H, s). IR (KBr): 3100, 2970, 1643, 1354, 1306, 976, 821 cm$^{-1}$.

Example 65

Production of (S)-(−)-6-[1-Hydroxy-1-(1H-imidazol-4-yl)propyl]-N-methyl-2-naphthamide Fumarate (i) Production of (S)-(−)-6-[1-Hydroxy-1-(1H-imidazol-4-yl)propyl]-N-methyl-2-naphthamide 6-[1-Hydroxy-1-(1H-imidazol-4-yl)propyl]-N-methyl-2-naphthamide was chromatographed using a chiral column (Chiralpak OJ), eluting with hexane-EtOH-diethylamine (90:10:0.1) to afford (S)-(−)-6-[1-hydroxy-1-(1H-imidazol-4-yl)propyl]-N-methyl-2-naphthamide as the first eluting enantiomer.

Optical purity >99%ee (Chiralpak OJ, Daicel Chemical Industries, Ltd.).

(ii) Production of (S)-(−)-6-[1-Hydroxy-1-(1H-imidazol-4-yl)propyl]-N-methyl-2-naphthamide Fumarate To a heated (70° C.) solution of (S)-(−)-6-[1-hydroxy-1-(1H-imidazol-4-yl)propyl]-N-methyl-2-naphthamide (6.20 g) was added a hot solution of fumaric acid (2.20 g) in EtOH (30 mL), and the mixture was stand at room temperature. The obtained crystals were filtered, washed with EtOH, and dried in vacuo to give the title compound (7.15 g) as a colorless powder.

$[α]_D^{20}$=−46.0° (C=0.997, in methanol).

PREPARATION 1

Capsules

| | |
|---|---|
| (1) Compound obtained in Example 2 | 10 mg |
| (2) lactose | 90 mg |
| (3) microcrystalline cellulose | 70 mg |
| (4) magnesium stearate | 10 mg |
| One capsule | 180 mg |

The above (1), (2) and (3) and 5 mg of (4) were mixed. The mixture was granulated. To the granules was added (4) remaining. The whole content was sealed in a capsule.

PREPARATION 2

Tablets

| | |
|---|---|
| (1) Compound obtained in Example 1 | 10 mg |
| (2) lactose | 35 mg |
| (3) corn starch | 150 mg |
| (4) microcrystalline cellulose | 30 mg |
| (5) magnesium stearate | 5 mg |
| One Tablet | 230 mg |

The above (1), (2), (3), 20 mg of (4) and 2.5 mg of (5) were mixed. The mixture was granulated. To the granules was added (4) remaining and (5) remaining, and the mixture was compressively molded to give a tablet.

Experiment 1

Assay of Inhibitory Activity on a Rat Steroid C$_{17,20}$-lyase in Vitro

Inhibitory activity was determined according to the method described in The Prostate, vol. 26, 140–150(1995) with some modifications.

Testes excised from 13-week old, male SD rats were homogenized, and testicular microsomes were prepared by a series of centrifugation. The microsome protein (7 μg/10 μl) was added to 101 μl of 100 mM phosphate buffer (pH 7.4) in which 10 nM (final concentration) [1,2-3H]-17-α- hydroxyprogesterone, NADPH, and test compounds were dissolved. The reaction mixture was incubated for 7 min at 37° C., terminated by addition of 40 μl of ethyl acetate, and briefly centrifuged. The substrate and the products (testosterone and androstenedione) in the upper phase were separated by silica gel thin layer chromatography. Detection of the spots and measurement of the radioactivity were performed by a BAS 2000 Bioimage analyzer. The concentration of the test compounds necessary to reduce the concentration of the products by 50% (The concentration in the control group in which no test compound was added was taken as 100%) was calculated, and shown in Table 1.

TABLE 1

| | Test Compound | IC$_{50}$ (nM) |
|---|---|---|
| Example 2 | | 28 |
| Example 6 | | 15 |
| Example 7 | | 14 |
| Example 9 | | 6.1 |
| Example 18 | | 18 |
| Example 22 | | 3.3 |

Experiment 2
Assay of Inhibitory Activity on Testosterone Biosynthesis in Rats

Test compounds were orally administered to 9-week old, male SD (Sprague-Dawley rats at a dose of 50 mg/kg. Two-h later blood was taken and testosterone concentration in serum was measured by radioimmunoassay. The percentage of the testosterone concentration of the groups of rats, which received test compounds, to that of the control group was calculated, and regarded as the inhibitory activity.

TABLE 2

| Test Compound | | Inhibitory activity on testosterone bioxynthesis (T/C, %) |
|---|---|---|
| Example 6 | (structure) | 10 |
| Example 9 | (structure) | 4.5 |
| Example 18 | (structure) | 7.4 |

INDUSTRIAL APPLICABILITY

The compounds of the present invention and salts thereof have an inhibitory activity of steroid $C_{17,20}$-lyase and are useful for preventing and treating a mammal suffering from, for example, primary tumor, its metastasis and recurrence thereof, and various symptoms accompanied with these cancer, various diseases such as prostatic hypertrophy, virilism, hirsutism, male pattern alopecia, precocious puberty, endometriosis, uterus myoma, mastopathy, polycystic ovary syndrome, etc.

What is claimed is:
1. A compound of the formula:

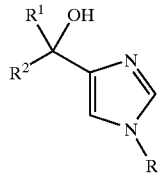

(I)

wherein R is a hydrogen atom or a protecting group,
R$^1$ is a lower alkyl group or a cyclic alkyl group, $R^2$ is a group represented by the formula:

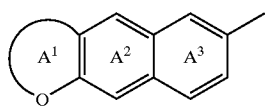

(1)

wherein ring $A^1$ is a 5- or 6-membered ring containing an oxygen atom optionally having substituents, and ring $A^2$ and ring $A^3$ may have substituents, a group represented by the formula:

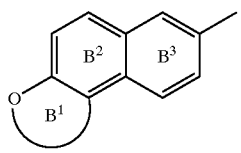

(2)

wherein the ring $B^1$ is a 5- or 6-membered ring containing an oxygen atom optionally having substituents and ring $B^2$ and ring $B^3$ may have substituents or a group of the formula:

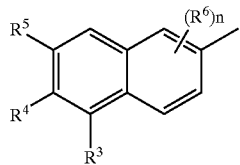

(3)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3, or a salt thereof.

2. A compound as claimed in claim 1,
wherein R is
(i) a hydrogen atom,
(ii) a formyl group or
(iii) a $C_{1-6}$ alkyl-carbonyl group, a phenyl-carbonyl group, a $C_{1-6}$ alkyl-oxycarbonyl group, an allyl-oxycarbonyl group, a phenyloxycarbonyl group, a $C_{7-10}$ aralkyl-oxy-carbonyl group, a trityl group, a N,N-dimethylaminosulfonyl group, a $C_{7-16}$ aralkyl-oxy-$C_{1-6}$ alkyl group each of which optionally having substituents selected from the group consisting of a halogen atom, a $C_{1-6}$ alkyl-carbonyl and nitro, $R^1$ is a straight chain or branched $C_{1-6}$ alkyl group or a $C_{3-6}$ cycloalkyl group,
the ring $A^1$ is a 5- or 6-membered ring containing an oxygen atom together with carbon atoms as ring constituting atoms and the ring may further contain a nitrogen atom and a sulfur atom as the ring constituting atoms, optionally having 1 to 4 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group,
the ring $A^2$ and the ring $A^3$ may have 1 to 3 substituents selected from the group consisting of
(i) a $C_{1-4}$ alkyl group optionally having substituents selected from the group consisting $C_{1-4}$ alkanoyl, carboxyl and $C_{1-4}$ alkoxy-carbonyl,
(ii) a $C_{1-3}$ alkoxy group,
(iii) a $C_{1-4}$ alkanoyl group,
(iv) a $C_{1-4}$ alkylsulfonyl group,
(v) a carbamoyl group,
(vi) a mono- or di-$C_{1-10}$ alkyl carbamoyl group,
(vii) a mono- or di-$C_{6-14}$ arylcarbamoyl group,
(viii) a mono- or di-$C_{7-16}$ aralkylcarbamoyl group,
(ix) a sulfamoyl group,
(x) a mono- or di-$C_{1-10}$ alkyl sulfamoyl group,
(xi) a mono- or di-$C_{6-14}$ arylsulfamoyl group and
(xii) a mono- or di-$C_{7-16}$ aralkyl sulfamoyl group at any substitutable position,
the ring $B^1$ is a 5- or 6-membered ring containing an oxygen atom together with carbon atoms as ring constituting atoms and the ring may further contain a nitrogen atom and a sulfur atom as the ring constituting atoms, optionally having 1 to 4 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group,
the ring $B^2$ and the ring $B^3$ may have 1 to 3 substituents selected from the group consisting of (i) a $C_{1-4}$ alkyl group optionally having substituents selected from the group consisting $C_{1-4}$ alkanoyl, carboxyl and $C_{1-4}$ alkoxy-carbonyl, (ii) a $C_{1-3}$ alkoxy group, (iii) a $C_{1-4}$ alkanoyl group, (iv) a $C_{1-4}$ alkylsulfonyl group, (v) a carbamoyl group, (vi) a mono- or di-$C_{1-10}$ alkyl carbamoyl group, (vii) a mono- or di-$C_{6-14}$ arylcarbamoyl group, (viii) a mono- or di-$C_{7-16}$ aralkylcarbamoyl group, (ix) a sulfamoyl group, (x) a mono- or di-$C_{1-10}$ alkyl sulfamoyl group, (xi) a mono- or di-$C_{6-14}$ arylsulfamoyl group and (xii) a mono- or di-$C_{7-16}$ aralkyl sulfamoyl group at any substitutable position, $R^3$ and $R^5$ is independently
(i) a hydrogen atom,
(ii) a $C_{1-4}$ alkyl group optionally having substituents selected from the group consisting of $C_{1-4}$ alkanoyl, carboxyl and $C_{1-4}$ alkoxy-carbonyl,
(iii) a group selected from the group consisting of a hydroxy group, a $C_{1-4}$ alkoxy group, a $C_{1-4}$ alkanoyloxy group, a carbamoyloxy group and a mono- or di-$C_{1-4}$ alkyl-carbamoyloxy group, (iv) a group selected from the group consisting of a thiol group, a $C_{1-4}$ alkylthio group and a $C_{1-4}$ alkanoylthio group, (v) a group selected from the group consisting of an amino group, a $C_{1-4}$ alkyl amino group, a di-$C_{1-4}$ alkylamino group and a $C_{1-4}$ alkanoylamino group, (vi) an acyl group selected from the group consisting of a formyl group, a $C_{1-6}$ alkanoyl group, a $C_{1-4}$ alkylsulfonyl group, a carbamoyl group, a mono- or di-$C_{1-10}$ alkyl carbamoyl group, a mono- or di-$C_{6-14}$ arylcarbamoyl group, a mono- or di-$C_{7-16}$ aralkyl carbamoyl group, a sulfamoyl group, a mono- or di-$C_{1-10}$ alkylsulfamoyl group, a mono- or di-$C_{6-14}$ arylsulfamoyl group and a mono- or di-$C_{7-16}$ aralkyl sulfamoyl group, or (vii) a halogen atom, $R^4$ is (I) a $C_{6-14}$ aryl group optionally having substituents selected from the group consisting of
(i) a $C_{1-4}$ alkyl group optionally having substituents selected from the group consisting $C_{1-4}$ alkanoyl, carboxyl and $C_{1-4}$ alkoxy-carbonyl,
(ii) a $C_{1-3}$ alkoxy group,
(iii) a $C_{1-4}$ alkanoyl group,
(iv) a $C_{1-4}$ alkylsulfonyl group,
(v) a carbamoyl group,
(vi) a mono- or di-$C_{1-10}$ alkyl carbamoyl group,
(vii) a mono- or di-$C_{6-14}$ arylcarbamoyl group,
(viii) a mono- or di-$C_{7-16}$ aralkylcarbamoyl group,
(ix) a sulfamoyl group,
(x) a mono- or di-$C_{1-10}$ alkyl sulfamoyl group,
(xi) a mono- or di-$C_{6-14}$ arylsulfamoyl group and
(xii) a mono- or di-$C_{7-16}$ aralkyl sulfamoyl group, (II) a 3- to 13-membered heterocyclic group which contains 1 to 4 hetero atoms selected from the group consisting of a nitrogen atom, an oxygen atom and a sulfur atom other than carbon atoms, optionally having substituents selected from the group consisting of
(i) a $C_{1-4}$ alkyl group optionally having substituents selected from the group consisting $C_{1-4}$ alkanoyl, carboxyl and $C_{1-4}$ alkoxy-carbonyl,
(ii) a $C_{1-3}$ alkoxy group,
(iii) a $C_{1-4}$ alkanoyl group,
(iv) a $C_{1-4}$ alkylsulfonyl group,
(v) a carbamoyl group,
(vi) a mono- or di-$C_{1-10}$ alkyl carbamoyl group,
(vii) a mono- or di-$C_{6-14}$ arylcarbamoyl group,
(viii) a mono- or di-$C_{7-16}$ aralkylcarbamoyl group,
(ix) a sulfamoyl group,
(x) a mono- or di-$C_{1-10}$ alkyl sulfamoyl group,
(xi) a mono- or di-$C_{6-14}$ arylsulfamoyl group and
(xii) a mono- or di-$C_{7-16}$ aralkyl sulfamoyl group, (III) a carbamoyl group, (IV) a mono- or di-$C_{1-10}$ alkyl-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (V) a mono- or di-$C_{3-7}$ cycloalkyl-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (VI) a mono- or di-$C_{6-14}$ aryl carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (VII) a mono- or di-$C_{7-16}$ aralkyl carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (VIII) a 3- to 7-membered cyclic amino-carbonyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, (IX) a 5- or 6-membered heterocyclic-carbamoyl group which contains 1 to 4 hetero atoms selected from a nitrogen atom, an oxygen atom and a sulfur atom other than carbon atoms optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, or (X) a $C_{1-6}$ alkoxy-carbamoyl group optionally having substituents selected from the group consisting of hydroxy, halogen atom, $C_{1-6}$ alkyl, $C_{3-7}$ cycloalkyl, $C_{1-6}$ alkoxy, $C_{1-6}$ acyl, carboxyl and $C_{1-6}$ alkoxy-carbonyl, $R^6$ is an optionally halogenated $C_{1-6}$ alkyl group, and n is an integer of 0 to 3.

3. A compound as claimed in claim 1, wherein R is a hydrogen atom or a protecting group, $R^1$ is a lower alkyl group or a cyclic alkyl group, $R^2$ is a group of the formula:

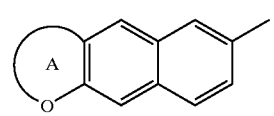

(1)

wherein the ring A is a 5- or 6-membered ring containing an oxygen atom, a group of the formula:

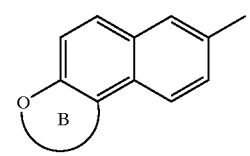

(2)

wherein the ring B is a 5- or 6-membered ring containing an oxygen atom or a group of the formula:

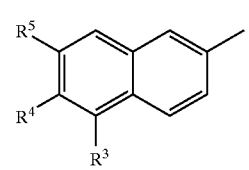

(3)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, and R⁴ is an aromatic hydrocarbon group optionally having substituents, a heterocyclic group optionally having substituents or a carbamoyl group optionally having substituents.

4. A compound as claimed in claim 1, wherein R is a hydrogen atom, $R^1$ is a straight chain or branched $C_{1-6}$ alkyl group, $R^2$ is a group represented by the formula: (3), and $R^4$ is a carbamoyl group optionally having substituents.

5. A compound as claimed in claim 1,
wherein R is a hydrogen atom or a trityl group,
$R^1$ is a straight chain or branched $C_{1-6}$ alkyl group or a $C_{3-6}$ cycloalkyl group,
the ring $A^1$ is

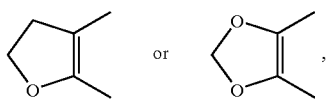

the ring $B^1$ is

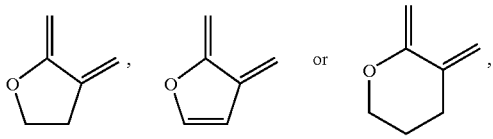

$R^3$ is a hydrogen atom, a $C_{1-4}$ alkyl group or a halogen atom,
$R^4$ is
  (i) a $C_{6-14}$ aryl group,
  (ii) a 5- or 6-membered heterocyclic group which contains 1 to 4 hetero atoms selected from a nitrogen atom, an oxygen atom and a sulfur atom other than carbon atoms,
  (iii) a carbamoyl group,
  (iii) a mono- or di-$C_{1-10}$ alkyl-carbamoyl group which may be substituted by hydroxy, $C_{3-7}$ cycloalkyl or $C_{1-6}$ alkoxy-carbonyl,
  (v) a mono- or di-$C_{3-7}$ cycloalkyl-carbamoyl group,
  (vi) a mono- or di-$C_{6-14}$ aryl carbamoyl group,
  (vii) a mono- or di-$C_{7-16}$ aralkyl carbamoyl group,
  (viii) a 3- to 7-membered cyclic amino-carbonyl group,
  (ix) a 5- or 6-membered heterocyclic-carbamoyl group which contains 1 to 4 hetero atoms selected from a nitrogen atom, an oxygen atom and a sulfur atom other than carbon atoms, or
  (x) a $C_{1-6}$ alkoxy-carbamoyl group,
$R^5$ is a hydrogen atom or a $C_{1-4}$ alkyl group.

6. A compound as claimed in claim 1, wherein R is a hydrogen atom, $R^1$ is a straight chain or branched $C_{1-6}$ alkyl group, $R^2$ is a group represented by the formula (3), $R^3$ is a hydrogen atom, $R^4$ is a mono- or di-$C_{1-10}$ alkyl-carbamoyl group or a $C_{3-7}$ cycloalkyl-carbamoyl group and $R^5$ is a hydrogen atom.

7. A compound as claimed in claim 1, which is
  (i) 6-[1-hydroxy-1-(1H-imidazol-4-yl)-2-methylpropyl]-N-methyl-2-naphthamide,
  (ii) 6-[1-hydroxy-1-(1H-imidazol-4-yl)-2-methylpropyl)-N-isopropyl-2-naphthamide,
  (iii) N-cyclopropyl-6-[1-hydroxy-1-(1H-imidazol-4-yl)-2-methylpropyl)-2-naphthamide,
  (iv) 6-[1-hydroxy-1-(1H-imidazol-4-yl)propyl]-N-methyl-2-naphthamide,
  (v) 6-[1-hydroxy-1-(1H-imidazol-4-yl)-3-methylbutyl]-N-methyl-2-naphthamide,
  (vi) (S)-(-)-6-[1-hydroxy-1-(1H-imidazol-4-yl)-2-methylpropyl]-N-methyl-2-naphthamide,
  (vii) (S)-(-)-N-cyclopropyl-6-[1-hydroxy-1-(1H-imidazol-4-yl)-2-methylpropyl]-2-naphthamide,
  (viii) (S)-(-)-6-[1-hydroxy-1-(1H-imidazol-4-yl)-2-methylpropyl)-N-isopropyl-2-naphthamide,
  (ix) (S)-(-)-6-[1-hydroxy-1-(1H-imidazol-4-yl)propyl]-N-methyl-2-naphthamide, or
  (x) (S)-(-)-6-[1-hydroxy-1-(1H-imidazol-4-yl)propyl]-N-methyl-2-naphthamide.fumarate, or a salt thereof.

8. A compound as claimed in claim 1, wherein the configuration of the carbon which connects to the hydroxy group is (S)-configuration.

9. A pro-drug of the compound of the formula:

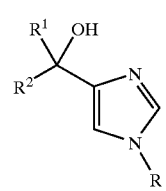

(I)

wherein R is a hydrogen atom or a protecting group,
$R^1$ is a lower alkyl group or a cyclic alkyl group,
$R^2$ is a group represented by the formula:

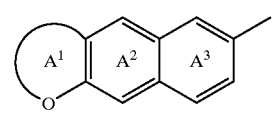

(1)

wherein ring $A^1$ is a 5- or 6-membered ring containing an oxygen atom optionally having substituents,
and ring $A^2$ and ring $A^3$ may have substituents,
a group represented by the formula:

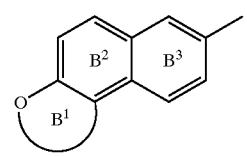

(2)

wherein the ring $B^1$ is a 5- or 6-membered ring containing an oxygen atom optionally having substituents and
ring $B^2$ and ring $B^3$ may have substituents or
a group of the formula:

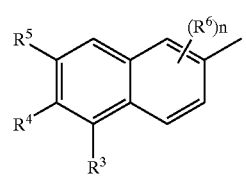

(3)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, R⁴ is an aromatic hydrocarbon group optionally having substituents, a heterocyclic group optionally having substituents or a carbamoyl group optionally having substituents, R⁶ is an optionally halogenated lower alkyl group and n is an integer of 0 to 3, or a salt thereof.

10. A pharmaceutical composition which comprises a compound of the formula:

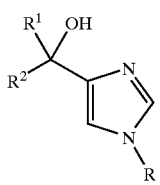

(I)

wherein R is a hydrogen atom or a protecting group,
R¹ is a lower alkyl group or a cyclic alkyl group,
R² is a group represented by the formula:

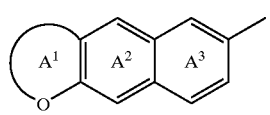

(1)

wherein ring A¹ is a 5- or 6-membered ring containing an oxygen atom optionally having substituents, and ring A² and ring A³ may have substituents,
a group represented by the formula:

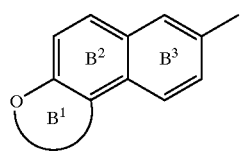

(2)

wherein the ring B¹ is a 5- or 6-membered ring containing an oxygen atom optionally having substituents and
ring B² and ring B³ may have substituents or
a group of the formula:

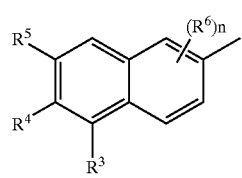

(3)

wherein each of R³ and R⁵ is a hydrogen atom, a lower alkyl group optionally having substituents, a hydroxyl group optionally having substituents, a thiol group optionally having substituents, an amino group optionally having substituents, an acyl group or a halogen atom, R⁴ is an aromatic hydrocarbon group optionally having substituents, a heterocyclic group optionally having substituents or a carbamoyl group optionally having substituents, R⁶ is an optionally halogenated lower alkyl group and n is an integer of 0 to 3, or a salt thereof, or a pro-drug thereof and a pharmaceutically acceptable carrier.

11. The pharmaceutical composition as claimed in claim 10, which is a steroid $C_{17,20}$-lyase inhibitor.

12. The composition as claimed in claim 10, which is an antitumor agent.

13. The composition for an antitumor agent as claimed in claim 10, which is a treating or preventing agent for breast cancer or prostate cancer.

14. An androgen reducer comprising a compound of the formula:

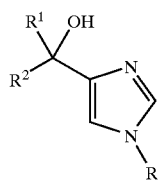

(I)

wherein R is a hydrogen atom or a protecting group,
R¹ is a lower alkyl group or a cyclic alkyl group,
R² is a group represented by the formula:

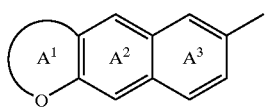

(1)

wherein ring A¹ is a 5- or 6-membered ring containing an oxygen atom optionally having substituents, and ring A² and ring A³ may have substituents,
a group represented by the formula:

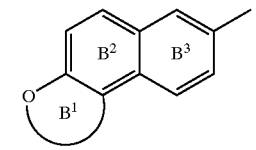

(2)

wherein the ring B¹ is a 5- or 6-membered ring containing an oxygen atom optionally having substituents and
ring B² and ring B³ may have substituents or a group of the formula:

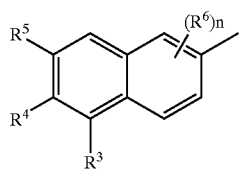

(3)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3, or a salt thereof, or a pro-drug thereof combined with an LH-RH modulator.

15. A process for producing a compound of the formula:

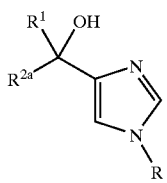

(Ia)

wherein $R^1$ is a lower alkyl group or a cyclic alkyl group, $R^{2a}$ is a group of the formula:

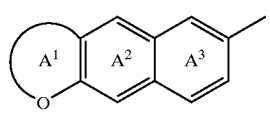

(1)

wherein ring $A^1$ is a 5- or 6-membered ring containing an oxygen atom optionally having substituents, and ring $A^2$ and ring $A^3$ may have substituents, a group represented by the formula:

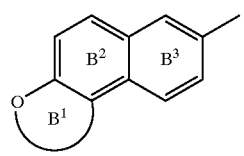

(2)

wherein the ring $B^1$ is a 5- or 6-membered ring containing an oxygen atom optionally having substituents and ring $B^2$ and ring $B^3$ may have substituents or a group of the formula:

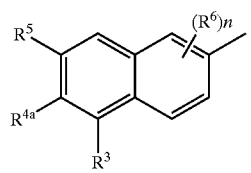

(3a)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^{4a}$ is a lower alkyl group optionally having substituents, a hydroxyl group optionally having substituents, a thiol group optionally having substituents, an amino group optionally having substituents, an acyl group, an aromatic hydrocarbon group optionally having substituents, a heterocyclic group optionally having substituents, a carbamoyl group optionally having substituents or halogen atom, $R^6$ is an optionally halogenated lower alkyl group and n is an integer of 0 to 3, and R is a hydrogen atom or a protecting group, or a salt thereof, which comprises reacting a compound of the formula:

(IIa)

wherein $R^1$ and $R^{2a}$ have the meanings given above, or a salt thereof with a reaction product of a compound of the formula:

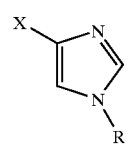

(III)

wherein X is a leaving group and

R has the meaning given above.

16. A method for inhibiting a steroid $C_{17,20}$-lyase which comprises administering a compound of the formula:

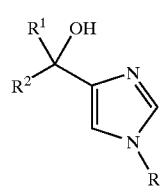

(I)

wherein R is a hydrogen atom or a protecting group, $R^1$ is a lower alkyl group or a cyclic alkyl group, $R^2$ is a group represented by the formula:

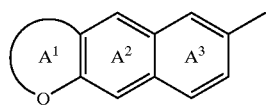
(1)

wherein ring $A^1$ is a 5- or 6-membered ring containing an oxygen atom optionally having substituents, and ring $A^2$ and ring $A^3$ may have substituents, a group represented by the formula:

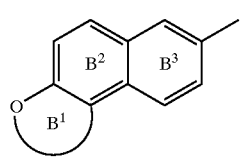
(2)

wherein the ring $B^1$ is a 5- or 6-membered ring containing an oxygen atom optionally having substituents and ring $B^2$ and ring $B^3$ may have substituents or a group of the formula:

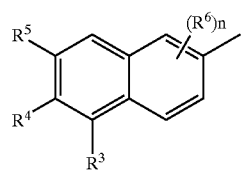
(3)

wherein each of $R^3$ and $R^5$ is a hydrogen atom, a lower alkyl group which may be substituted, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3, or a salt thereof, or a pro-drug thereof to mammals.

17. A method for preparing a pharmaceutical preparation comprising adding a pharmaceutically acceptable carrier to a compound represented by the formula:

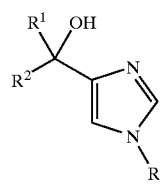
(I)

wherein R is a hydrogen atom or a protecting group, $R^1$ is a lower alkyl group or a cyclic alkyl group, $R^2$ is a group represented by the formula:

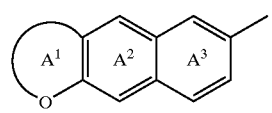
(1)

wherein ring $A^1$ is a 5- or 6-membered ring containing an oxygen atom optionally having substituents, and ring $A^2$ and ring $A^3$ may have substituents, a group represented by the formula:

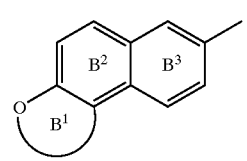
(2)

wherein the ring $B^1$ is a 5- or 6-membered ring containing an oxygen atom optionally having substituents and ring $B^2$ and ring $B^3$ may have substituents or a group of the formula:

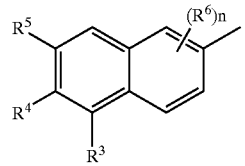
(3)

wherein each of $R^3$ and $R^5$ is a hydrogen atom, a lower alkyl group optionally having substituents, a hydroxyl group optionally having substituents, a thiol group optionally having substituents, an amino group optionally having substituents, an acyl group or a halogen atom, $R^4$ is an aromatic hydrocarbon group optionally having substituents, a heterocyclic group optionally having substituents or a carbamoyl group optionally having substituents, $R^6$ is an optionally halogenated lower alkyl group and n is an integer of 0 to 3, or a salt thereof, or a pro-drug thereof.

* * * * *

UNITED STATES PATENT AND TRADEMARK OFFICE
CERTIFICATE OF CORRECTION

PATENT NO.     : 6,649,643 B1
DATED          : November 18, 2003
INVENTOR(S)    : Akihiro Tasaka et al.

It is certified that error appears in the above-identified patent and that said Letters Patent is hereby corrected as shown below:

Title page,
Item [54], Title, please delete "IMIDAZOL-4-YLMEHANOLS AND THEIR USE AS INHIBITORS OF STEROID C17-20 LYASE" and insert -- IMIDAZOL-4-YLMETHANOLS AND THEIR USE AS INHIBITORS OF STEROIS C17-20 LYASE --.

Signed and Sealed this

Thirteenth Day of April, 2004

JON W. DUDAS
*Acting Director of the United States Patent and Trademark Office*